(12) United States Patent
Qiao et al.

(10) Patent No.: US 7,250,415 B2
(45) Date of Patent: Jul. 31, 2007

(54) 1,1-DISUBSTITUTEDCYCLOALKYL-, GLYCINAMIDYL-, SULFONYL-AMIDINO-, AND TETRAHYDROPYRIMIDINYL-CONTAINING DIAMINOALKYL, β-AMINOACIDS, α-AMINOACIDS AND DERIVATIVES THEREOF AS FACTOR XA INHIBITORS

(75) Inventors: Jennifer X. Qiao, Princeton, NJ (US); Donald J. Pinto, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 473 days.

(21) Appl. No.: 10/858,084

(22) Filed: Jun. 1, 2004

(65) Prior Publication Data

US 2004/0266761 A1   Dec. 30, 2004

Related U.S. Application Data

(60) Provisional application No. 60/475,731, filed on Jun. 4, 2003.

(51) Int. Cl.
*A61K 31/5375* (2006.01)
*A61K 31/404* (2006.01)
*A61K 31/17* (2006.01)
*C07C 233/40* (2006.01)
*C07D 265/30* (2006.01)
*C07D 409/12* (2006.01)
*C07D 209/14* (2006.01)
*C07D 333/22* (2006.01)

(52) U.S. Cl. .................. 514/237.8; 514/414; 514/422; 514/428; 514/616; 544/169; 548/467; 548/527; 548/568; 549/72; 564/157

(58) Field of Classification Search ............... 548/568; 514/408
See application file for complete search history.

(56) References Cited

U.S. PATENT DOCUMENTS 5,849,736 A * 12/1998 Wityak et al. ........... 514/227.8
2004/0077635 A1   4/2004 Qiao et al.

FOREIGN PATENT DOCUMENTS

| JP | 63-238051 A | 10/1988 |
| JP | 2002-326980 | * 11/2002 |
| WO | WO 02/057236 | 7/2002 |
| WO | WO 2004/014844 | 2/2004 |
| WO | WO 2004/024679 | 3/2004 |

OTHER PUBLICATIONS

Goto et al, STN International, HCAPLUS Database, Columbus, OH, Accession No. 2002:866813, Reg. No. 475277-15-7 (2007).*
Elodi et al., "Optimization of Conditions for the Catalytic Effect of the Factor IXa- Factor VIII Complex: Probably role of the complex in the amplification of blood coagulation," *Thrombosis Research*, vol. 15, pp. 617-629, 1979.
U.S. Appl. No. 10/801,518, filed Mar. 16, 2004, Pinto et al.
Jia et al., "Design, Synthesis and Biological Activity of Novel Non-Amidine Factor Xa Inhibitors. Part 1: $P_1$ structure-Activity Relationships of the Substituted 1-(2-Napthyl-1*H*-pyrazole-5-carboxylamides", *Bioorganic and Medicinal Chemistry Letters*, 2002, vol. 12, pp. 1651-1655.

* cited by examiner

*Primary Examiner*—Kamal A. Saeed
*Assistant Examiner*—Andrew B. Freistein
(74) *Attorney, Agent, or Firm*—Jing G. Sun

(57) ABSTRACT

The present application describes 1,1-disubstitutedcycloalkyl-, glycinamidyl-, sulfonyl-amidino-, and tetrahydropyrimidinyl-containing diaminoalkyl, β-aminoacids, α-aminoacids and derivatives thereof of Formula I:

$$P\text{-}M\text{-}M_1\text{I}$$

or a stereoisomer or pharmaceutically acceptable salt or solvate form thereof, wherein M is a linear core. Compounds of the present invention are useful as inhibitors of trypsin-like serine proteases, specifically factor Xa.

16 Claims, No Drawings

1,1-DISUBSTITUTEDCYCLOALKYL-, GLYCINAMIDYL-, SULFONYL-AMIDINO-, AND TETRAHYDROPYRIMIDINYL-CONTAINING DIAMINOALKYL, β-AMINOACIDS, α-AMINOACIDS AND DERIVATIVES THEREOF AS FACTOR XA INHIBITORS

CROSS-REFERENCE TO RELATED APPLICATIONS

The present application claims the priority benefit of U.S. Provisional Application No. 60/475,731, filed Jun. 4, 2003, which is expressly incorporated fully herein by reference.

FIELD OF THE INVENTION

This invention relates generally to 1,1-disubstitutedcycloalkyl-, glycinamidyl-, sulfonyl-amidino-, and tetrahydropyrimidinyl-containing diaminoalkyl, β-aminoacids, α-aminoacids and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

WO02/057236 describes factor Xa inhibitors of the following formula:

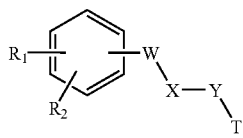

wherein $R_1$ is selected from a small number of nitrogen containing groups, W—X form a linear core with at least one O or N, Y can be a ring, and T can be a heterocycle. WO02/057236 does not suggest or exemplify compounds like those of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617-629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

Accordingly, the present invention provides novel 1,1-disubstitutedcycloalkyl-, glycinamidyl-, sulfonyl-amidino-, and tetrahydropyrimidinyl-containing ethylene diamine, β-aminoacids, α-aminoacids and derivatives thereof that are useful as factor Xa inhibitors or pharmaceutically acceptable salts, solvates, or prodrugs thereof.

The present invention also provides processes and intermediates for making the compounds of the present invention or a stereoisomer or a pharmaceutically acceptable salt, solvate, or prodrug form thereof.

The present invention provides pharmaceutical compositions comprising a pharmaceutically acceptable carrier and a therapeutically effective amount of at least one of the compounds of the present invention or a stereoisomer or a pharmaceutically acceptable salt, solvate, or prodrug form thereof.

The present invention provides a method for treating thromboembolic disorders comprising administering to a host in need of such treatment a therapeutically effective amount of at least one of the compounds of the present invention or a stereoisomer or a pharmaceutically acceptable salt, solvate, or prodrug form thereof.

The present invention provides a novel method of treating a patient in need of thromboembolic disorder treatment, comprising: administering a compound of the present invention or a stereoisomer or a pharmaceutically acceptable salt, solvate, or prodrug form thereof, in an amount effective to treat a thromboembolic disorder.

The present invention provides a novel method, comprising: administering a compound of the present invention or a stereoisomer or a pharmaceutically acceptable salt, solvate, or prodrug form thereof, in an amount effective to treat a thromboembolic disorder.

The present invention provides novel compounds and derivatives thereof for use in therapy.

The present invention provides the use of novel compounds for the manufacture of a medicament for the treatment of a thromboembolic disorder.

These and other provisions, which will become apparent during the following detailed description, have been achieved by the inventors' discovery that the compounds as defined below, or stereoisomers or pharmaceutically acceptable salts, solvates, or prodrugs thereof, are effective factor Xa inhibitors.

DETAILED DESCRIPTION OF PREFERRED EMBODIMENTS

In an embodiment, the present invention provides a novel compound of formula I:

P-M-M₁   I or a stereoisomer or pharmaceutically acceptable salt, solvate, or prodrug thereof, wherein:

M is 3-8 membered linear chain consisting of: carbon atoms, 0-3 carbonyl groups, 0-1 thiocarbonyl groups, and 0-4 heteroatoms selected from O, N, and $S(O)_p$, and M is substituted with 0-3 $R^{1a}$ and 0-2 $R^2$, and there are 0-2 double bonds and 0-1 triple bond; provided that other than an S—S, S—O or O—O bond is present in M and further provided that there are two or more groups selected from carbonyl groups, thiocarbonyl groups, and $S(O)_p$ groups present in the linear chain;

one of P and $M_1$ is —G and the other —A—B;

G is a group of formula IIa or IIb:

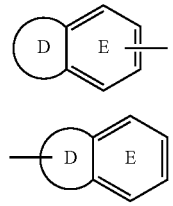

ring D, including the two atoms of Ring E to which it is attached, is a 5-6 membered ring consisting of: carbon atoms and 0-3 heteroatoms selected from N, O, and $S(O)_p$;

ring D is substituted with 0-2 R, 0-2 carbonyls, and there are 0-3 ring double bonds;

E is selected from phenyl, pyridyl, pyrimidyl, pyrazinyl, and pyridazinyl, and is substituted with 1-3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1-3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5-6 membered heterocycle consisting of: carbon atoms and 1-4 heteroatoms selected from N, O, and $S(O)_p$, wherein the 5-6 membered heterocycle is substituted with 0-1 carbonyls and 1-2 R and there are 0-3 ring double bonds;

R is, independently at each occurrence, selected from H, $C_{1-4}$ alkyl, F, Cl, Br, I, OH, —$OCH_3$, —$OCH_2CH_3$, —$OCH(CH_3)_2$, —$OCH_2CH_2CH_3$, CN, —C(=$NR^8$)$NR^7R^9$, —NHC(=$NR^8$)$NR^7R^9$, —ONHC(=$NR^8$)$NR^7R^9$, —$NR^8CH$(=$NR^7$), $NH_2$, —NH($C_{1-3}$ alkyl), —N($C_{1-3}$ alkyl)$_2$, —C(=NH)$NH_2$, —$CH_2NH_2$, —$CH_2NH$($C_{1-3}$ alkyl), —$CH_2N$($C_{1-3}$ alkyl)$_2$, —$CH_2CH_2NH_2$, —$CH_2CH_2NH$($C_{1-3}$ alkyl), —$CH_2CH_2N$($C_{1-3}$ alkyl)$_2$, —($CR^8R^9$)$_t$C(O)H, —($CR^8R^9$)$_t$C(O)$R^{2c}$, —($CR^8R^9$)$_t NR^7R^8$, —($CR^8R^9$)$_t$C(O)$NR^7R^8$, —($CR^8R^9$)$_t NR^7$C(O)$R^7$, —($CR^8R^9$)$_t OR^3$, —($CR^8R^9$)$_t S(O)_p NR^7R^8$, —($CR^8R^9$)$_t NR^7 S(O)_p R^7$, —($CR^8R^9$)$_t SR^3$, —($CR^8R^9$)$_t S(O)R^3$, —($CR^8R^9$)$_t S(O)_2 R^3$, and —$OCF_3$;

alternatively, when 2 R groups are attached to adjacent atoms, they combine to form methylenedioxy or ethylenedioxy;

A is selected from: $C_{3-10}$ carbocycle substituted with 0-2 $R^4$, and 5-12 membered heterocycle consisting of: carbon atoms and 1-4 heteroatoms selected from N, O, and $S(O)_p$, and substituted with 0-2 $R^4$;

B is selected from X—Y—$R^{4a}$, —N($B^1$)C(O)C($R^3R^{3g}$)$_{1-4}$ $NB^2B^3$, —C($B^5$)=$NB^4$, and

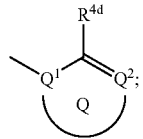

provided that the $R^{4d}$ shown is other than OH and that M and B are attached to different atoms on A and X and $R^{4a}$ are attached to the same atom on Y;

$B^1$ is selected from H, $CH_3$, —$CH_2CH_3$, —$CH_2CH_2CH_3$, —CH($CH_3$)$_2$, —$CH_2CH_2CH_2CH_3$, —$CH_2CH(CH_3)_2$, —CH($CH_3$)$CH_2CH_3$, —C($CH_3$)$_3$, —($CH_2$)$_{0-2}$—$C_{3-7}$ carbocycle substituted with 0-2 $R^{4b}$, and —($CH_2$)$_{0-2}$-5-6 membered heterocycle consisting of: carbon atoms and 1-4 heteroatoms selected from N, O, and $S(O)_p$, and substituted with 0-2 $R^{4b}$;

$B^2$ is selected from H, $C_{1-6}$ alkyl substituted with 0-2 $R^{4c}$, —C(O)$R^{2e}$, —C(O)O$R^{2d}$, —C(O)$NR^{2d}R^{2d}$, —C(O)NH($CH_2$)$_2 NR^{2d}R^{2d}$, —$SO_2 NR^{2d}R^{2d}$, —C(O)$NHSO_2$—$C_{1-4}$ alkyl, and —$S(O)_p R^{5a}$;

$B^3$ is selected from H, $C_{1-6}$ alkyl substituted with 0-2 $R^{4c}$, —($CH_2$)$_{0-2}$—$C_{3-6}$ carbocycle substituted with 0-2 $R^5$, and a —($CH_2$)$_{0-2}$-4-6 membered heterocycle consisting of: carbon atoms and 1-4 heteroatoms selected from N, O, and $S(O)_p$, and substituted with 0-2 $R^5$;

$B^4$ is selected from —$SO_2 R^{3b}$, —C(O)$R^{3b}$, —$SO_2 NR^3 R^{3b}$, —C(O)$NR^3 R^{3b}$, $OR^2$, $SR^2$, CN, and $NO_2$;

$B^5$ is $NR^2 R^{2f}$ or $CR^3 R^2 R^{2f}$;

$Q^1$ and $Q^2$ are each N;

alternatively, one of $Q^1$ and $Q^2$ is $CR^3$ and $R^{4d}$ is —$NR^2 R^{2a}$ or —$NR^{3a} B^4$, provided that when one of $Q^1$ and $Q^2$ is $CR^3$, then this $R^3$ group optionally forms a ring with the $R^2$ group of $R^{4d}$, this ring is a 5-6 membered ring consisting of, in addition to the C—C—N shown, carbon atoms and 0-1 additional heteroatoms selected from N, O, and $S(O)_p$, and this ring is substituted with 0-1 $R^5$;

ring Q is a 5-8 membered ring consisting of, in addition to the $Q^1$—$CR^{4d}$=$Q^2$ group shown, carbon atoms and 0-2 heteroatoms selected from N, O, and $S(O)_p$, and the ring is substituted with an additional 0-2 $R^{4d}$;

X is absent or is selected from —($CR^2 R^{2a}$)$_{1-4}$—, —$CR^2(CR^2R^{2b})(CH_2)_t$—, —C(O)—, —C(=$NR^{1b}$), —$CR^2(NR^{1b}R^2)$—, —$CR^2(OR^2)$—, —$CR^2(SR^2)$—, —C(O)$CR^2R^{2a}$—, —$CR^2R^{2a}$C(O)—, —S(O)—, —$S(O)_2$—, —$SCR^2R^{2a}$—, —S(O)$CR^2R^{2a}$—, —$S(O)_2 CR^2R^{2a}$—, —$CR^2R^{2a}$S—, —$CR^2R^{2a}$S(O)—, —$CR^2R^{2a}$$S(O)_2$—, —$S(O)_2 NR^2$—, —$S(O)_2 NR^2 CR^2 R^{2a}$—, —$CR^2R^{2a}S(O)_2 NR^2$—, —$NR^2 S(O)_2$—, —$CR^2R^{2a}NR^2 S(O)_2$—, —$NR^2 S(O)_2 CR^2R^{2a}$—, —$NR^2$C(O)—, —C(O)$NR^2$—, —$NR^2$C(O)$CR^2R^{2a}$—, —C(O)$NR^2 CR^2R^{2a}$—, —$CR^2 R^{2a}NR^2 C(O)$—, —$CR^2R^{2a}C(O)NR^2$—, $NR^2$, —$NR^2 CR^2 R^{2a}$—, —$CR^2R^{2a}NR^2$—, O, —$OCR^2R^{2a}$—, and —$CR^2R^{2a}$O—;

Y is selected from a $C_{3-10}$ carbocycle and 3-10 membered heterocycle, wherein the carbocycle or heterocycle consists of carbon atoms and 0-4 heteroatoms selected from N, O, and $S(O)_p$, the carbocycle or heterocycle further comprises 0-4 double bonds and 0-2 carbonyl groups, and the carbocycle or heterocycle is substituted with 0-2 $R^4$, provided that Y is other than a 1,3-dioxolanyl group;

alternatively, Y—$R^{4a}$ is —$CY^1 Y^2 R^{4a}$;

$Y^1$ and $Y^2$ are independently $C_{1-4}$ alkyl substituted with 0-2 $R^4$;

$R^{1a}$ is, independently at each occurrence, selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$C_{2-6}$ alkenylene-$R^{1b}$, —$C_{2-6}$ alkynylene-$R^{1b}$, —$(CR^3R^{3a})_r$—C(=$NR^{1b}$)$NR^3R^{1b}$, —$NR^3(CR^3R^{3a})_rR^{1c}$, —O$(CR^3R^{3a})_rR^{1c}$, —$(CR^3R^{3a})_r$SCR$^3R^{3a}R^{1c}$, —$(CR^3R^{3a})_rNR^3(CR^3R^{3a})_rR^{1b}$, —$(CR^3R^{3a})_rC(O)NR^2(CR^3R^{3a})_rR^{1b}$, —$CO_2(CR^3R^{3a})_rR^{1b}$, —O$(CR^3R^{3a})_rR^{1b}$, —$(CR^3R^{3a})_rS(CR^3R^{3a})_rR^{1b}$, —$S(O)_p$$(CR^3R^{3a})_rR^{1d}$, —O$(CR^3R^{3a})_rR^{1d}$, —$NR^3(CR^3R^{3a})_rR^{1d}$, —OC(O)$NR^3(CR^3R^{3a})_rR^{1d}$, —$NR^3C(O)NR^3(CR^3R^{3a})_rR^{1d}$, —$NR^3C(O)O(CR^3R^{3a})_rR^{1d}$, and —$NR^3C(O)(CR^3R^{3a})_rR^{1d}$, provided that $R^{1a}$ forms other than an N-halo, N—S, O—O, or N—CN bond;

alternatively, $CR^{1a}R^{1a}$ forms a $C_{3-10}$ carbocyclic or heterocyclic ring consisting of: carbon atoms and 0-4 heteroatoms selected from N, O, and $S(O)_p$, and this ring is substituted with 0-2 $R^4$ and has 0-3 ring double bonds;

$R^{1b}$ is, independently at each occurrence, selected from H, $C_{1-3}$ alkyl, F, Cl, Br, I, CN, —$NO_2$, —CHO, —$(CF_2)_rCF_3$, —$(CR^3R^{3a})_rOR^2$, —$NR^2R^{2a}$, —C(O)$R^{2b}$, —$CO_2R^{2b}$, —OC(O)$R^2$, —$(CF_2)_rCO_2R^{2a}$, —$S(O)_pR^{2b}$, —$NR^2(CH_2)_rOR^2$, —C(=$NR^{2c}$)$NR^2R^{2a}$, —$NR^2C(O)R^{2b}$, —$NR^2C(O)NR^2R^{2a}$, —$NR^2C(O)_2R^{2a}$, —OC(O)$NR^2R^{2a}$, —C(O)$NR^2R^{2a}$, —C(O)$NR^2(CH_2)_rOR^2$, —$SO_2NR^2R^{2a}$, —$NR^2SO_2NR^2R^{2a}$, —$NR^2SO_2R^2$, —C(O)$NR^2SO_2R^2$, —$SO_2R^2C(O)NR^2$, —$SO_2NR^2C(O)R^2$, $C_{3-10}$ carbocycle substituted with 0-2 $R^{4b}$, and 4-10 membered heterocycle consisting of carbon atoms and 1-4 heteroatoms selected from N, O, and $S(O)_p$, and substituted with 0-2 $R^{4b}$, provided that $R^{1b}$ forms other than an O—O, N-halo, N—S, or N—CN bond;

$R^{1c}$ is, independently at each occurrence, selected from H, —CH($CH_2OR^2$)$_2$, —C(O)$R^{2c}$, —C(O)$NR^2R^{2a}$, —$S(O)R^2$, —$S(O)_2R^2$, and —$SO_2NR^2R^{2a}$;

$R^{1d}$ is, independently at each occurrence, selected from $C_{3-6}$ carbocycle substituted with 0-2 $R^{4b}$ and 5-10 membered heterocycle consisting of carbon atoms and 1-4 heteroatoms selected from N, O, and $S(O)_p$, and substituted with 0-2 $R^{4b}$, provided that $R^{1d}$ forms other than an N—S bond;

$R^2$ is, independently at each occurrence, selected from H, $CF_3$, $C_{1-6}$ alkyl, benzyl, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from N, O, and $S(O)_p$, and substituted with 0-2 $R^{4b}$;

$R^{2a}$ is, independently at each occurrence, selected from H, $CF_3$, $C_{1-6}$ alkyl, benzyl, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from N, O, and $S(O)_p$, and substituted with 0-2 $R^{4b}$;

alternatively, $R^2$ and $R^{2a}$, together with the atom to which they are attached, combine to form a 5-8 membered saturated, partially saturated or unsaturated ring substituted with 0-2 $R^{4b}$ and consisting of: 0-1 additional heteroatoms selected from N, O, and $S(O)_p$;

$R^{2b}$ is, independently at each occurrence, selected from $CF_3$, $C_{1-4}$ alkoxy substituted with 0-2 $R^{4b}$, $C_{1-6}$ alkyl substituted with 0-2 $R^{4b}$, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from N, O, and $S(O)_p$, and substituted with 0-2 $R^{4b}$;

$R^{2c}$ is, independently at each occurrence, selected from $CF_3$, OH, $C_{1-4}$ alkoxy, $C_{1-6}$ alkyl, —$(CH_2)_r$—$C_{3-10}$ carbocycle substituted with 0-2 $R^{4b}$, and —$(CH_2)_r$-5-10 membered heterocycle containing from 1-4 heteroatoms selected from N, O, and $S(O)_p$, and substituted with 0-2 $R^{4b}$;

$R^{2d}$ is, independently at each occurrence, selected from H, $R^{4c}$, $C_{1-6}$ alkyl substituted with 0-2 $R^{4c}$, —$(CR^3R^{3a})_r$—$C_{3-10}$ carbocycle substituted with 0-2 $R^{4c}$, and —$(CR^3R^{3a})_r$-5-10 membered heterocycle substituted with 0-2 $R^{4c}$ and consisting of: carbon atoms and 1-4 heteroatoms selected from N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5-10 membered saturated, partially saturated, or unsaturated ring substituted with 0-2 $R^{4b}$ and consisting of: 0-1 additional heteroatoms selected from N, O, and $S(O)_p$;

$R^{2e}$ is, independently at each occurrence, selected from H, $R^{4c}$, $C_{1-6}$ alkyl substituted with 0-2 $R^{4c}$, —$(CR_3R^{3a})_r$—$C_{3-10}$ carbocycle substituted with 0-2 $R^{4c}$, and —$(CR^3R^{3a})_r$-5-10 membered heterocycle substituted with 0-2 $R^{4c}$ and consisting of: carbon atoms and 1-4 heteroatoms selected from N, O, and $S(O)_p$, provided that $R^{2e}$ forms other than a C(O)-halo or C(O)—$S(O)_p$ moiety;

$R^{2f}$ is, independently at each occurrence, selected from H, $CF_3$, $C_{1-4}$ alkoxy substituted with 0-2 $R^{4b}$, $C_{1-6}$ alkyl substituted with 0-2 $R^{4b}$, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from N, O, and $S(O)_p$, and substituted with 0-2 $R^{4b}$;

alternatively, $CR^3R^2R^{2f}$ forms a 5-8 membered ring consisting of: carbon atoms and 0-2 heteroatoms selected from N, O, and $S(O)_p$, and this ring is substituted with 0-2 $R^{4b}$;

alternatively, $NR^2R^{2f}$ forms a 5-8 membered ring consisting of: carbon atoms and 0-2 additional heteroatoms selected from N, O, and $S(O)_p$, and this ring is substituted with 0-2 $R^{4b}$;

alternatively, when $B^4$ is —$SO_2R^{3b}$ and $B^5$ is —$NR^2R^{2f}$, $R^{3b}$ and $R^{2f}$ combine to form a 5-8 membered ring consisting of: carbon atoms and 0-2 additional heteroatoms selected from N, O, and $S(O)_p$, and this ring is substituted with 0-2 $R^{4b}$;

alternatively, when $B^4$ is —C(O)$R^{3b}$ and $B^5$ is —$NR^2R^{2f}$, $R^{3b}$ and $R^{2f}$ combine to form a 5-8 membered ring consisting of: carbon atoms and 0-2 additional heteroatoms selected from N, O, and $S(O)_p$, and this ring is substituted with 0-2 $R^{4b}$;

alternatively, when $B^5$ is $NR^2R^{2f}$, $B^4$ and $R^{2f}$ combine to form a 5-8 membered ring consisting of: carbon atoms and 0-2 additional heteroatoms selected from N, O, and $S(O)_p$, and this ring is substituted with 0-2 $R^{4b}$ and the $R^2$ group of —$NR^2R^{2f}$, in addition to the groups recited below, is selected from —$SO_2R^{3b}$, —C(O)$R^{3b}$, and CN;

$R^3$ is, independently at each occurrence, selected from H, $CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, benzyl, and phenyl;

$R^{3a}$ is, independently at each occurrence, selected from H, $CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0-1 additional heteroatoms selected from N, O, and $S(O)_p$;

$R^{3b}$ is, independently at each occurrence, selected from H, $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, —$(C_{0-4}$ alkyl)-$C_{5-10}$ carbocycle substituted with 0-3 $R^{1a}$, and —$(C_{1-4}$ alkyl)-5-10 membered heterocycle substituted with 0-3 $R^{1a}$ and consisting of: carbon atoms and 1-4 heteroatoms selected from N, O, and $S(O)_p$;

R$^{3c}$ is, independently at each occurrence, selected from CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, benzyl, and phenyl;

R$^{3d}$ is, independently at each occurrence, selected from H, CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, C$_{1-4}$ alkyl-phenyl, and —C(=O)R$^{3c}$;

R$^{3g}$ is, independently at each occurrence, selected from H, CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —(CH$_2$)$_r$—C$_{3-6}$ carbocycle, and —(CH$_2$)$_r$-5-6 membered heterocycle consisting of: carbon atoms and 1-4 heteroatoms selected from N, O, and S(O)$_p$;

alternatively, when R$^3$ and R$^{3g}$ are attached to the same carbon atom, they combine with the attached carbon atom to form a cyclopropyl group;

R$^4$ is, independently at each occurrence, selected from H, =O, —(CR$^3$R$^{3a}$)$_r$OR$^2$, —(CR$^3$R$^{3a}$)$_r$F, —(CR$^3$R$^{3a}$)$_r$Cl, —(CR$^3$R$^{3a}$)$_r$Br, —(CR$^3$R$^{3a}$)$_r$I, C$_{1-4}$ alkyl, —(CR$^3$R$^{3a}$)$_r$CN, —(CR$^3$R$^{3a}$)$_r$NO$_2$, —(CR$^3$R$^{3a}$)$_r$NR$^2$R$^{2a}$, —(CR$^3$R$^{3a}$)$_r$C(O)R$^{2c}$, —(CR$^3$R$^{3a}$)$_r$NR$^2$C(O)R$^{2b}$, —(CR$^3$R$^{3a}$)$_r$C(O)NR$^2$R$^{2a}$, —(CR$^3$R$^{3a}$)$_r$NR$^2$C(O)NR$^2$R$^{2a}$, —(CR$^3$R$^{3a}$)$_r$C(=NR$^2$)NR$^2$R$^{2a}$, —(CR$^3$R$^{3a}$)$_r$C(=NS(O)$_2$R$^5$)NR$^2$R$^{2a}$, —(CR$^3$R$^{3a}$)$_r$NR$^2$C(=NR$^2$)NR$^2$R$^{2a}$, —(CR$^3$R$^{3a}$)$_r$C(O)NR$^2$C(=NR$^2$)NR$^2$R$^{2a}$, —(CR$^3$R$^{3a}$)$_r$SO$_2$NR$^2$R$^{2a}$, —(CR$^3$R$^{3a}$)$_r$NR$^2$SO$_2$NR$^2$R$^{2a}$, —(CR$^3$R$^{3a}$)$_r$NR$^2$SO$_2$—C$_{1-4}$ alkyl, —(CR$^3$R$^{3a}$)$_r$NR$^2$SO$_2$R$^5$, —(CR$^3$R$^{3a}$)$_r$S(O)$_p$R$^{5a}$, —(CR$^3$R$^{3a}$)$_r$(CF$_2$)$_r$CF$_3$, —NHCH$_2$R$^{1b}$, —OCH$_2$R$^{1b}$, —SCH$_2$R$^{1b}$, —NH(CH$_2$)$_2$(CH$_2$)$_t$R$^{1b}$, —O(CH$_2$)$_2$(CH$_2$)$_t$R$^{1b}$, —S(CH$_2$)$_2$(CH$_2$)$_t$R$^{1b}$, —(CR$^3$R$^{3a}$)$_r$—C$_{5-6}$ carbocycle substituted with 0-1 R$^5$, and a —(CR$^3$R$^{3a}$)$_r$-5-6 membered heterocycle consisting of: carbon atoms and 1-4 heteroatoms selected from N, O, and S(O)$_p$, and substituted with 0-1 R$^5$;

R$^{4a}$ is selected from C$_{1-6}$ alkyl substituted with 0-2 R$^{4c}$, C$_{2-6}$ alkenyl substituted with 0-2 R$^{4c}$, C$_{2-6}$ alkynyl substituted with 0-2 R$^{4c}$, —(CR$^3$R$^{3g}$)$_r$—C$_{5-10}$ carbocycle substituted with 0-3 R$^{4c}$, and —(CR$^3$R$^{3g}$)$_r$-5-10 membered heterocycle substituted with 0-3 R$^{4c}$ and consisting of: carbon atoms and 1-4 heteroatoms selected from N, O, and S(O)$_p$;

alternatively, R$^{4a}$ is selected from —(CR$^3$R$^{3g}$)$_r$CN, —(CR$^3$R$^{3g}$)$_r$C(=NR$^{2d}$)NR$^{2d}$R$^{2d}$, —(CR$^3$R$^{3g}$)$_r$NR$^{2d}$C(=NR$^{2d}$)NR$^{2d}$R$^{2d}$, —(CR$^3$R$^{3g}$)$_r$NR$^{2d}$C(R$^{2e}$)(=NR$^{2d}$), —(CR$^3$R$^{3g}$)$_r$NR$^{2d}$R$^{2d}$, —(CR$^3$R$^{3g}$)$_r$N(→O)R$^{2d}$R$^{2d}$, —(CR$^3$R$^{3g}$)$_r$OR$^{2d}$, —(CR$^3$R$^{3g}$)$_r$—NR$^{2d}$C(O)R$^{2e}$, —(CR$^3$R$^{3g}$)$_r$—C(O)R$^{2e}$, —(CR$^3$R$^{3g}$)$_r$—OC(O)R$^{2e}$, —(CR$^3$R$^{3g}$)$_r$—C(O)NR$^{2d}$R$^{2d}$, —(CR$^3$R$^{3g}$)$_r$—C(O)OR$^{2d}$, —(CR$^3$R$^{3g}$)$_r$—NR$^{2d}$C(O)NR$^{2d}$R$^{2d}$, —(CR$^3$R$^{3g}$)$_r$—OC(O)NR$^{2d}$R$^{2d}$, —(CR$^3$R$^{3g}$)$_r$—NR$^{2d}$C(O)OR$^{2d}$, —(CR$^3$R$^{3g}$)$_r$—SO$_2$NR$^{2d}$R$^{2d}$, —(CR$^3$R$^{3g}$)$_r$—NR$^{2d}$SO$_2$NR$^{2d}$R$^{2d}$, —(CR$^3$R$^{3g}$)$_r$—C(O)NR$^{2d}$SO$_2$R$^{2d}$, —(CR$^3$R$^{3g}$)$_r$—NR$^{2d}$SO$_2$R$^{2d}$, and —(CR$^3$R$^{3g}$)$_r$—S(O)$_p$R$^{2d}$, provided that S(O)$^p$R$^{2d}$ forms other than S(O)$_2$H or S(O)H and further provided that R$^{4a}$ is other than a hydroxamic acid;

R$^{4b}$ is, independently at each occurrence, selected from H, =O, —(CH$_2$)$_r$OR$^3$, —(CH$_2$)$_r$F, —(CH$_2$)$_r$Cl, —(CH$_2$)$_r$Br, —(CH$_2$)$_r$I, C$_{1-4}$ alkyl, —(CH$_2$)$_r$CN, —(CH$_2$)$_r$NO$_2$, —(CH$_2$)$_r$ NR$^3$R$^{3a}$, —(CH$_2$)$_r$C(O)R$^3$, —(CH$_2$)$_r$C(O)OR$^{3c}$, —(CH$_2$)$_r$NR$^3$C(O)R$^{3a}$, —(CH$_2$)$_r$—C(O)NR$^3$R$^{3a}$, —(CH$_2$)$_r$NR$^3$C(O)NR$^3$R$^{3a}$, —(CH$_2$)$_r$—C(=NR$^3$)NR$^3$R$^{3a}$, —(CH$_2$)$_r$NR$^3$C(=NR$^3$)NR$^3$R$^{3a}$, —(CH$_2$)$_r$SO$_2$NR$^3$R$^{3a}$, —(CH$_2$)$_r$NR$^3$SO$_2$NR$^3$R$^{3a}$, —(CH$_2$)$_r$NR$^3$SO$_2$—C$_{1-4}$ alkyl, —(CH$_2$)$_r$NR$^3$SO$_2$CF$_3$, —(CH$_2$)$_r$NR$^3$SO$_2$-phenyl, —(CH$_2$)$_r$S(O)$_p$CF$_3$, —(CH$_2$)$_r$S(O)$_p$—C$_{1-4}$ alkyl, —(CH$_2$)$_r$S(O)$_p$-phenyl, and —(CH$_2$)$_r$(CF$_2$)$_r$CF$_3$;

R$^{4c}$ is, independently at each occurrence, selected from =O, —(CR$^3$R$^{3a}$)$_r$OR$^2$, —(CR$^3$R$^{3a}$)$_r$F, —(CR$^3$R$^{3a}$)$_r$Br, —(CR$^3$R$^{3a}$)$_r$Cl, —(CR$^3$R$^{3a}$)$_r$CF$_3$, C$_{1-4}$ alkyl, C$_{2-6}$ alkenyl, C$_{2-6}$ alkynyl, —(CR$^3$R$^{3a}$)$_r$CN, —(CR$^3$R$^{3a}$)$_r$NO$_2$, —(CR$^3$R$^{3a}$)$_r$NR$^2$R$^{2a}$, —(CR$^3$R$^{3a}$)$_r$N(→O)R$^2$R$^{2a}$, —(CR$^3$R$^{3a}$)$_r$C(O)R$^{2c}$, —(CR$^3$R$^{3a}$)$_r$NR$^2$C(O)R$^{2b}$, —(CR$^3$R$^{3a}$)$_r$C(O)NR$^2$R$^{2a}$, —(CR$^3$R$^{3a}$)$_r$N=CHOR$^3$, —(CR$^3$R$^{3a}$)$_r$C(O)NR$^2$(CH$_2$)$_2$NR$^2$R$^{2a}$, —(CR$^3$R$^{3a}$)$_r$NR$^2$C(O)NR$^2$R$^{2a}$, —(CR$^3$R$^{3a}$)$_r$C(=NR$^2$)NR$^2$R$^{2a}$, —(CR$^3$R$^{3a}$)$_r$NR$^2$C(=NR$^2$)NR$^2$R$^{2a}$, —(CR$^3$R$^{3a}$)$_r$SO$_2$NR$^2$R$^{2a}$, —(CR$^3$R$^{3a}$)$_r$NR$^2$SO$_2$NR$^2$R$^{2a}$, —(CR$_3$R$^{3a}$)$_r$C(O)NR$^2$SO$_2$—C$_{1-4}$ alkyl, —(CR$^3$R$^{3a}$)$_r$NR$^2$SO$_2$R$^{5a}$, —(CR$^3$R$^{3a}$)$_r$C(O)NR$^2$SO$_2$R$^{5a}$, —(CR$^3$R$^{3a}$)$_r$S(O)$_p$R$^{5a}$, —(CF$_2$)$_r$CF$_3$, —(CR$_3$R$^{3a}$)$_r$C$_{3-10}$ carbocycle substituted with 0-2 R$^{4b}$, and —(CR$^3$R$^{3a}$)$_r$4-10 membered heterocycle substituted with 0-2 R$^{4b}$ and consisting of carbon atoms and 1-4 heteroatoms selected from N, O, and S(O)$_p$;

R$^{4d}$ is, independently at each occurrence, selected from H, —(CR$^3$R$^{3a}$)$_r$OR$^2$, —(CR$^3$R$^{3a}$)$_r$F, —(CR$^3$R$^{3a}$)$_r$Br, —(CR$^3$R$^{3a}$)$_r$Cl, C$_{1-4}$ alkyl, —(CR$^3$R$^{3a}$)$_r$CN, —(CR$^3$R$^{3a}$)$_r$NO$_2$, —(CR$^3$R$^{3a}$)$_r$NR$^2$R$^{2a}$, —(CR$^3$R$^{3a}$)$_r$C(O)R$^{2c}$, —(CR$^3$R$^{3a}$)$_r$NR$^2$C(O)R$^{2b}$, —(CR$^3$R$^{3a}$)$_r$C(O)NR$^2$R$^{2a}$, —(CR$^3$R$^{3a}$)$_r$N=CHOR$^3$, —(CR$^3$R$^{3a}$)$_r$C(O)NH(CH$_2$)$_2$NR$^2$R$^{2a}$, —(CR$^3$R$^{3a}$)$_r$NR$^2$C(O)NR$^2$R$^{2a}$, —(CR$^3$R$^{3a}$)$_r$C(=NR$^2$)NR$^2$R$^{2a}$, —(CR$^3$R$^{3a}$)$_r$NHC(=NR$^2$)NR$^2$R$^{2a}$, —(CR$^3$R$^{3a}$)$_r$SO$_2$NR$^2$R$^{2a}$, —(CR$^3$R$^{3a}$)$_r$NR$^2$SO$_2$NR$^2$R$^{2a}$, —(CR$_3$R$^{3a}$)$_r$NR$^2$SO$_2$—C$_{1-4}$ alkyl, —(CR$_3$R$^{3a}$)$_r$C(O)NHSO$_2$—C$_{1-4}$ alkyl, —(CR$^3$R$^{3a}$)$_r$NR$^2$SO$_2$R$^5$, —(CR$^3$R$^{3a}$)$_r$S(O)$_p$R$^{5a}$, —(CR$^3$R$^{3a}$)$_r$(CF$_2$)$_r$CF$_3$, —(CR$^3$R$^{3a}$)$_r$—C$_{5-6}$ carbocycle substituted with 0-1 R$^5$, and a —(CR$^3$R$^{3a}$)$_r$-5-6 membered heterocycle consisting of: carbon atoms and 1-4 heteroatoms selected from N, O, and S(O)$_p$, and substituted with 0-1 R$^5$;

R$^5$ is, independently at each occurrence, selected from H, C$_{1-6}$ alkyl, =O, —(CH$_2$)$_r$OR$^3$, F, Cl, Br, I, CN, NO$_2$, —(CH$_2$)$_r$NR$^3$R$^{3a}$, —(CH$_2$)$_r$C(O)R$^3$, —(CH$_2$)$_r$C(O)OR$^{3c}$, —(CH$_2$)$_r$NR$^3$C(O)R$^{3a}$, —(CH$_2$)$_r$C(O)NR$^3$R$^{3a}$, —(CH$_2$)$_r$NR$^3$C(O)NR$^3$R$^{3a}$, —(CH$_2$)$_r$CH(=NOR$^{3d}$), —(CH$_2$)$_r$C(=NR$^3$)NR$^3$R$^{3a}$, —(CH$_2$)$_r$NR$^3$C(=NR$^3$)NR$^3$R$^{3a}$, —(CH$_2$)$_r$ SO$_2$NR$^3$R$^{3a}$, —(CH$_2$)$_r$NR$^3$SO$_2$NR$^3$R$^{3a}$, —(CH$_2$)$_r$NR$^3$SO$_2$—C$_{1-4}$ alkyl, —(CH$_2$)$_r$NR$^3$SO$_2$CF$_3$, —(CH$_2$)$_r$NR$^3$SO$_2$-phenyl, —(CH$_2$)$_r$S(O)$_p$CF$_3$, —(CH$_2$)$_r$S(O)$_p$—C$_{1-4}$ alkyl, —(CH$_2$)$_r$S(O)$_p$-phenyl, —(CF$_2$)$_r$CF$_3$, phenyl substituted with 0-2 R$^6$, naphthyl substituted with 0-2 R$^6$, and benzyl substituted with 0-2 R$^6$;

R$^{5a}$ is, independently at each occurrence, selected from C$_{1-6}$ alkyl, —(CH$_2$)$_r$OR$^3$, —(CH$_2$)$_r$NR$^3$R$^{3a}$, —(CH$_2$)$_r$C(O)R$^5$, —(CH$_2$)$_r$C(O)OR$^{3c}$, —(CH$_2$)$_r$NR$^3$C(O)R$^{3a}$, —(CH$_2$)$_r$C(O)NR$^3$R$^{3a}$, —(CF$_2$)$_r$CF$_3$, phenyl substituted with 0-2 R$^6$, naphthyl substituted with 0-2 R$^6$, and benzyl substituted with 0-2 R$^6$, provided that R$^{5a}$ does not form a S—N or S(O)$_p$—C(O) bond;

R$^6$ is, independently at each occurrence, selected from H, OH, —(CH$_2$)$_r$OR$^2$, halo, C$_{1-4}$ alkyl, CN, NO$_2$, —(CH$_2$)$_r$NR$^2$R$^{2a}$, —(CH$_2$)$_r$C(O)R$^{2b}$, —NR$^2$C(O)R$^{2b}$, —NR$^2$C(O)NR$^2$R$^{2a}$, —C(=NH)NH$_2$, —NHC(=NH)NH$_2$, —SO$_2$NR$^2$R$^{2a}$, —NR$^2$SO$_2$NR$^2$R$^{2a}$, and —NR$^2$SO$_2$C$_{1-4}$ alkyl;

R$^7$ is, independently at each occurrence, selected from H, OH, C$_{1-6}$ alkyl, C$_{1-6}$ alkyl-C(O)—, C$_{1-6}$ alkyl-O—, —(CH$_2$)$_n$-phenyl, C$_{1-4}$ alkyl-OC(O)—, C$_{6-10}$ aryl-O—, C$_{6-10}$ aryl-OC(O)—, C$_{6-10}$ aryl-CH$_2$—C(O)—, C$_{1-4}$ alkyl-C(O)O—C$_{1-4}$ alkyl-OC(O)—, C$_{6-10}$ aryl-C(O)O—C$_{1-4}$ alkyl-OC(O)—, C$_{1-6}$ alkyl-NH$_2$—C(O)—, phenyl-NH$_2$—C(O)—, and phenyl C$_{1-4}$ alkyl-C(O)—;

R$^8$ is, independently at each occurrence, selected from H, C$_{1-6}$ alkyl, and —(CH$_2$)$_n$-phenyl;

alternatively, R$^7$ and R$^8$, when attached to the same nitrogen, combine to form a 5-10 membered heterocyclic ring consisting of carbon atoms and 0-2 additional heteroatoms selected from N, O, and $S(O)_p$;

$R^9$ is, independently at each occurrence, selected from H, $C_{1-6}$ alkyl, and $-(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6; and t, at each occurrence, is selected from 0, 1, 2, and 3.

Preferably, the novel compounds of the present invention are other than:

5-chloro-thiophene-2-carboxylic acid {2-hydroxy-3-[4-(methanesulfonylimino-pyrrolidin-1-yl-methyl)-phenylamino]-propyl}-amide; and N-(3-(4-(N,N-dimethyl-N'-(methylsulfonyl)carbamimidoyl)phenylamino)-2-hydroxypropyl)-5-chlorothiophene-2-carboxamide.

In a preferred embodiment, the present invention provides a novel compound, wherein:

one of P and $M_1$ is -G and the other -A-B;

M is 3-8 membered linear chain consisting of: carbon atoms, 0-3 carbonyl groups, 0-1 thiocarbonyl groups, and 1-4 heteroatoms selected from O, $S(O)_p$, and N, and M is substituted with 0-3 $R^{1a}$ and 0-2 $R^2$ and there are 0-1 double bonds, provided that other than an S—S, S—O or O—O bond is present in M and further provided that there are two or more groups selected from carbonyl groups, thiocarbonyl groups, and $S(O)_p$ groups present in the linear chain;

G is a group of formula IIa or IIb:

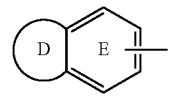

IIa

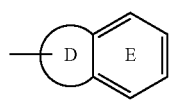

IIb ring D, including the two atoms of Ring E to which it is attached, is a 5-6 membered ring consisting of: carbon atoms and 0-2 heteroatoms selected from N, O, and $S(O)_p$;

ring D is substituted with 0-2 R and there are 0-3 ring double bonds;

E is selected from phenyl, pyridyl, pyrimidyl, pyrazinyl, and pyridazinyl, and is substituted with 1-3 R;

alternatively, ring D is absent, and ring E is selected from phenyl, pyridyl, pyrimidyl, and thienyl, and ring E is substituted with 1-3 R;

alternatively, ring D is absent, ring E is selected from phenyl, pyridyl, and thienyl, and ring E is substituted with 1 R and with a 5-6 membered heterocycle consisting of: carbon atoms and 1-4 heteroatoms selected from N, O, and $S(O)_p$, wherein the 5-6 membered heterocycle is substituted with 0-1 carbonyls and 1-2 R and there are 0-3 ring double bonds;

R is, independently at each occurrence, selected from H, $C_{1-4}$ alkyl, F, Cl, OH, $-OCH_3$, $-OCH_2CH_3$, $-OCH(CH_3)_2$, CN, $-C(=NH)NH_2$, $-C(=NH)NHOH$, $-C(=NH)NHOCH_3$, $NH_2$, $-NH(C_{1-3}$ alkyl), $-N(C_{1-3}$ alkyl)$_2$, $-C(=NH)NH_2$, $-CH_2NH_2$, $-CH_2NH(C_{1-3}$ alkyl), $-CH_2N(C_{1-3}$ alkyl)$_2$, $C(=NR^8)NR^7R^9$, $-(CR^8R^9)_rNR^7R^8$, $-C(O)NR^7R^8$, $-CH_2C(O)NR^7R^8$, $-S(O)_2R^3$, $-S(O)_pNR^7R^8$, $-CH_2S(O)_pNR^7R^8$, and $-OCF_3$;

alternatively, when 2 R groups are attached to adjacent atoms, they combine to form methylenedioxy or ethylenedioxy;

A is selected from: $C_{5-10}$ carbocycle substituted with 0-2 $R^4$, and 5-10 membered heterocycle consisting of: carbon atoms and 1-4 heteroatoms selected from N, O, and $S(O)_p$, and substituted with 0-2 $R^4$;

B is selected from $-N(B^1)C(O)C(R^3R^{3g})NB^2B^3$, $-N(B^1)C(O)C(R^3R^{3g})C(R^3R^{3g})NB^2B^3$,

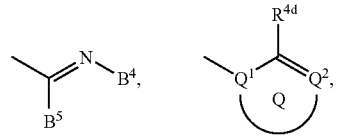

and

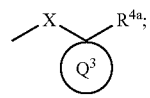

provided that the $R^{4d}$ shown is other than OH and that M and B are attached to different atoms on A;

$B^1$ is selected from H, $CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)CH_2CH_3$, $-C(CH_3)_3$, $-(CH_2)_{0-1}-C_{3-7}$ carbocycle substituted with 0-2 $R^{4b}$, and $-(CH_2)_{0-1}$-5-6 membered heterocycle consisting of: carbon atoins and 1-4 heteroatoms selected from N, O, and $S(O)_p$, and substituted with 0-2 $R^{4b}$;

$B^2$ is selected from H, $CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)CH_2CH_3$, $-C(CH_3)_3$, $-NR^{2d}R^{2d}$, $-CH_2-NR^{2d}R^{2d}$, $-CH_2CH_2-NR^{2d}R^{2d}$, $-C(O)R^{2e}$, $-C(O)NR^{2d}R^{2d}$, $-SO_2NR^{2d}R^{2d}$, and $-S(O)_pR^{5a}$;

$B^3$ is selected from H, $C_{1-6}$ alkyl substituted with 0-1 $R^{4c}$, $-(CH_2)_{0-1}-C_{3-6}$ carbocycle substituted with 0-1 $R^5$, and a $-(CH_2)_{0-1}$-5-6 membered heterocycle consisting of: carbon atoms and 1-4 heteroatoms selected from the group consisting of N, O, and $S(O)_p$, and substituted with 0-1 $R^5$;

$B^4$ is selected from $-SO_2R^{3b}$, $-C(O)R^{3b}$, $-SO_2NR^3R^{3b}$, $-C(O)NR^3R^{3b}$, $-OR^2$, and CN;

$B^5$ is $-NR^2R^{2f}$ or $-CR^3R^2R^{2f}$;

ring Q is a 5-6 membered ring consisting of, in addition to the $Q^1-CR^{4d}=Q^2$ group shown, carbon atoms and 0-2 heteroatoms selected from N, O, and $S(O)_p$, and the ring is substituted with an additional 0-2 $R^{4d}$;

$Q^1$ and $Q^2$ are each N;

alternatively, one of $Q^1$ and $Q^2$ is $CR^3$ and $R^{4d}$ is $-NR^2R^{2a}$ or $-NR^{3a}B^4$, provided that when one of $Q^1$ and $Q^2$ is $CR^3$, then this $R^3$ group optionally forms a ring with the $R^2$ group of $R^{4d}$, this ring is a 5-6 membered ring consisting of, in addition to the C—C—N shown, carbon atoms and 0-1 additional heteroatoms selected from N, O, and $S(O)_p$, and this ring is substituted with 0-1 $R^5$;

ring $Q^3$ is selected from $-CY^1Y^2$, a $C_{3-7}$ monocyclic carbocycle, and a 3-7 membered monocyclic heterocycle, wherein the carbocycle or heterocycle consists of: carbon atoms and 0-2 heteroatoms selected from N, O, and $S(O)_p$, the carbocycle or heterocycle further comprises 0-2 double bonds and 0-2 carbonyl groups, and the carbocycle or heterocycle is substituted with 0-2 $R^4$;

X is absent or is selected from $-(CR^2R^{2a})_{1-4}-$, $-C(O)-$, $-C(O)CR^2R^{2a}-$, $-CR^2R^{2a}C(O)-$, $-S(O)_2-$, $-S(O)_2CR^2R^{2a}-$, $-CR^2R^{2a}S(O)_2-$, $-S(O)_2NR^2-$, $-NR^2S(O)_2-$, $-NR^2C(O)-$, $-C(O)NR^2-$, $NR^2$, $-NR^2CR^2R^{2a}-$, $-CR^2R^{2a}NR^2-$, O, $-OCR^2R^{2a}-$, and $-CR^2R^{2a}O-$;

$Y^1$ and $Y^2$ are independently $C_{1-3}$ alkyl substituted with 0-1 $R^4$;

$R^{1a}$ is, independently at each occurrence, selected from H, $-(CR^3R^{3a})_r-R^{1b}$, $-(CR^3R^{3a})_r-O-(CR^3R^{3a})_r-R^{1b}$, $-C_{2-6}$ alkenylene-$R^{1b}$, $-C_{2-6}$ alkynylene-$R^{1b}$, $-(CR^3R^{3a})_r-C(=NR^{1b})NR^3R^{1b}$, $NR^3(CR^3R^{3a})_rR^{1c}$, $O(CR^3R^{3a})_rR^{1c}$, $(CR^3R^{3a})_rSCR^3R^{3a}R^{1c}$, $(CR^3R^{3a})_rNR^3(CR^3R^{3a})_rR^{1b}$, $(CR^3R^{3a})_rC(O)NR^2(CR^3R^{3a})_rR^{1b}$, $CO_2(CR^3R^{3a})_rR^{1b}$, $O(CR^3R^{3a})_rR^{1b}$, $S(O)_p(CR^3R^{3a})_rR^{1d}$, $O(CR^3R^{3a})_rR^{1d}$, $NR^3(CR^3R^{3a})_rR^{1d}$, $OC(O)NR^3(CR^3R^{3a})_rR^{1d}$, $NR^3C(O)NR^3(CR^3R^{3a})_rR^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;

alternatively, $CR^{1a}R^{1a}$ forms a $C_{3-10}$ carbocyclic or heterocyclic ring consisting of: carbon atoms and 0-4 heteroatoms selected from N, O, and $S(O)_p$, this ring being substituted with 0-2 $R^4$ and 0-3 ring double bonds;

$R^{1b}$ is selected from H, $CH_3$, $-CH_2CH_3$, $-CH_2CH_2CH_3$, $-CH(CH_3)_2$, F, Cl, Br, I, CN, CHO, $CF_3$, $-(CR^3R^{3a})_rOR^2$, $-NR^2R^{2a}$, $-C(O)R^{2b}$, $-CO_2R^{2b}$, $-OC(O)R^2$, $-CO_2R^{2a}$, $-S(O)_pR^2$, $-NR^2(CH_2)_rOR^2$, $-NR^2C(O)R^{2b}$, $-NR^2C(O)NR^2R^{2a}$, $-NR^2C(O)_2R^{2a}$, $-OC(O)NR^2R^{2a}$, $-C(O)NR^2R^{2a}$, $-C(O)NR^2(CH_2)_rOR^2$, $-SO_2NR^2R^{2a}$, $-NR^2SO_2NR^2R^{2a}$, $-NR^2SO_2R^2$, $-C(O)NR^2SO_2R^2$, $-SO_2NR^2C(O)R^2$, $C_{3-10}$ carbocycle substituted with 0-2 $R^{4b}$, and 4-10 membered heterocycle consisting of carbon atoms and 1-4 heteroatoms selected from N, O, and $S(O)_p$, and substituted with 0-2 $R^{4b}$, provided that $R^{1b}$ forms other than an O—O, N-halo, N—S, or N—CN bond;

$R^{1c}$ is, independently at each occurrence, selected from H, $-CH(CH_2OR^2)_2$, $-C(O)R^{2c}$, $-C(O)NR^2R^{2a}$, $-S(O)R^2$, $-S(O)_2R^2$, and $-SO_2NR^2R^{2a}$;

$R^2$ is, independently at each occurrence, selected from H, $CF_3$, $CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)CH_2CH_3$, $-C(CH_3)_3$, benzyl, $C_{5-6}$ carbocycle substituted with 0-2 $R^{4b}$, a $C_{5-6}$ carbocyclic-$CH_2$-group substituted with 0-2 $R^{4b}$, and 5-6 membered heterocycle consisting of: carbon atoms and 1-4 heteroatoms selected from N, O, and $S(O)_p$, and substituted with 0-2 $R^{4b}$;

$R^{2a}$ is, independently at each occurrence, selected from H, $CF_3$, $CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)CH_2CH_3$, $-C(CH_3)_3$, benzyl, $C_{5-6}$ carbocycle substituted with 0-2 $R^{4b}$, and 5-6 membered heterocycle consisting of: carbon atoms and 1-4 heteroatoms selected from N, O, and $S(O)_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from N, O, and $S(O)_p$;

$R^{2b}$ is, independently at each occurrence, selected from $CF_3$, $C_{1-4}$ alkoxy, $CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)CH_2CH_3$, $-C(CH_3)_3$, benzyl, $C_{5-6}$ carbocycle substituted with 0-2 $R^{4b}$, and 5-6 membered heterocycle consisting of: carbon atoms and 1-4 heteroatoms selected from N, O, and $S(O)_p$, and substituted with 0-2 $R^{4b}$;

$R^{2c}$ is, independently at each occurrence, selected from $CF_3$, OH, $C_{1-4}$ alkoxy, $CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)CH_2CH_3$, $-C(CH_3)_3$, benzyl, $C_{5-6}$ carbocycle substituted with 0-2 $R^{4b}$, and 5-6 membered heterocycle containing from 1-4 heteroatoms selected from N, O, and $S(O)_p$, and substituted with 0-2 $R^{4b}$;

$R^{2d}$ is, independently at each occurrence, selected from H, $R^{4c}$, $C_{1-4}$ alkyl substituted with 0-2 $R^{4c}$, $-(CR^3R^{3a})_r-C_{3-6}$ carbocycle substituted with 0-2 $R^{4c}$, and $-(CR^3R^{3a})_r$-5-6 membered heterocycle substituted with 0-2 $R^{4c}$ and consisting of: carbon atoms and 1-4 heteroatoms selected from N, O, and $S(O)_p$, provided that $R^{2d}$ forms other than a N-halo, N—C-halo, $S(O)_p$-halo, O-halo, N—S, S—N, $S(O)_p$—S$(O)_p$, S—O, O—N, O—S, or O—O moiety;

alternatively, $NR^{2d}R^{2d}$ forms a 5 or 6 membered saturated, partially saturated or unsaturated ring substituted with 0-2 $R^{4b}$ and consisting of: 0-1 additional heteroatoms selected from N, O, and $S(O)_p$;

$R^{2e}$ is, independently at each occurrence, selected from H, $R^{4c}$, $C_{1-4}$ alkyl substituted with 0-2 $R^{4c}$, $-(CR^3R^{3a})_r-C_{3-6}$ carbocycle substituted with 0-2 $R^{4c}$, and $-(CR^3R^{3a})_r$-5-6 membered heterocycle substituted with 0-2 $R^{4c}$ and consisting of: carbon atoms and 1-4 heteroatoms selected from N, O, and $S(O)_p$, provided that $R^{2e}$ forms other than a C(O)-halo or C(O)—S(O)$_p$ moiety;

$R^{2f}$ is, independently at each occurrence, selected from H, $CF_3$, $C_{1-4}$ alkoxy, $CH_3$, $-CH_2CH_3$, $-CH_2CH_2CH_3$, $-CH(CH_3)_2$, $-CH_2CH_2CH_2CH_3$, $-CH_2CH(CH_3)_2$, $-CH(CH_3)CH_2CH_3$, $-C(CH_3)_3$, benzyl, $C_{5-6}$ carbocycle substituted with 0-2 $R^{4b}$, and 5-6 membered heterocycle containing from 1-4 heteroatoms selected from N, O, and $S(O)_p$, and substituted with 0-2 $R^{4b}$;

alternatively, $CR^3R^2R^{2f}$ forms a 5-6 membered ring consisting of: carbon atoms and 0-2 heteroatoms selected from N, O, and $S(O)_p$, and this ring is substituted with 0-2 $R^{4b}$;

alternatively, $NR^2R^{2f}$ forms a 5-6 membered ring consisting of: carbon atoms and 0-2 additional heteroatoms selected from N, O, and $S(O)_p$, and this ring is substituted with 0-2 $R^{4b}$;

alternatively, when $B^5$ is $-NR^2R^{2f}$, $B^4$ and $R^{2f}$ combine to form a 5-6 membered ring consisting of: carbon atoms and 0-2 additional heteroatoms selected from N, O, and $S(O)_p$, and this ring is substituted with 0-2 $R^{4b}$ and the $R^2$ group of $-NR^2R^{2f}$ in addition to the groups recited below, is selected from $-SO_2R^{3b}$ and $-C(O)R^{3b}$;

$R^3$ is, independently at each occurrence, selected from H, $CH_3$, $-CH_2CH_3$, $-CH_2CH_2CH_3$, $-CH(CH_3)_2$, benzyl, and phenyl;

$R^{3a}$ is, independently at each occurrence, selected from H, $CH_3$, $-CH_2CH_3$, $-CH_2CH_2CH_3$, $-CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3b}$ is, independently at each occurrence, selected from H, $CF_3$, $CH_3$, $-CH_2CH_3$, $-CH_2CH_2CH_3$, $-CH(CH_3)_2$, $-(C_{0-1}$ alkyl)-$C_{5-6}$ carbocycle substituted with 0-1 $R^{1a}$, and $-(C_{0-1}$ alkyl)-5-6 membered heterocycle substituted with 0-1 $R^{1a}$ and consisting of: carbon atoms and 1-4 heteroatoms selected from N, O, and $S(O)_p$;

R³ᶜ is, independently at each occurrence, selected from CH₃, —CH₂CH₃, —CH₂CH₂CH₃, —CH(CH₃)₂, benzyl, and phenyl;

R³ᵈ is, independently at each occurrence, selected from H, CH₃, —CH₂CH₃, —CH₂CH₂CH₃, —CH(CH₃)₂, —CH₂-phenyl, —CH₂CH₂-phenyl, and —C(=O)R³ᶜ;

R⁴ is, independently at each occurrence, selected from H, =O, OR², —CH₂OR², —(CH₂)₂OR², F, Cl, Br, I, C₁₋₄ alkyl, CN, NO₂, —NR²R²ᵃ, —CH₂NR²R²ᵃ, —(CH₂)₂NR²R²ᵃ, —C(O)R²ᶜ, —NR²C(O)R²ᵇ, —C(O)NR²R²ᵃ, —NR²C(O)NR²R²ᵃ, —SO₂NR²R²ᵃ, —NR²SO₂NR²R²ᵃ, —S(O)ₚR⁵ᵃ, —NR²SO₂—C₁₋₄ alkyl, —NR²SO₂R⁵, CF₃, —CF₂CF₃, a C₅₋₆ carbocycle substituted with 0-1 R⁵, and a 5-6 membered heterocycle consisting of: carbon atoms and 1-4 heteroatoms selected from N, O, and S(O)ₚ, and substituted with 0-1 R⁵;

R⁴ᵇ is, independently at each occurrence, selected from H, =O, OR³, —CH₂OR³, F, Cl, CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, CN, NO₂, —NR³R³ᵃ, —CH₂NR³R³ᵃ, —C(O)R³, —CH₂—C(O)R³, —C(O)OR³ᶜ, —CH₂C(O)OR³ᶜ, —NR³C(O)R³ᵃ, —CH₂NR³C(O)R³ᵃ, —C(O)NR³R³ᵃ, —CH₂C(O)NR³R³ᵃ, —NR³C(O)NR³R³ᵃ, —CH₂NR³C(O)NR³R³ᵃ, —C(=NR³)NR³R³ᵃ, —CH₂C(=NR³)NR³R³ᵃ, —NR³C(=NR³)NR³R³ᵃ, —CH₂NR³C(=NR³)NR³R³ᵃ, —SO₂NR³R³ᵃ, —CH₂SO₂NR³R³ᵃ, —NR³SO₂NR³R³ᵃ, —CH₂NR³SO₂NR³R³ᵃ, —NR³SO₂—C₁₋₄ alkyl, —CH₂NR³SO₂—C₁₋₄ alkyl, —NR³SO₂CF₃, —CH₂NR³SO₂CF₃, —NR³SO₂-phenyl, —CH₂NR³SO₂-phenyl, —S(O)ₚCF₃, —CH₂S(O)ₚCF₃, —S(O)ₚ—C₁₋₄ alkyl, —CH₂S(O)ₚ—C₁₋₄ alkyl, —S(O)ₚ-phenyl, —CH₂S(O)ₚ-phenyl, CF₃, and —CH₂CF₃;

R⁴ᶜ is, independently at each occurrence, selected from =O, —(CR³R³ᵃ)ᵣOR², —(CR³R³ᵃ)ᵣF, —(CR³R³ᵃ)ᵣBr, —(CR³R³ᵃ)ᵣCl, —(CR³R³ᵃ)ᵣCF₃, C₁₋₄ alkyl, C₂₋₃ alkenyl, C₂₋₃ alkynyl, —(CR³R³ᵃ)ᵣCN, —(CR³R³ᵃ)ᵣNO₂, —(CR³R³ᵃ)ᵣNR²R²ᵃ, —(CR³R³ᵃ)ᵣN(→O)R²R²ᵃ, —(CR³R₃ₐ)ᵣC(O)R²ᶜ, —(CR³R³ᵃ)ᵣNR²C(O)R²ᵇ, —(CR³R³ᵃ)ᵣC(O)NR²R²ᵃ, —(CR³R³ᵃ)ᵣNR²C(O)NR²R²ᵃ, —(CR³R³ᵃ)ᵣSO₂NR²R²ᵃ, —(CR³R³ᵃ)ᵣNR²SO₂NR²R²ᵃ, —(CR³R³ᵃ)ᵣNR²SO₂R⁵ᵃ, —(CR³R³ᵃ)ᵣC(O)NR²SO₂R⁵ᵃ, —(CR³R³ᵃ)ᵣS(O)ₚR⁵ᵃ, —(CF₂)ᵣCF₃, —(CR³R³ᵃ)ᵣC₃₋₁₀ carbocycle substituted with 0-2 R⁴ᵇ, and —(CR³R³ᵃ)ᵣ5-10 membered heterocycle consisting of carbon atoms and 1-4 heteroatoms selected from N, O, and S(O)ₚ, and substituted with 0-2 R⁴ᵇ;

R⁴ᵈ is, independently at each occurrence, selected from H, —CH₂OR², OR², C₁₋₄ alkyl, —CH₂CN, CN, —CH₂NO₂, NO₂, —CH₂NR²R²ᵃ, —NR²R²ᵃ, —CH₂C(O)R²ᶜ, —C(O)R²ᶜ, —NR²C(O)R²ᵇ, —(CH₂)ᵣC(O)NR²R²ᵃ, —NR²C(O)NR²R²ᵃ, —(CH₂)ᵣSO₂NR²R²ᵃ, —NR²SO₂NR²R²ᵃ, —NR²SO₂R⁵, —(CH₂)ᵣS(O)ₚR⁵ᵃ, —CH₂CF₃, CF₃, —(CH₂)₀₋₁—C₅₋₆ carbocycle substituted with 0-1 R⁵, and a —(CH₂)₀₋₁-5-6 membered heterocycle consisting of: carbon atoms and 1-4 heteroatoms selected from the group consisting of N, O, and S(O)ₚ, and substituted with 0-1 R⁵;

R⁵ is, independently at each occurrence, selected from H, =O, CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, —OR³, —CH₂OR³, F, Cl, CN, NO₂, —NR³R³ᵃ, —CH₂NR³R³ᵃ, —C(O)R³, —CH₂C(O)R³, —C(O)OR³ᶜ, —CH₂C(O)OR³ᶜ, —NR³C(O)R³ᵃ, —C(O)NR³R³ᵃ, —NR³C(O)NR³R³ᵃ, —CH(=NOR³ᵈ), —C(=NR³)NR³R³ᵃ, —NR³C(=NR³)NR³R³ᵃ, —SO₂NR³R³ᵃ, —NR³SO₂NR³R³ᵃ, —NR³SO₂—C₁₋₄ alkyl, —NR³SO₂CF₃, —NR³SO₂-phenyl, —S(O)ₚCF₃, —S(O)ₚ—C₁₋₄ alkyl, —S(O)ₚ-phenyl, CF₃, phenyl substituted with 0-2 R⁶, naphthyl substituted with 0-2 R⁶, and benzyl substituted with 0-2 R⁶;

R⁵ᵃ is, independently at each occurrence, selected from CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, OR³, —CH₂OR³, —NR³R³ᵃ, —CH₂NR³R³ᵃ, —C(O)R³, —CH₂C(O)R³, —C(O)OR³ᶜ, —CH₂C(O)OR³ᶜ, —NR³C(O)R³ᵃ, —CH₂NR³C(O)R³ᵃ, —C(O)NR³R³ᵃ, —CH₂C(O)NR³R³ᵃ, CF₃, —CF₂CF₃, phenyl substituted with 0-2 R⁶, naphthyl substituted with 0-2 R⁶, and benzyl substituted with 0-2 R⁶, provided that R⁵ᵃ does not form a S—N or S(O)ₚ—C(O) bond; and R⁶ is, independently at each occurrence, selected from H, OH, —OR², F, Cl, CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, CN, NO₂, —NR²R²ᵃ, —CH₂NR²R²ᵃ, —C(O)R²ᵇ, —CH₂C(O)R²ᵇ, —NR²C(O)R²ᵇ, —NR²C(O)NR²R²ᵃ, —C(=NH)NH₂, —NHC(=NH)NH₂, —SO₂NR²R²ᵃ, —NR²SO₂NR²R²ᵃ, and —NR²SO₂C₁₋₄ alkyl.

In another preferred embodiment, the present invention provides a novel compound, wherein:

one of P and M₁ is -G and the other -A-B;

M is 3-8 membered linear chain consisting of: carbon atoms, 0-3 carbonyl groups, 0-1 thiocarbonyl groups, and 1-3 heteroatoms selected from O, S(O)ₚ, and N, and M is substituted with 0-3 R¹ᵃ and 0-2 R² and there are 0-2 double bonds, provided that other than an S—S, S—O, or O—O bond is present in M and further provided that there are two or more groups selected from carbonyl groups, thiocarbonyl groups, and S(O)ₚ groups present in the linear chain;

G is selected from the group:

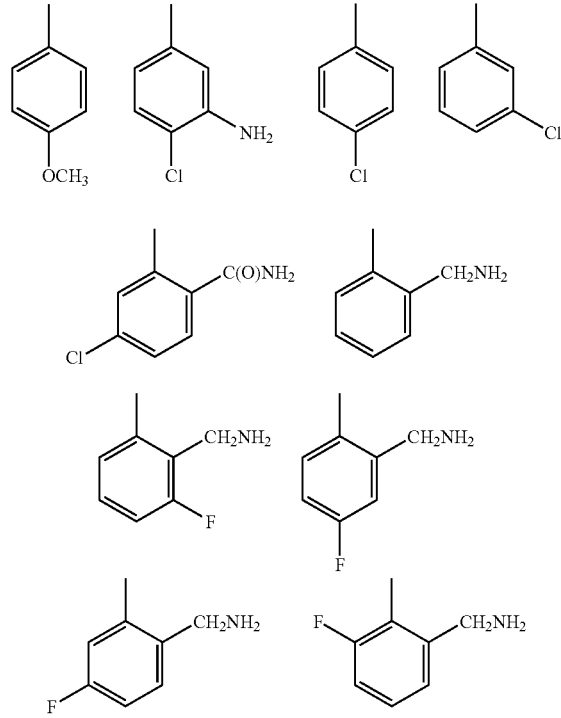

-continued
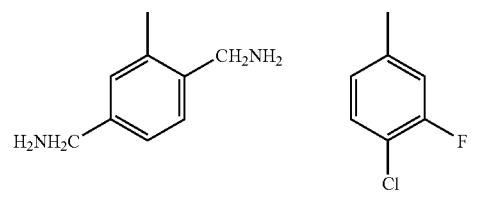
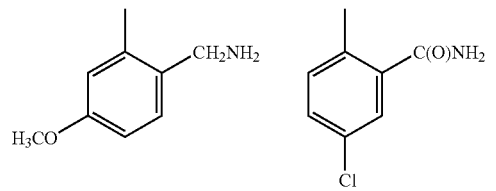
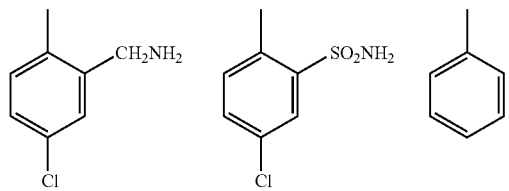
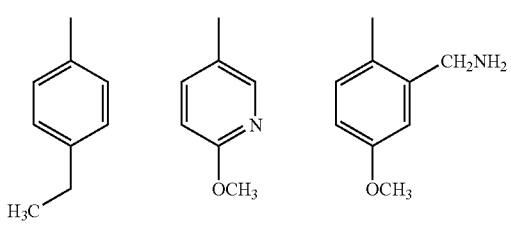
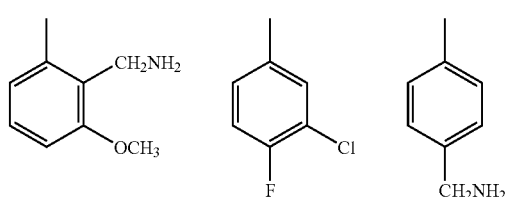
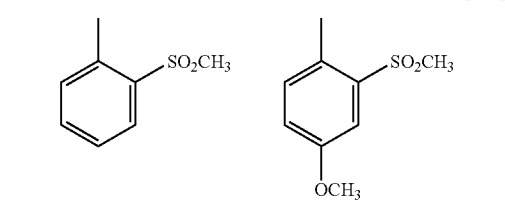
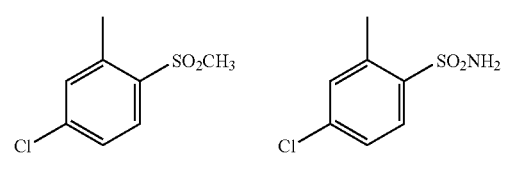
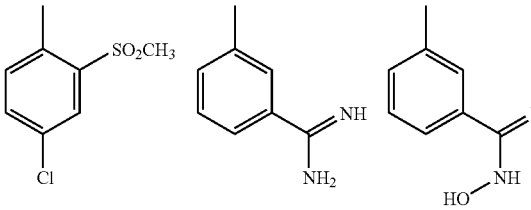
-continued
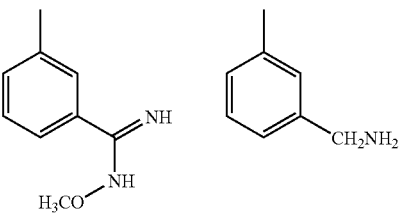

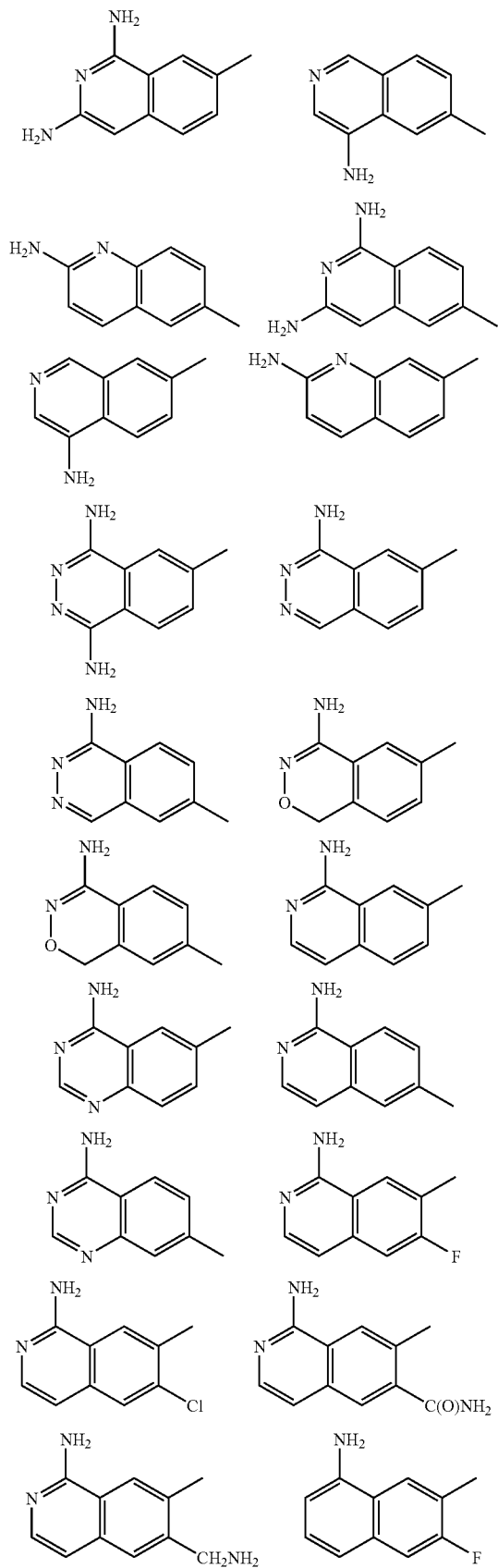
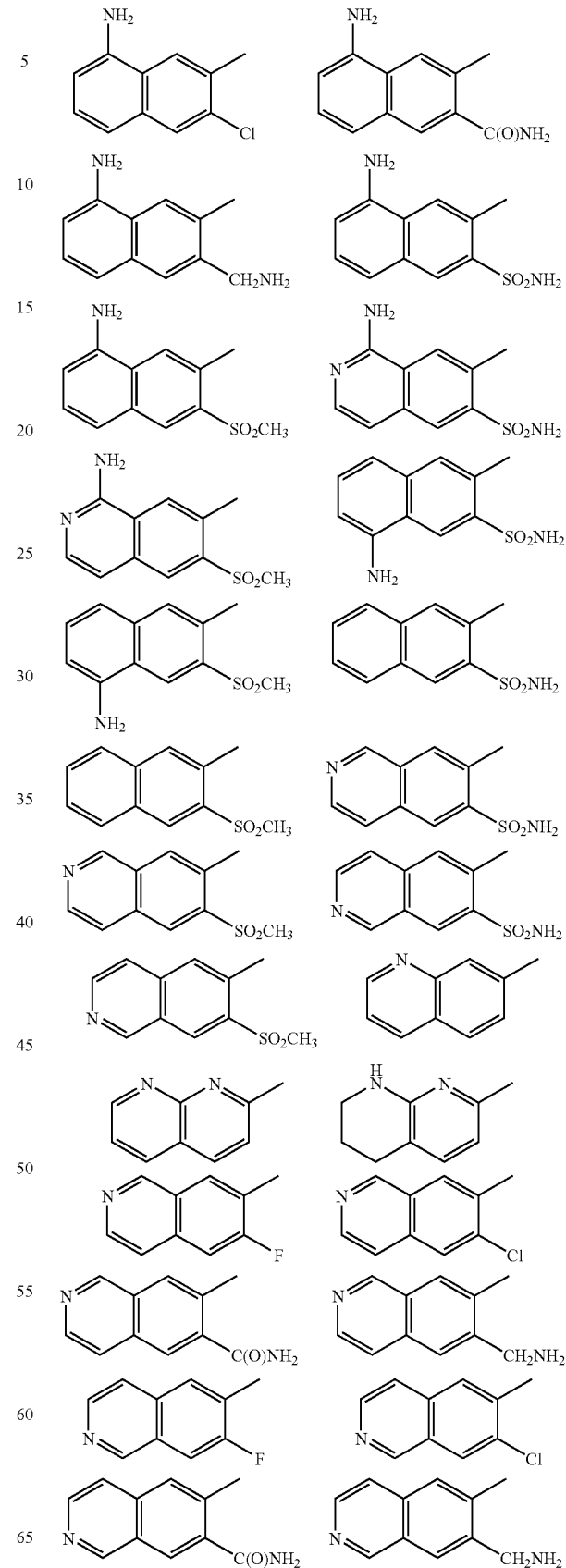

-continued
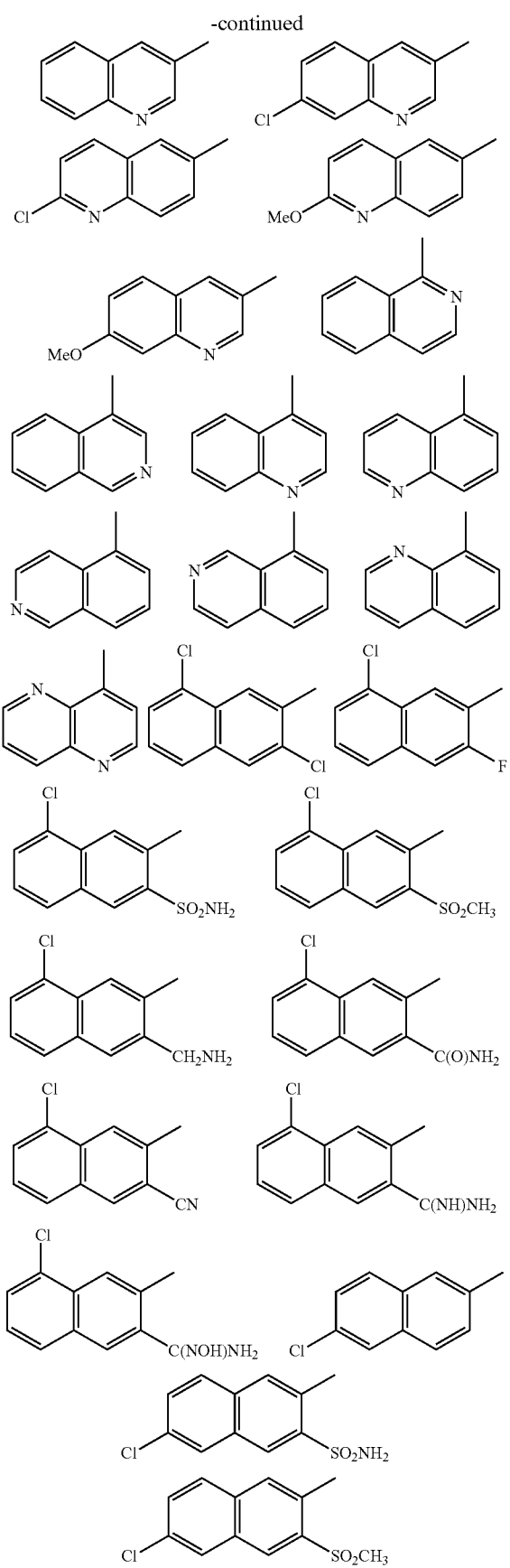
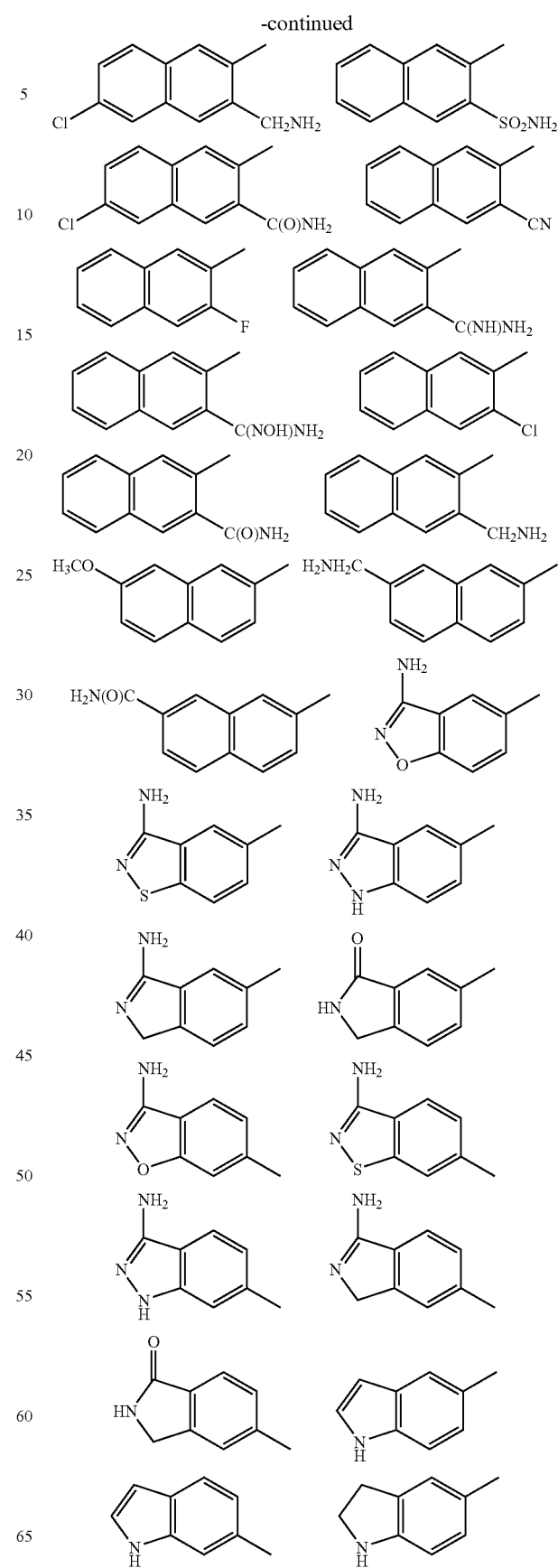

-continued
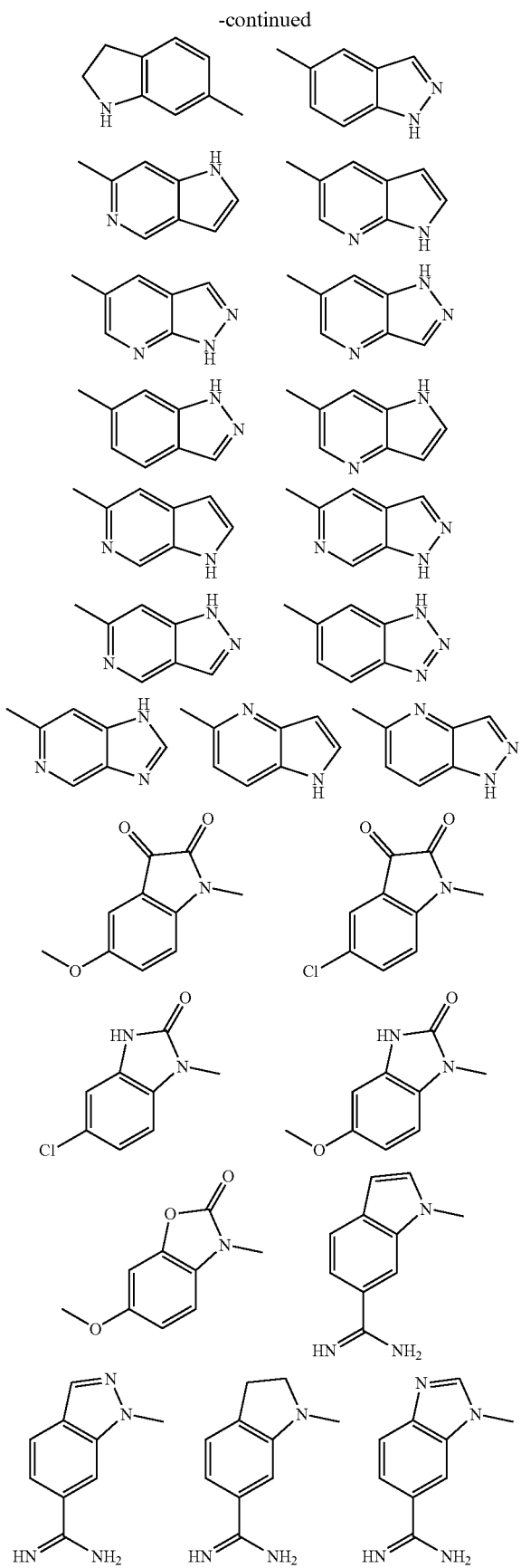
-continued
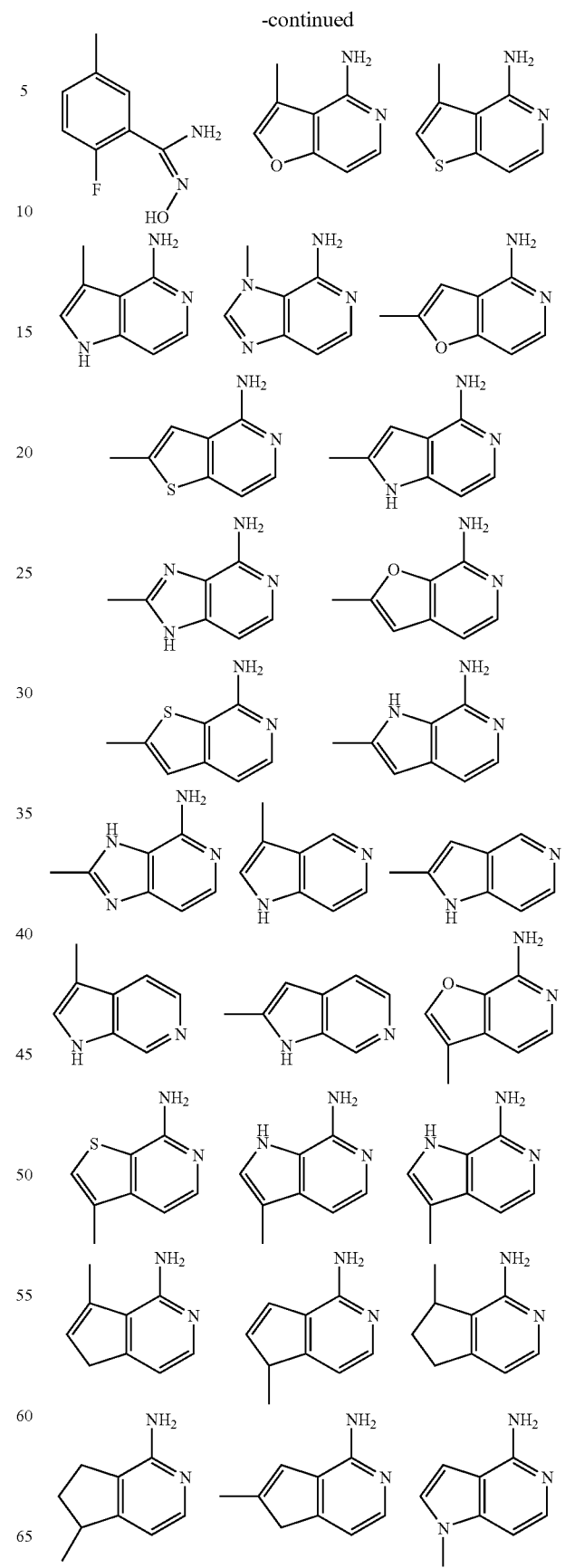

-continued
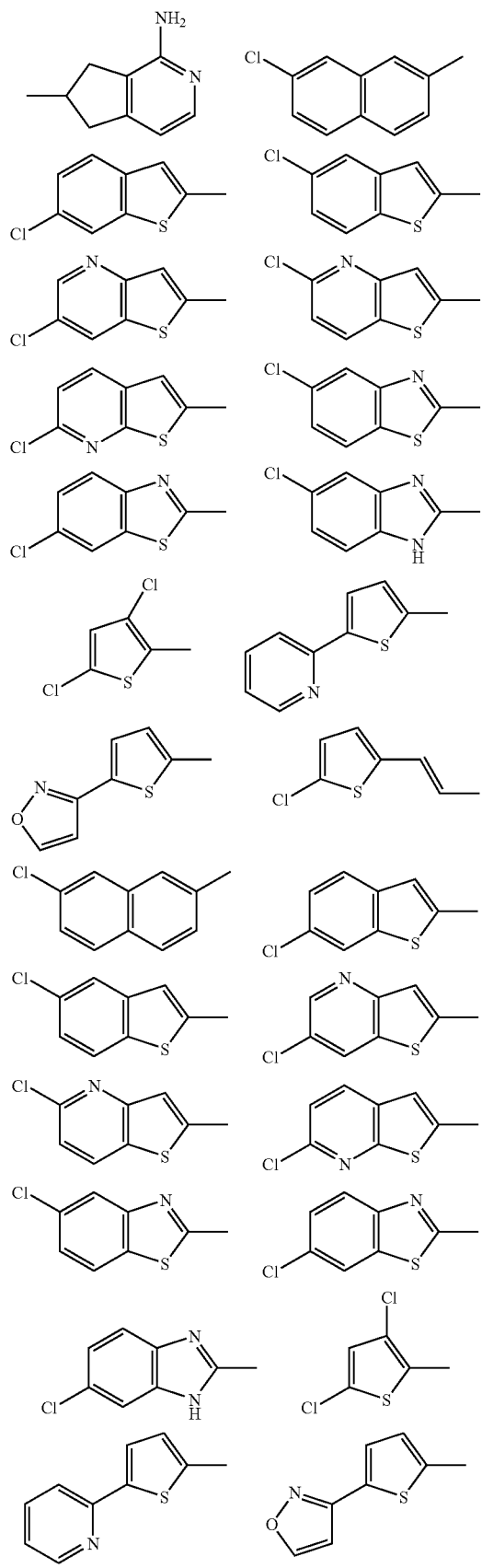
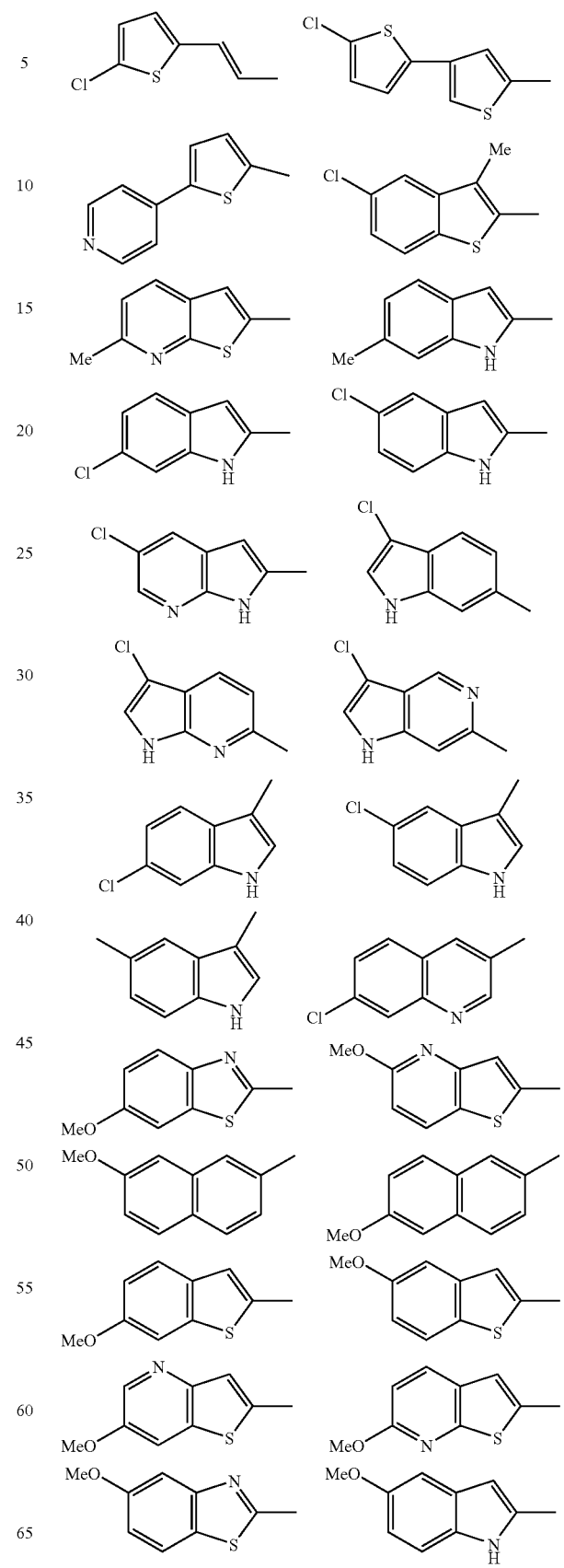

-continued

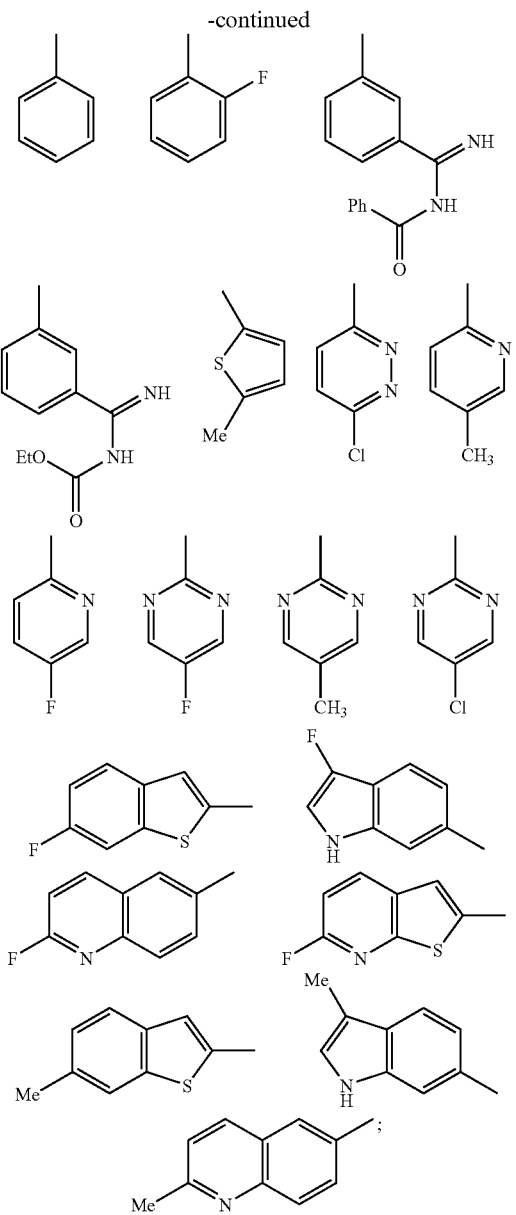

A is selected from one of the following carbocyclic and heterocyclic groups which are substituted with 0-2 $R^4$;

cyclohexyl, phenyl, piperazinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

$B^1$ is selected from H, $CH_3$, —$CH_2CH_3$, —$CH_2CH_2CH_3$, —$CH(CH_3)_2$, —$(CH_2)_{0-1}$—$C_{5-6}$ carbocycle substituted with 0-2 $R^{4b}$, and —$(CH_2)_{0-1}$-5-6 membered heterocycle consisting of: carbon atoms and 1-4 heteroatoms selected from N, O, and $S(O)_p$, and substituted with 0-2 $R^{4b}$;

$B^2$ is selected from H, $CH_3$, —$CH_2CH_3$, —$CH_2CH_2CH_3$, —$CH(CH_3)_2$, —$C(O)R^{2e}$, —$C(O)NR^{2d}R^{2d}$, —$SO_2NR^{2d}R^{2d}$, and —$S(O)_pR^{5a}$;

$B^3$ is selected from H, $C_{1-6}$ alkyl substituted with 0-1 $R^{4c}$, —$(CH_2)_{0-1}$—$C_{3-6}$ carbocycle substituted with 0-1 $R^5$, and a —$(CH_2)_{0-1}$-5-6 membered heterocycle consisting of: carbon atoms and 1-4 heteroatoms selected from N, O, and $S(O)_p$, and substituted with 0-1 $R^5$;

$B^4$ is selected from —$SO_2R^{3b}$ and —$OR^2$;

$B^5$ is —$NR^2R^{2f}$;

ring Q is a 5-6 membered ring consisting of, in addition to the N—$CR^{4d}$=N group shown, carbon atoms and 0-2 heteroatoms selected from N, O, and $S(O)_p$, and the ring is substituted with an additional 0-2 $R^{4d}$;

ring $Q^3$ is selected from —$CY^1Y^2$, a $C_{3-6}$ monocyclic carbocycle, and 5-6 membered monocyclic heterocycle, wherein the carobocycle or heterocycle consists of carbon atoms and 0-2 heteroatoms selected from N, O, and $S(O)_p$, the carbocycle or heterocycle further comprises 0-1 double bonds and 0-1 carbonyl groups, and the carbocycle or heterocycle is substituted with 0-2 $R^4$;

X is absent or is selected from —$(CR^2R^{2a})_{1-2}$—, —$C(O)$—, —$S(O)_2$—, —$S(O)_2NR^2$—, —$NR^2S(O)_2$—, —$NR^2C(O)$—, —$C(O)NR^2$—, $NR^2$, —$NR^2CR^2R^{2a}$—, —$CR^2R^{2a}NR^2$, O, —$OCR^2R^{2a}$—, and —$CR^2R^{2a}O$—;

$Y^1$ and $Y^2$ are independently $C_{1-2}$ alkyl substituted with 0-1 $R^4$;

$R^{1a}$ is, independently at each occurrence, selected from H, —$(CH_2)_rR^{1b}$, —$(CH_2)_r$—O—$(CH_2)_r$—$R^{1b}$, —$(CH_2)_r$—$C(=NR^{1b})NR^3R^{1b}$, —$NR^3(CR^3R^{3a})_rR^{1c}$, —$O(CR^3R^{3a})_tR^{1c}$, —$(CH_2)_rNR^3(CH_2)_rR^{1b}$, —$(CH_2)_rC(O)NR^2(CH_2)_rR^{1b}$, —$CO_2(CH_2)_rR^{1b}$, —$O(CH_2)_rR^{1b}$, —$S(O)_p(CH_2)_rR^{1d}$, —$O(CH_2)_rR^{1d}$, —$NR^3(CH_2)_rR^{1d}$, —$OC(O)NR^3(CH_2)_rR^{1d}$, —$NR^3C(O)NR^3(CH_2)_rR^{1d}$, —$NR^3C(O)O(CH_2)_rR^{1d}$, and —$NR^3C(O)(CH_2)_rR^{1d}$, provided that $R^{1a}$ forms other than an N-halo, N—S, O—O, or N—CN bond;

alternatively, $CR^{1a}R^{1a}$ forms a $C_{3-6}$ carbocyclic or heterocyclic ring consisting of: carbon atoms and 0-4 heteroatoms selected from N, O, and $S(O)_p$, this ring being substituted with 0-2 $R^4$ and 0-3 ring double bonds;

$R^{1b}$ is, independently at each occurrence, selected from H, $CH_3$, —$CH_2CH_3$, F, Cl, Br, CN, CHO, $CF_3$, —$(CH_2)_rOR^2$, —$NR^2R^{2a}$, —$C(O)R^{2b}$, —$CO_2R^{2b}$, —$OC(O)R^2$, —$CO_2R^{2a}$, —$S(O)_pR^2$, —$NR^2(CH_2)_rOR^2$, —$NR^2C(O)R^{2b}$, —$NR^2C(O)NR^2R^{2a}$, —$C(O)NR^2R^{2a}$, —$SO_2NR^2R^{2a}$, —$NR^2SO_2NR^2R^{2a}$, —$NR^2SO_2R^2$, —$C(O)NR^2SO_2R^2$, —$SO_2NR^2C(O)R^2$, $C_{3-10}$ carbocycle substituted with 0-2 $R^{4b}$, and 4-10 membered heterocycle consisting of carbon atoms and 1-4 heteroatoms selected from N, O, and $S(O)_p$, and substituted with 0-2 $R^{4b}$, provided that $R^{1b}$ forms other than an O—O, N-halo, N—S, or N—CN bond;

$R^2$ is, independently at each occurrence, selected from H, $CF_3$, $CH_3$, —$CH_2CH_3$, —$CH_2CH_2CH_3$, —$CH(CH_3)_2$, phenyl substituted with 0-2 $R^{4b}$, a benzyl substituted with 0-2 $R^{4b}$, and 5-6 membered aromatic heterocycle consisting of: carbon atoms and 1-4 heteroatoms selected from N, O, and $S(O)_p$, and substituted with 0-2 $R^{4b}$;

$R^{2a}$ is, independently at each occurrence, selected from H, $CF_3$, $CH_3$, —$CH_2CH_3$, —$CH_2CH_2CH_3$, —$CH(CH_3)_2$, benzyl, phenyl substituted with 0-2 $R^{4b}$, and 5-6 membered aromatic heterocycle consisting of: carbon atoms and 1-4 heteroatoms selected from N, O, and $S(O)_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from N, O, and $S(O)_p$;

$R^{2b}$ is, independently at each occurrence, selected from $CF_3$, $C_{1-4}$ alkoxy, $CH_3$, —$CH_2CH_3$, —$CH_2CH_2CH_3$, —$CH(CH_3)_2$, benzyl, phenyl substituted with 0-2 $R^{4b}$, and 5-6 membered aromatic heterocycle consisting of: carbon atoms and 1-4 heteroatoms selected from N, O, and $S(O)_p$, and substituted with 0-2 $R^{4b}$;

$R^{2c}$ is, independently at each occurrence, selected from $CF_3$, OH, —$OCH_3$, —$OCH_2CH_3$, —$OCH_2CH_2CH_3$, —$OCH(CH_3)_2$, $CH_3$, —$CH_2CH_3$, —$CH_2CH_2CH_3$, —$CH(CH_3)_2$, benzyl, phenyl substituted with 0-2 $R^{4b}$, and 5-6 membered aromatic heterocycle containing from 1-4 heteroatoms selected from N, O, and $S(O)_p$, and substituted with 0-2 $R^{4b}$;

$R^{2d}$ is, independently at each occurrence, selected from H, $R^{4c}$, $C_{1-4}$ alkyl substituted with 0-2 $R^{4c}$, $C_{3-6}$ carbocycle substituted with 0-2 $R^{4c}$, —$(CR^3R^{3a})$—$C_{3-6}$ carbocycle substituted with 0-2 $R^{4c}$, 5-6 membered heterocycle substituted with 0-2 $R^{4c}$ and consisting of: carbon atoms and 1-4 heteroatoms selected from N, O, and $S(O)_p$, and —$(CR^3R^{3a})$-5-6 membered heterocycle substituted with 0-2 $R^{4c}$ and consisting of: carbon atoms and 1-4 heteroatoms selected from N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5 or 6 membered saturated, partially saturated or unsaturated ring substituted with 0-2 $R^{4b}$ and consisting of: 0-1 additional heteroatoms selected from N, O, and $S(O)_p$;

$R^{2e}$ is, independently at each occurrence, selected from H, $R^{4c}$, $C_{1-4}$ alkyl substituted with 0-2 $R^{4c}$, $C_{3-6}$ carbocycle substituted with 0-2 $R^{4c}$, —$(CR^3R^{3a})$—$C_{3-6}$ carbocycle substituted with 0-2 $R^{4c}$, 5-6 membered heterocycle substituted with 0-2 $R^{4c}$ and consisting of: carbon atoms and 1-4 heteroatoms selected from N, O, and $S(O)_p$, and —$(CR^3R^{3a})$-5-6 membered heterocycle substituted with 0-2 $R^{4c}$ and consisting of: carbon atoms and 1-4 heteroatoms selected from N, O, and $S(O)_p$, provided that $R^{2e}$ forms other than a C(O)-halo or C(O)—$S(O)_p$ moiety;

$R^{2f}$ is, independently at each occurrence, selected from H, $CF_3$, $CH_3$, —$CH_2CH_3$, —$CH_2CH_2CH_3$, —$CH(CH_3)_2$, and benzyl;

alternatively, $NR^2R^{2f}$ forms a 5-6 membered ring consisting of: carbon atoms and 0-2 additional heteroatoms selected from N, O, and $S(O)_p$, and this ring is substituted with 0-2 $R^{4b}$;

alternatively, $B^4$ and $R^{2f}$ combine to form a 5-6 membered ring consisting of: carbon atoms and 0-1 additional heteroatoms selected from N, O, and $S(O)_p$, and this ring is substituted with 0-2 $R^{4b}$ and the $R^2$ group of $NR^2R^{2f}$, in addition to the groups recited below, can be $SO_2R^{3b}$;

$R^4$ is, independently at each occurrence, selected from H, =O, —$CH_2OR^2$, —$(CH_2)_2OR^2$, $OR^2$, F, Cl, Br, I, $CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, CN, $NO_2$, —$NR^2R^{2a}$, —$CH_2NR^2R^{2a}$, —$(CH_2)_2NR^2R^{2a}$, —$C(O)R^{2c}$, —$NR^2C(O)R^{2b}$, —$C(O)NR^2R^{2a}$, —$NR^2C(O)NR^2R^{2a}$, —$SO_2NR^2R^{2a}$, $CF_3$, and —$CF_2CF_3$;

$R^{4a}$ is selected from —$(CR^3R^{3g})_r$—$C_{5-6}$ carbocycle substituted with 0-3 $R^{4c}$, and —$(CR^3R^{3g})_r$-5-6 membered heterocycle substituted with 0-3 $R^{4c}$ and consisting of: carbon atoms and 1-4 heteroatoms selected from N, O, and $S(O)_p$;

alternatively, $R^{4a}$ is selected from —$(CR^3R^{3g})_r NR^{2d}R^{2d}$, —$(CR^3R^{3g})_r N(\rightarrow O)R^{2d}R^{2d}$, —$(CR^3R^{3g})_r OR^{2d}$, —$(CR^3R^{3g})_r NR^{2d}C(O)R^{2e}$, —$(CR^3R^{3g})_r C(O)R^{2e}$, —$(CR^3R^{3g})_r OC(O)R^{2e}$, —$(CR^3R^{3g})_r C(O)NR^{2d}R^{2d}$, —$(CR^3R^{3g})_r C(O)OR^{2d}$, —$(CR^3R^{3g})_r NR^{2d}C(O)NR^{2d}R^{2d}$, —$(CR^3R^{3g})_r NR^{2d}C(O)OR^{2d}$, —$(CR^3R^{3g})_r SO_2NR^{2d}R^{2d}$, —$(CR^3R^{3g})_r NR^{2d}SO_2R^{2d}$, and —$(CR^3R^{3g})_r S(O)_p R^{2d}$, provided that —$S(O)_p R^{2d}$ forms other than $S(O)_2H$ or $S(O)H$;

$R^{4b}$ is, independently at each occurrence, selected from H, =O, —$OR^3$, —$CH_2OR^3$, F, Cl, $CH_3$, —$CH_2CH_3$, —$CH_2CH_2CH_3$, —$CH(CH_3)_2$, CN, $NO_2$, —$NR^3R^{3a}$, —$CH_2NR^3R^{3a}$, —$C(O)R^3$, —$CH_2$—$C(O)R^3$, —$C(O)OR^{3c}$, —$CH_2C(O)OR^{3c}$, —$NR^3C(O)R^{3a}$, —$CH_2NR^3C(O)R^{3a}$, —$C(O)NR^3R^{3a}$, —$CH_2C(O)NR^3R^{3a}$, —$SO_2NR^3R^{3a}$, —$CH_2SO_2NR^3R^{3a}$, —$NR^3SO_2$—$C_{1-4}$ alkyl, —$CH_2NR^3SO_2C_{1-4}$ alkyl, —$NR^3SO_2$-phenyl, —$CH_2NR^3SO_2$-phenyl, —$S(O)_p CF_3$, —$CH_2S(O)_p CF_3$, —$S(O)_p$—$C_{1-4}$ alkyl, —$CH_2S(O)_p$—$C_{1-4}$ alkyl, —$S(O)_p$-phenyl, —$CH_2S(O)_p$-phenyl, and $CF_3$;

$R^{4c}$ is, independently at each occurrence, selected from =O, $OR^2$, —$(CR^3R^{3a})OR^2$, F, —$(CR^3R^{3a})F$, Br, —$(CR^3R^{3a})Br$, Cl, —$(CR^3R^{3a})Cl$, $CF_3$, —$(CR^3R^{3a})CF_3$, $C_{2-3}$ alkenyl, $C_{2-3}$ alkynyl, $C_{1-4}$ alkyl, CN, —$(CR^3R^{3a})CN$, $NO_2$, —$(CR^3R^{3a})NO_2$, —$NR^2R^{2a}$, —$(CR^3R^{3a})NR^2R^{2a}$, —$N(\rightarrow O)R^2R^{2a}$, —$(CR^3R^{3a})N(\rightarrow O)R^2R^{2a}$, —$C(O)R^{2c}$, —$(CR^3R^{3a})C(O)R^{2c}$, —$NR^2C(O)R^{2b}$, —$(CR^3R^{3a})NR^2C(O)R^{2b}$, —$C(O)NR^2R^{2a}$, —$(CR^3R^{3a})C(O)NR^2R^{2a}$, —$NR^2C(O)NR^2R^{2a}$, —$(CR^3R^{3a})NR^2C(O)NR^2R^{2a}$, —$SO_2NR^2R^{2a}$, —$(CR^3R^{3a})SO_2NR^2R^{2a}$, —$NR^2SO_2NR^2R^{2a}$, —$(CR^3R^{3a})NR^2SO_2NR^2R^{2a}$, —$NR^2SO_2R^{5a}$, —$(CR^3R^{3a})NR^2SO_2R^{5a}$, —$S(O)_p R^{5a}$, —$(CR^3R^{3a})S(O)_p R^{5a}$, $CF_3$, —$CF_2CF_3$, $C_{3-10}$ carbocycle substituted with 0-2 $R^{4b}$, —$(CR^3R^{3a})C_{3-10}$ carbocycle substituted with 0-2 $R^{4b}$, 5-10 membered heterocycle consisting of carbon atoms and 1-4 heteroatoms selected from N, O, and $S(O)_p$, and substituted with 0-2 $R^{4b}$, and —$(CR^3R^{3a})$-5-10 membered heterocycle consisting of carbon atoms and 1-4 heteroatoms selected from N, O, and $S(O)_p$, and substituted with 0-2 $R^{4b}$;

$R^{4d}$ is, independently at each occurrence, selected from H, $CH_2OR^2$, $OR^2$, $CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, CN, $NO_2$, —$CH_2NR^2R^{2a}$, —$NR^2R^{2a}$, —$C(O)R^{2c}$, —$NR^2C(O)R^{2b}$, —$C(O)NR^2R^{2a}$, —$NR^2C(O)NR^2R^{2a}$, —$NR^2SO_2R^5$, —$SO_2NR^2R^{2a}$, $C_6$ carbocycle substituted with 0-1 $R^5$, and a 5-6 membered heterocycle consisting of: carbon atoms and 1-2 heteroatoms selected from N, O, and $S(O)_p$, and substituted with 0-1 $R^5$;

$R^5$ is, independently at each occurrence, selected from H, =O, $CH_3$, —$CH_2CH_3$, —$CH_2CH_2CH_3$, —$CH(CH_3)_2$, —$OR^3$, —$CH_2OR^3$, F, Cl, CN, $NO_2$, —$NR^3R^{3a}$, —$CH_2NR^3R^{3a}$, —$C(O)R^3$, —$CH_2C(O)R^3$, —$C(O)OR^{3c}$, —$CH_2C(O)OR^{3c}$, —$NR^3C(O)R^{3a}$, —$C(O)NR^3R^{3a}$, —$SO_2NR^3R^{3a}$, —$NR^3SO_2$—$C_{1-4}$ alkyl, —$NR^3SO_2CF_3$, —$NR^3SO_2$-phenyl, —$S(O)_p CF_3$, —$S(O)_p$—$C_{1-4}$ alkyl, —$S(O)_p$-phenyl, $CF_3$, phenyl substituted with 0-2 $R^6$, naphthyl substituted with 0-2 $R^6$, and benzyl substituted with 0-2 $R^6$; and $R^6$ is, independently at each occurrence, selected from H, OH, —$OR^2$, F, Cl, $CH_3$, —$CH_2CH_3$, —$CH_2CH_2CH_3$, —$CH(CH_3)_2$, CN, $NO_2$, —$NR^2R^{2a}$, —$CH_2NR^2R^{2a}$, —$C(O)R^{2b}$, —$CH_2C(O)R^{2b}$, —$NR^2C(O)R^{2b}$, —$SO_2NR^2R^{2a}$, and —$NR^2SO_2C_{1-4}$ alkyl.

In another preferred embodiment, the present invention provides a novel compound, wherein the compound is selected from:

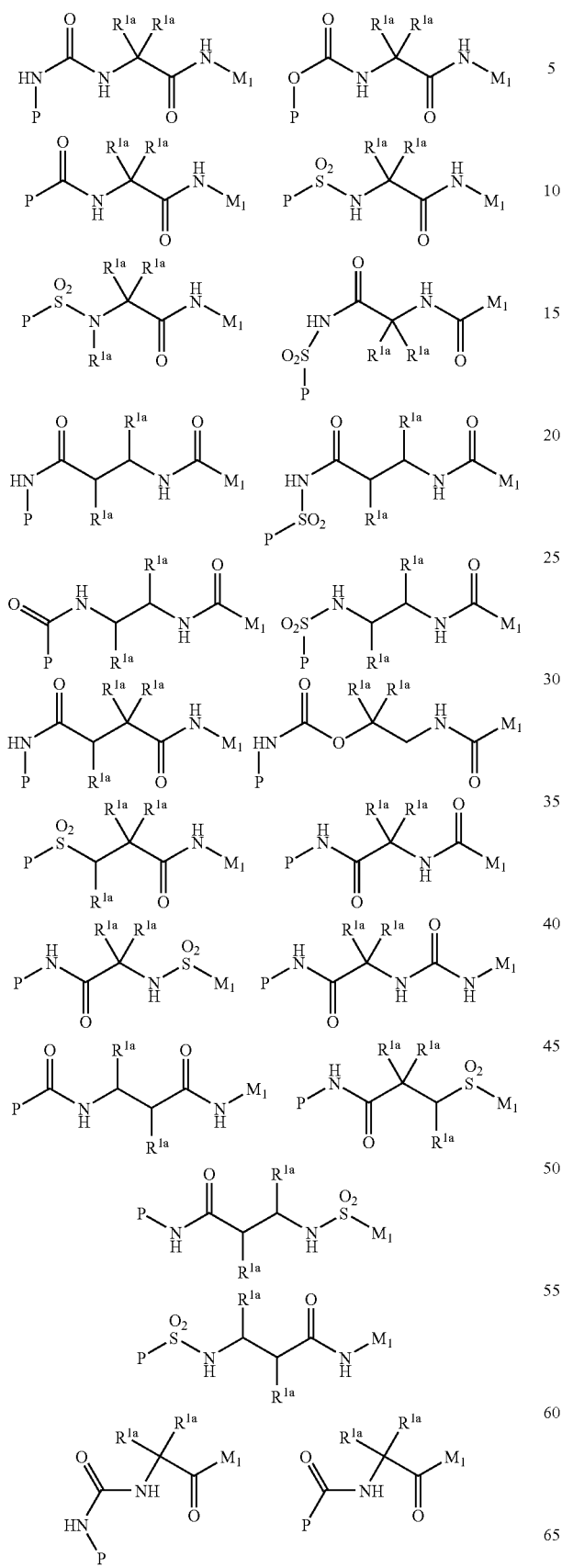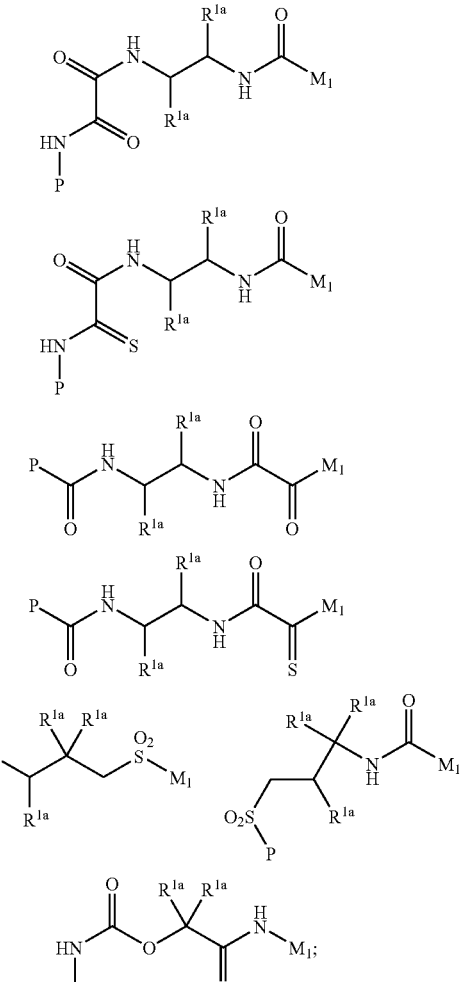
G is selected from the group:
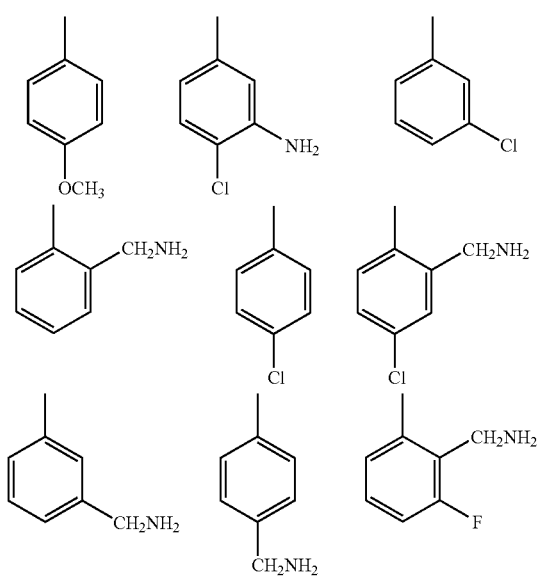

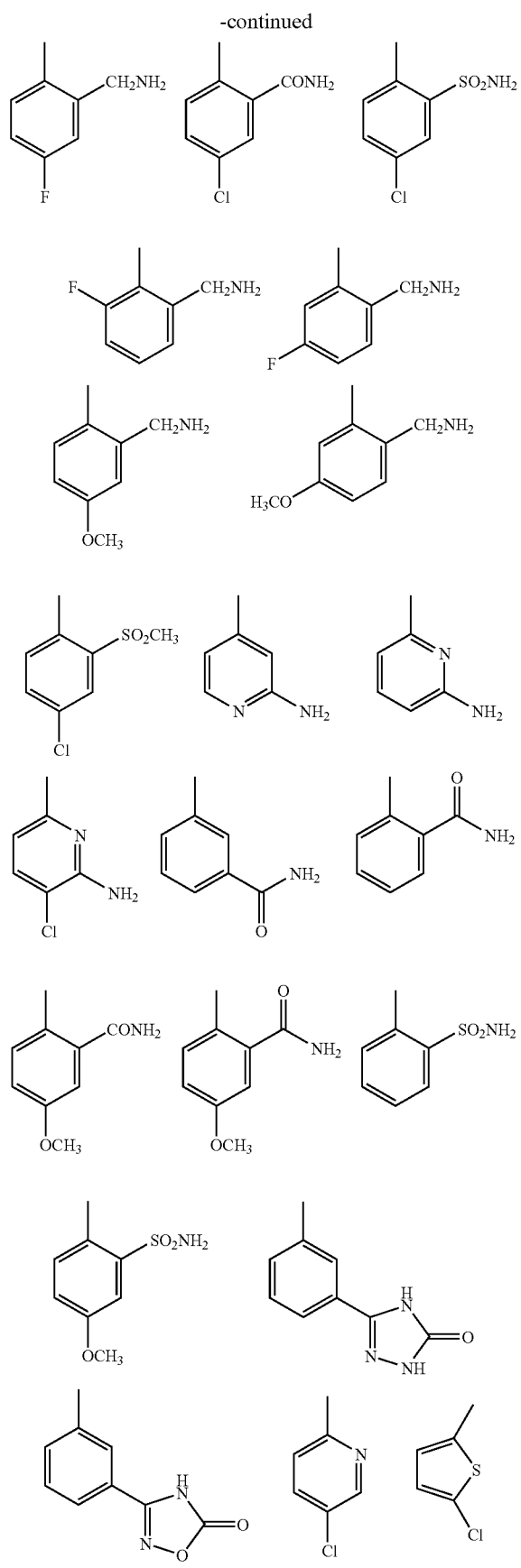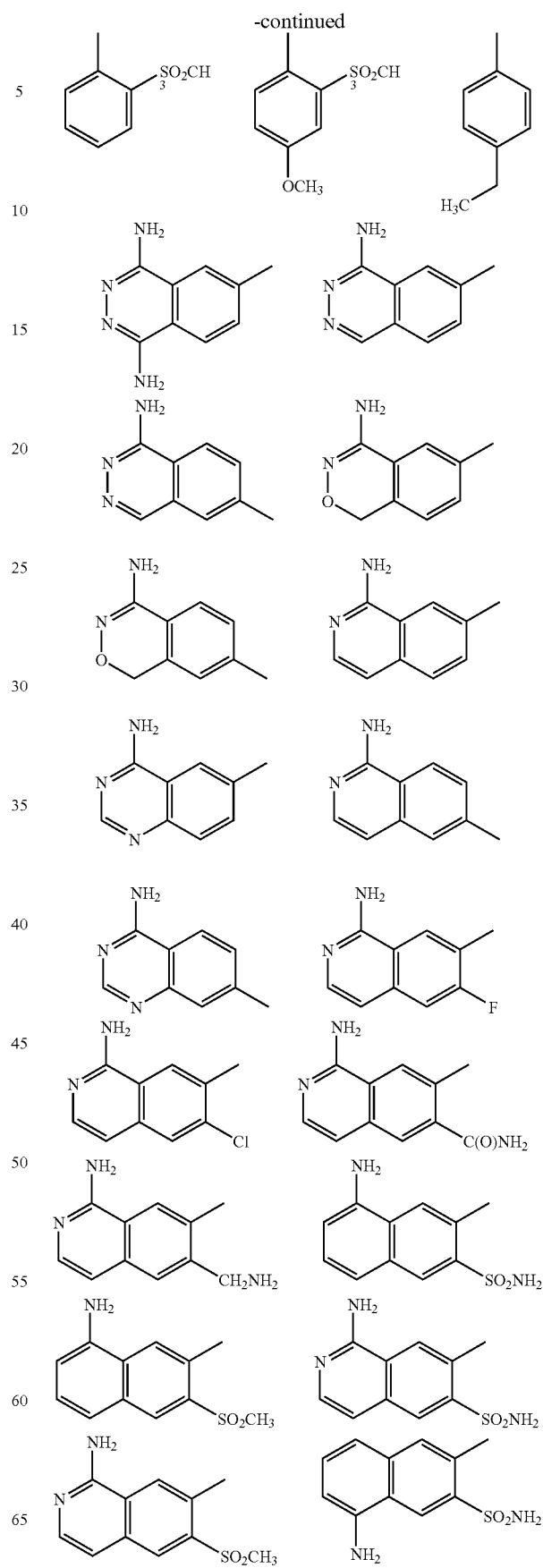

-continued
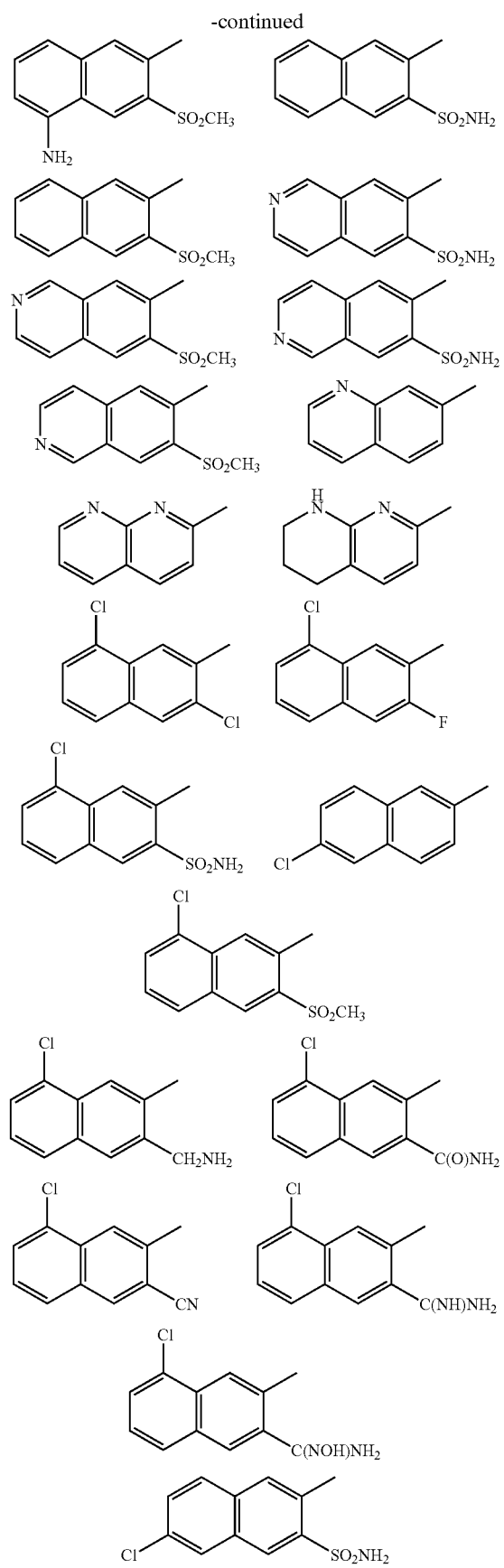
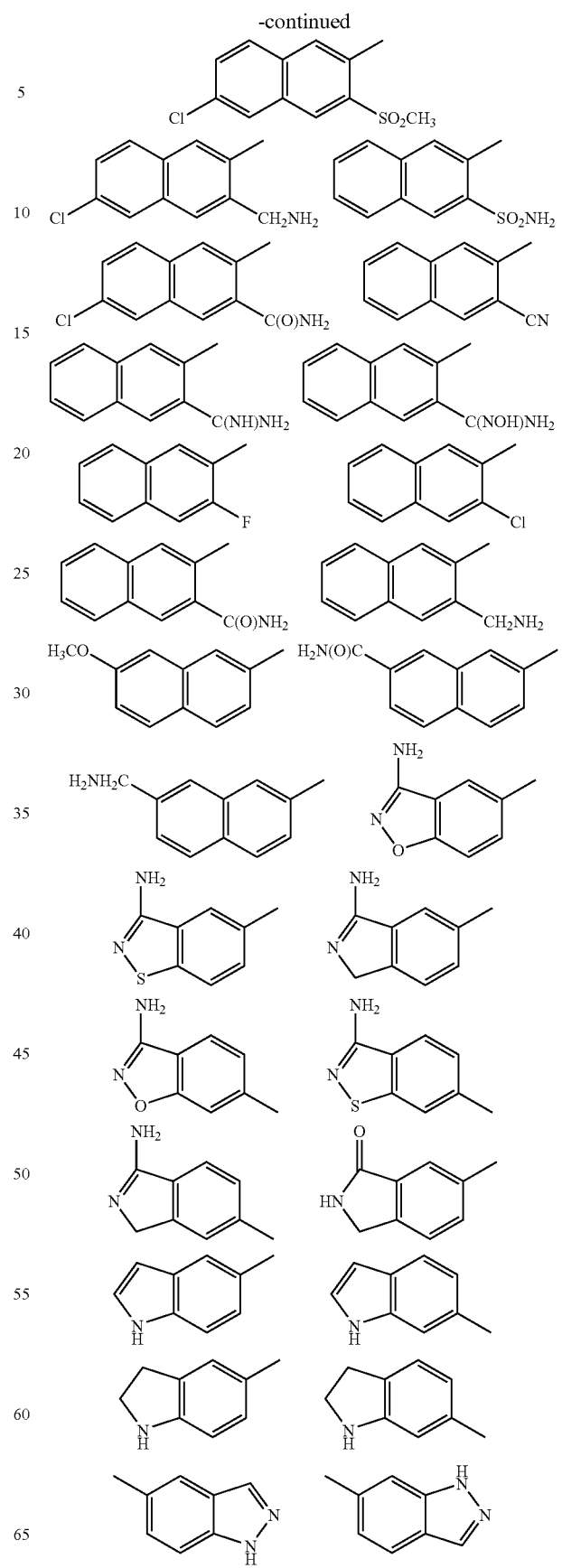

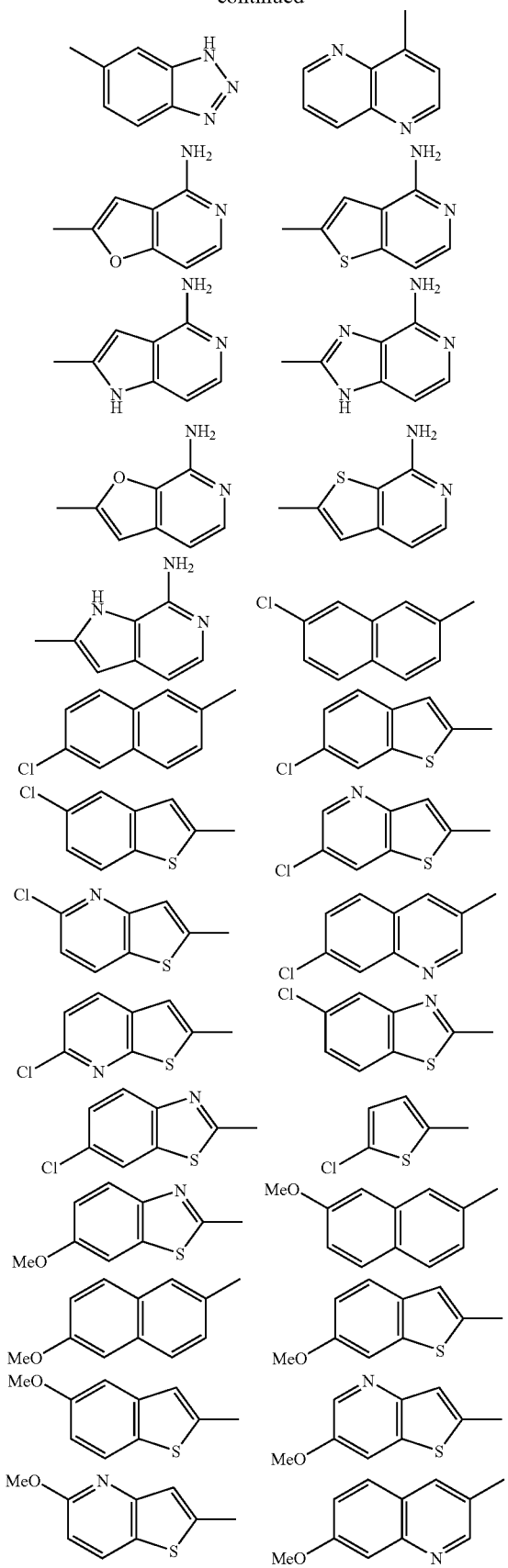
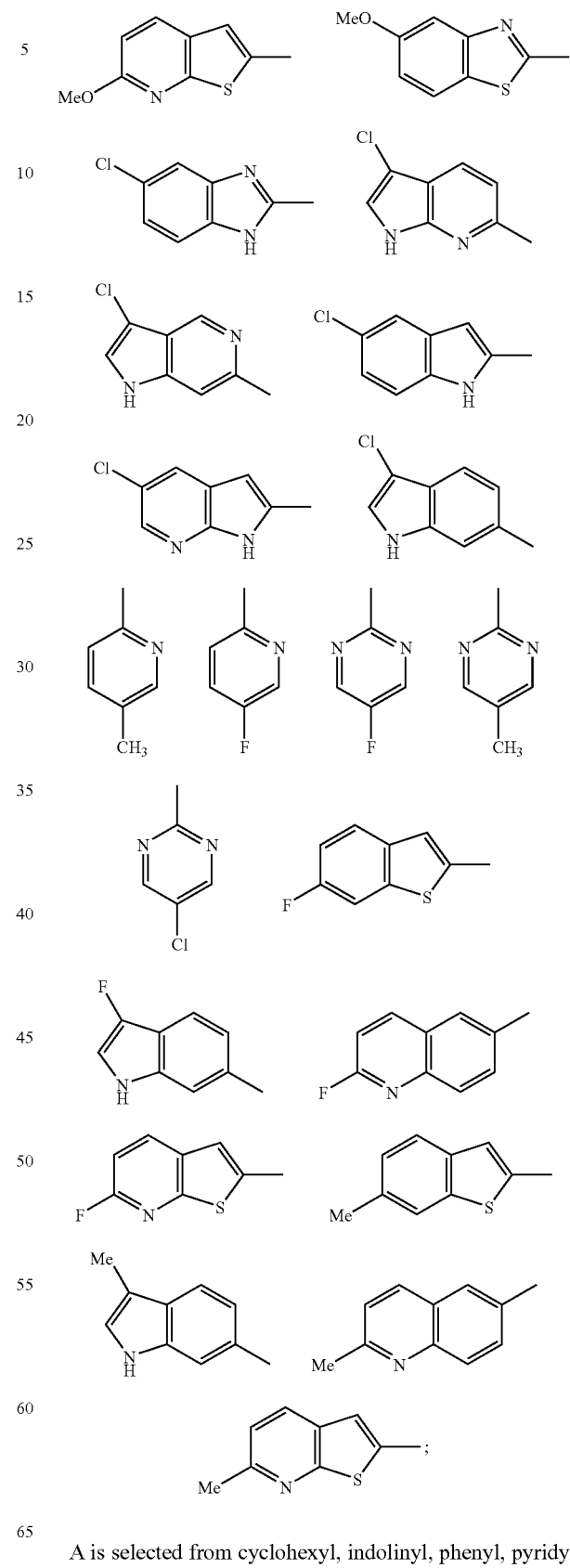
A is selected from cyclohexyl, indolinyl, phenyl, pyridyl, thienyl, and pyrimidyl, and is substituted with 0-2 $R^4$;

B is selected from —N(B$^1$)C(O)C(R$^3$R$^{3g}$)NB$^2$B$^3$,

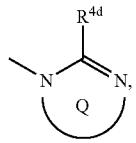

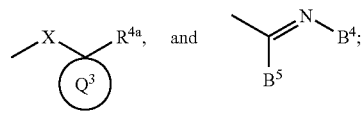

;provided that the R$^{4d}$ shown is other than OH and that M and B are attached to different atoms on A;

B$^1$ is selected from H, CH$_3$, —CH$_2$CH$_3$, —CH$_2$CH$_2$CH$_3$, and —CH(CH$_3$)$_2$;

B$^2$ is selected from H, CH$_3$, —CH$_2$CH$_3$, —CH$_2$CH$_2$CH$_3$, and —CH(CH$_3$)$_2$;

B$^3$ is selected from H, CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, C$_{2-5}$ alkyl substituted with 1 R$^{4c}$, —(CH$_2$)$_{0-1}$—C$_{3-6}$ carbocycle substituted with 0-1 R$^5$, and a —(CH$_2$)$_{0-1}$-5-6 membered heterocycle consisting of: carbon atoms and 1-4 heteroatoms selected from N, O, and S(O)$_p$, and substituted with 0-1 R$^5$;

B$^4$ is selected from —SO$_2$R$^{3b}$ and —OR$^2$;

B$^5$ is —NR$^2$R$^{2f}$;

ring Q is a 5-6 membered ring consisting of, in addition to the N—CR$^{4d}$═N group shown, carbon atoms and 0-1 heteroatoms selected from N, O, and S(O)$_p$, and the ring is substituted with an additional 0-2 R$^{4d}$;

ring Q$^3$ is selected from —C(CH$_3$)$_2$, —C(CH$_2$CH$_3$)$_2$, cyclopropyl, cyclobutyl, cyclopentyl, cyclopentanonyl, cyclohexyl, cyclohexanonyl, pyrrolidinyl, pyrrolidinonyl, piperadinyl, piperidonyl, tetrahydrofuranyl, and tetrahydropyranyl, and, when Y is a ring, Y is substituted with 0-1 R$^4$;

X is absent or is selected from CH$_2$, C(O), —S(O)$_2$—, —NHC(O)—, —C(O)NH—, —CH$_2$NH—, O, and —CH$_2$O—;

R$^{1a}$ is, independently at each occurrence, selected from H, R$^{1b}$, —C(CH$_3$)$_2$R$^{1b}$, —CH(CH$_3$)R$_{1b}$, —CH$_2$R$^{1b}$, —CH$_2$CH$_2$R$^{1b}$, —CH$_2$OCH$_2$CH$_2$R$^{1b}$, —OCH$_2$CH$_2$R$^{1b}$, —(CH$_2$)$_r$NR$^3$CH$_2$CH$_2$R$^{1b}$, —NR$^3$(CR$^3$R$^{3a}$)$_r$R$^{1c}$, —O(CR$^3$R$^{3a}$)$_r$R$^{1c}$, —(CH$_2$)$_r$C(O)NR$^2$(CH$_2$)$_r$R$^{1b}$, —S(O)$_p$(CH$_2$)$_r$R$^{1d}$, —O(CH$_2$)$_r$R$^{1d}$, —NR$^3$(CH$_2$)$_r$R$^{1d}$, —OC(O)NR$^3$(CH$_2$)$_r$R$^{1d}$, —NR$^3$C(O)NR$^3$(CH$_2$)$_r$R$^{1d}$, —NR$^3$C(O)O(CH$_2$)$_r$R$^{1d}$, and —NR$^3$C(O)(CH$_2$)$_r$R$^{1d}$, provided that R$^{1a}$ forms other than an N-halo, N—S, O—O, or N—CN bond;

alternatively, CR$^{1a}$R$^{1a}$ forms a C$_{3-10}$ carbocyclic or heterocyclic ring consisting of: carbon atoms and 0-4 heteroatoms selected from N, O, and S(O)$_p$, this ring being substituted with 0-2 R$^4$ and 0-2 ring double bonds;

R$^{1b}$ is, independently at each occurrence, selected from H, CH$_3$, —CH$_2$CH$_3$, F, Cl, Br, CN, CHO, CF$_3$, —(CH$_2$)$_r$OR$^2$, —NR$^2$R$^{2a}$, —C(O)R$^{2b}$, —CO$_2$R$^{2b}$, —OC(O)R$^2$, —CO$_2$R$^{2a}$, —S(O)$_p$R$^2$, —NR$^2$(CH$_2$)$_r$OR$^2$, —NR$^2$C(O)R$^{2b}$, —NR$^2$C(O)NR$^2$R$^{2a}$, —C(O)NR$^2$R$^{2a}$, —SO$_2$NR$^2$R$^{2a}$, —NR$^2$SO$_2$NR$^2$R$^{2a}$, —NR$^2$SO$_2$R$^2$, —C(O)NR$^2$SO$_2$R$^2$, —SO$_2$NR$^2$C(O)R$^2$, C$_{3-6}$ carbocycle substituted with 0-2 R$^4$, and 4-10 membered heterocycle consisting of carbon atoms and 1-4 heteroatoms selected from N, O, and S(O)$_p$, and substituted with 0-2 R$^4$, provided that R$^{1b}$ forms other than an O—O, N-halo, N—S, or N—CN bond;

R$^2$ is, independently at each occurrence, selected from H, CH$_3$, —CH$_2$CH$_3$, —CH$_2$CH$_2$CH$_3$, —CH(CH$_3$)$_2$, phenyl substituted with 0-1 R$^{4b}$, benzyl substituted with 0-1 R$^{4b}$, and 5-6 membered aromatic heterocycle consisting of: carbon atoms and 1-4 heteroatoms selected from N, O, and S(O)$_p$, and substituted with 0-1 R$^{4b}$;

R$^{2a}$ is, independently at each occurrence, selected from H, CH$_3$, —CH$_2$CH$_3$, —CH$_2$CH$_2$CH$_3$, —CH(CH$_3$)$_2$, benzyl, phenyl substituted with 0-1 R$^{4b}$, and 5-6 membered aromatic heterocycle consisting of: carbon atoms and 1-4 heteroatoms selected from N, O, and S(O)$_p$, and substituted with 0-1 R$^{4b}$;

alternatively, R$^2$ and R$^{2a}$, together with the atom to which they are attached, combine to form a 5 or 6 membered saturated, partially saturated or unsaturated ring substituted with 0-1 R$^{4b}$ and consisting of: 0-1 additional heteroatoms selected from N, O, and S(O)$_p$;

R$^{2b}$ is, independently at each occurrence, selected from —OCH$_3$, —OCH$_2$CH$_3$, —OCH$_2$CH$_2$CH$_3$, —OCH(CH$_3$)$_2$, CH$_3$, —CH$_2$CH$_3$, —CH$_2$CH$_2$CH$_3$, —CH(CH$_3$)$_2$, benzyl, phenyl substituted with 0-1 R$^{4b}$, and 5-6 membered aromatic heterocycle consisting of: carbon atoms and 1-4 heteroatoms selected from N, O, and S(O)$_p$, and substituted with 0-1 R$^{4b}$;

R$^{2c}$ is, independently at each occurrence, selected from OH, —OCH$_3$, —OCH$_2$CH$_3$, —OCH$_2$CH$_2$CH$_3$, —OCH(CH$_3$)$_2$, CH$_3$, —CH$_2$CH$_3$, —CH$_2$CH$_2$CH$_3$, —CH(CH$_3$)$_2$, benzyl, phenyl substituted with 0-1 R$^{4b}$, and 5-6 membered aromatic heterocycle containing from 1-4 heteroatoms selected from N, O, and S(O)$_p$, and substituted with 0-1 R$^{4b}$;

R$^{2d}$ is, independently at each occurrence, selected from H, R$^{4c}$, C$_{1-4}$ alkyl substituted with 0-2 R$^{4c}$, C$_{3-6}$ carbocycle substituted with 0-2 R$^{4c}$, —(CH$_2$)—C$_{3-6}$ carbocycle substituted with 0-2 R$^{4c}$, 5-6 membered heterocycle substituted with 0-2 R$^{4c}$ and consisting of: carbon atoms and 1-4 heteroatoms selected from N, O, and S(O)$_p$, and —(CH$_2$)-5-6 membered heterocycle substituted with 0-2 R$^{4c}$ and consisting of: carbon atoms and 1-4 heteroatoms selected from N, O, and S(O)$_p$, provided that R$^{2d}$ forms other than a N-halo, N—C-halo, S(O)$_p$-halo, O-halo, N—S, S—N, S(O)p—S(O)$_p$, S—O, O—N, O—S, or O—O moiety;

alternatively, NR$^{2d}$R$^{2d}$ forms a 5 or 6 membered saturated, partially saturated, or unsaturated ring substituted with 0-1 R$^{4b}$ and consisting of: 0-1 additional heteroatoms selected from N, O, and S(O)$_p$;

R$^{2e}$ is, independently at each occurrence, selected from H, R$^{4c}$, C$_{1-4}$ alkyl substituted with 0-2 R$^{4c}$, C$_{3-6}$ carbocycle substituted with 0-2 R$^{4c}$, —(CH$_2$)—C$_{3-6}$ carbocycle substituted with 0-2 R$^{4c}$, 5-6 membered heterocycle substituted with 0-2 R$^{4c}$ and consisting of: carbon atoms and 1-4 heteroatoms selected from N, O, and S(O)$_p$, and —(CH$_2$)-5-6 membered heterocycle and consisting of: carbon atoms and 1-4 heteroatoms selected from N, O, and S(O)$_p$, provided that R$^{2e}$ forms other than a C(O)-halo or C(O)—S(O)$_p$ moiety;

R$^{2f}$ is, independently at each occurrence, selected from H, CH$_3$, —CH$_2$CH$_3$, and benzyl;

alternatively, NR$^2$R$^{2f}$ forms a 5-6 membered ring consisting of: carbon atoms and 0-1 additional heteroatoms selected from N, O, and S(O)$_p$, and this ring is substituted with 0-1 R$^{4b}$;

alternatively, B$^4$ and R$^{2f}$ combine to form a 5 membered ring consisting of: carbon atoms and 0-1 additional heteroatoms selected from N, O, and S(O)$_p$, and this ring is substituted with 0-2 R$^{4b}$ and the R$^2$ group of —NR$^2$R$^{2f}$, in addition to the groups recited below, can be —SO$_2$R$^{3b}$;

R$^{3b}$ is, independently at each occurrence, selected from H and CH$_3$;

R$^4$ is, independently at each occurrence, selected from H, =O, OH, —OR$^2$, —CH$_2$OR$^2$, —(CH$_2$)$_2$OR$^2$, F, Br, Cl, I, CH$_3$, —CH$_2$CH$_3$, —CH$_2$CH$_2$CH$_3$, —CH(CH$_3$)$_2$, —CH$_2$CH$_2$CH$_2$CH$_3$—CH$_2$CH(CH$_3$)$_2$, —CH(CH$_3$) CH$_2$CH$_3$, —C(CH$_3$)$_3$, —NR$^2$R$^{2a}$, —CH$_2$NR$^2$R$^{2a}$, —(CH$_2$)$_2$ NR$^2$R$^{2a}$, —C(O)R$^{2c}$, —NR$^2$C(O)R$^{2b}$, —C(O)NR$^2$R$^{2a}$, —SO$_2$NR$^2$R$^{2a}$, CF$_3$, and —CF$_2$CF$_3$;

R$^{4a}$ is selected from —(CR$^3$R$^{3g}$)$_r$—C$_{5-6}$ carbocycle substituted with 0-3 R$^{4c}$, and —(CR$^3$R$^{3g}$)$_r$-5-6 membered heterocycle substituted with 0-3 R$^{4c}$ and consisting of: carbon atoms and 1-4 heteroatoms selected from N, O, and S(O)$_p$;

alternatively, R$^{4a}$ is selected from —(CR$^3$R$^{3g}$)$_r$NR$^{2d}$R$^{2d}$, —(CR$^3$R$^{3g}$)$_r$N(→O)R$^{2d}$R$^{2d}$, —(CR$^3$R$^{3g}$)$_r$OR$^{2d}$, —(CR$^3$R$^{3g}$)$_r$—C(O)NR$^{2d}$R$^{2d}$, —(CR$^3$R$^{3g}$)$_r$—NR$^{2d}$C(O) R$^{2e}$, —(CR$^3$R$^{3g}$)$_r$—C(O)R$^{2e}$, —(CR$^3$R$^{3g}$)$_r$—NR$^{2d}$C(O) NR$^{2d}$R$^{2d}$, —(CR$^3$R$^{3g}$)$_r$—NR$^{2d}$C(O)OR$^{2d}$, —(CR$^3$R$^{3g}$)$_r$—NR$^{2d}$SO$_2$R$^{2d}$, and —(CR$^3$R$^{3g}$)$_r$—S(O)$_p$R$^{2d}$, provided that —S(O)$_p$R$^{2d}$ forms other than —S(O)$_2$H or —S(O)H;

R$^{4b}$ is, independently at each occurrence, selected from H, =O, —OR$^3$, —CH$_2$OR$^3$, F, Cl, CH$_3$, —CH$_2$CH$_3$, —CH$_2$CH$_2$CH$_3$, —CH(CH$_3$)$_2$, CN, NO$_2$, —NR$^3$R$^{3a}$, —CH$_2$NR$^3$R$^{3a}$, —C(O)R$^3$, —C(O)OR$^{3c}$, —NR$^3$C(O)R$^{3a}$, —C(O)NR$^3$R$^{3a}$, —SO$_2$NR$^3$R$^{3a}$, —NR$^3$SO$_2$—C$_{1-4}$ alkyl, —NR$^3$SO$_2$-phenyl, —S(O)$_p$—C$_{1-4}$ alkyl, —S(O)$_p$-phenyl, and CF$_3$;

R$^{4c}$ is, independently at each occurrence, selected from =O, —OR$^2$, —CH$_2$OR$^2$, F, Br, Cl, CF$_3$, CH$_3$, —CH$_2$CH$_3$, —CH$_2$CH$_2$CH$_3$, —CH(CH$_3$)$_2$, —CH$_2$CH$_2$CH$_3$, —CH$_2$CH(CH$_3$)$_2$, —CH(CH$_3$)CH$_2$CH$_3$, —C(CH$_3$)$_3$, C$_{2-3}$ alkenyl, C$_{2-3}$ alkynyl, CN, NO$_2$, —NR$^2$R$^{2a}$, —CH$_2$NR$^2$R$^{2a}$, —N(→O)R$^2$R$^{2a}$, —CH$_2$N(→O)R$^2$R$^{2a}$, —C(O)R$^{2c}$, —CH$_2$C(O)R$^{2c}$, —NR$^2$C(O)R$^{2b}$, —CH$_2$NR$^2$C(O)R$^{2b}$, —C(O)NR$^2$R$^{2a}$, —CH$_2$C(O)NR$^2$R$^{2a}$, —SO$_2$NR$^2$R$^{2a}$, —CH$_2$SO$_2$NR$^2$R$^{2a}$, —NR$^2$SO$_2$R$^{5a}$, —CH$_2$NR$^2$SO$_2$R$^{5a}$, —S(O)$_p$R$^{5a}$, —CH$_2$S(O)$_p$R$^{5a}$, CF$_3$, —CF$_2$CF$_3$, C$_{3-6}$ carbocycle substituted with 0-2 R$^{4b}$, —(CH$_2$)C$_{3-6}$ carbocycle substituted with 0-2 R$^{4b}$, 5-6 membered heterocycle consisting of carbon atoms and 1-4 heteroatoms selected from N, O, and S(O)$_p$, and substituted with 0-2 R$^{4b}$, and —(CH$_2$)-5-6 membered heterocycle consisting of carbon atoms and 1-4 heteroatoms selected from N, O, and S(O)$_p$, and substituted with 0-2 R$^{4b}$;

R$^{4d}$ is, independently at each occurrence, selected from H, —CH$_2$OR$^2$, —OR$^2$, CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$NR$^2$R$^{2a}$, —NR$^2$R$^{2a}$, —C(O)R$^{2c}$, —NR$^2$C(O)R$^{2b}$, —C(O)NR$^2$R$^{2a}$, —SO$_2$NR$^2$R$^{2a}$, —NR$^2$SO$_2$R$^5$, phenyl substituted with 0-1 R$^5$, and a 5-6 membered heterocycle consisting of: carbon atoms and 1 heteroatom selected from N, O, and S(O)$_p$, and substituted with 0-1 R$^5$;

R$^5$ is, independently at each occurrence, selected from H, =O, CH$_3$, —CH$_2$CH$_3$, —CH$_2$CH$_2$CH$_3$, —CH(CH$_3$)$_2$, —OR$^3$, —CH$_2$OR$^3$, F, Cl, CN, NO$_2$, —NR$^3$R$^{3a}$, —CH$_2$NR$^3$R$^{3a}$, —C(O)R$^3$, —C(O)OR$^{3c}$, —NR$^3$C(O)R$^{3a}$, —C(O)NR$^3$R$^{3a}$, —SO$_2$NR$^3$R$^{3a}$, —NR$^3$SO$_2$—C$_{1-4}$ alkyl, —NR$^3$SO$_2$-phenyl, —S(O)$_p$—C$_{1-4}$ alkyl, —S(O)$_p$-phenyl, CF$_3$, phenyl substituted with 0-2 R$^6$, naphthyl substituted with 0-2 R$^6$, and benzyl substituted with 0-2 R$^6$; and R$^6$ is, independently at each occurrence, selected from H, OH, —OR$^2$, F, Cl, CH$_3$, —CH$_2$CH$_3$, —CH$_2$CH$_2$CH$_3$, —CH(CH$_3$)$_2$, CN, NO$_2$, —NR$^2$R$^{2a}$, —CH$_2$NR$^2$R$^{2a}$, —C(O)R$^{2b}$, —CH$_2$C(O)R$^{2b}$, —NR$^2$C(O)R$^{2b}$, and —SO$_2$NR$^2$R$^{2a}$.

In another preferred embodiment, the present invention provides a novel compound, wherein the compound is selected from:

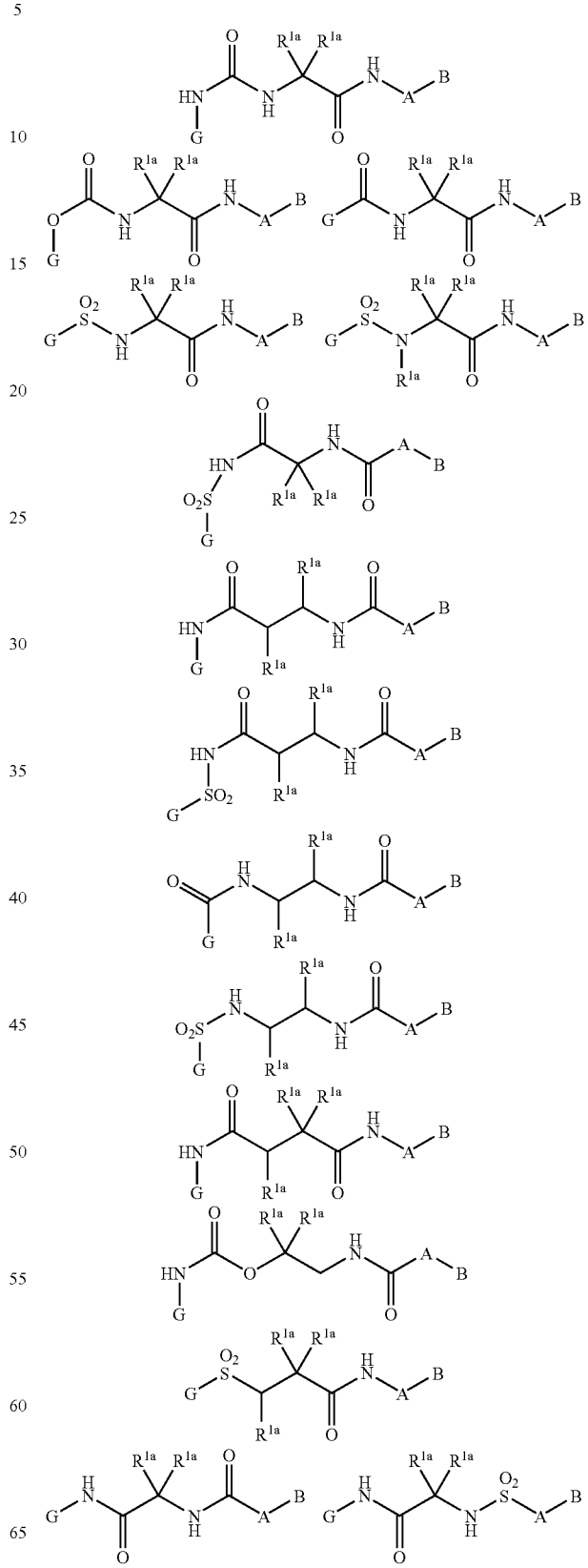

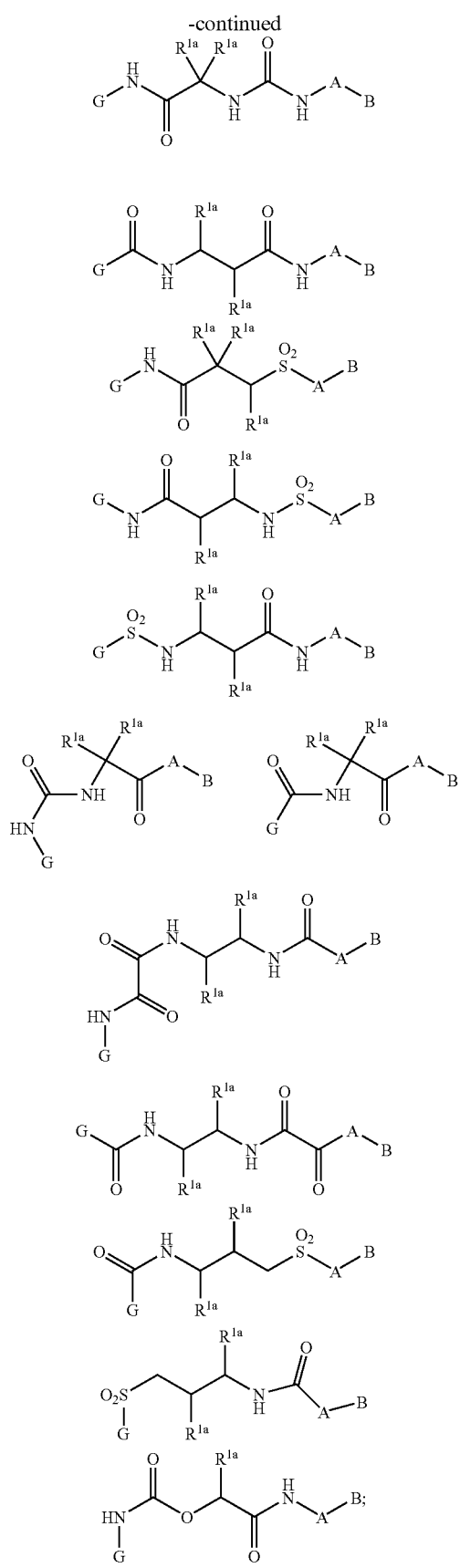
G is selected from:
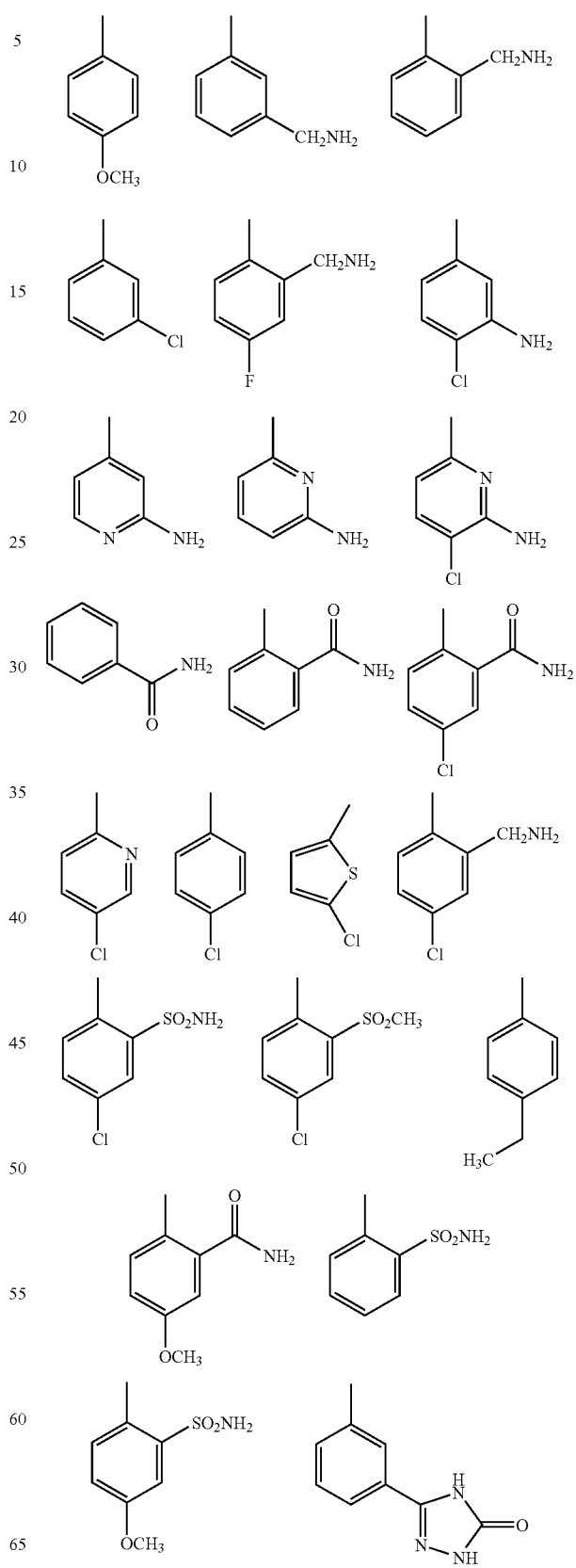

-continued
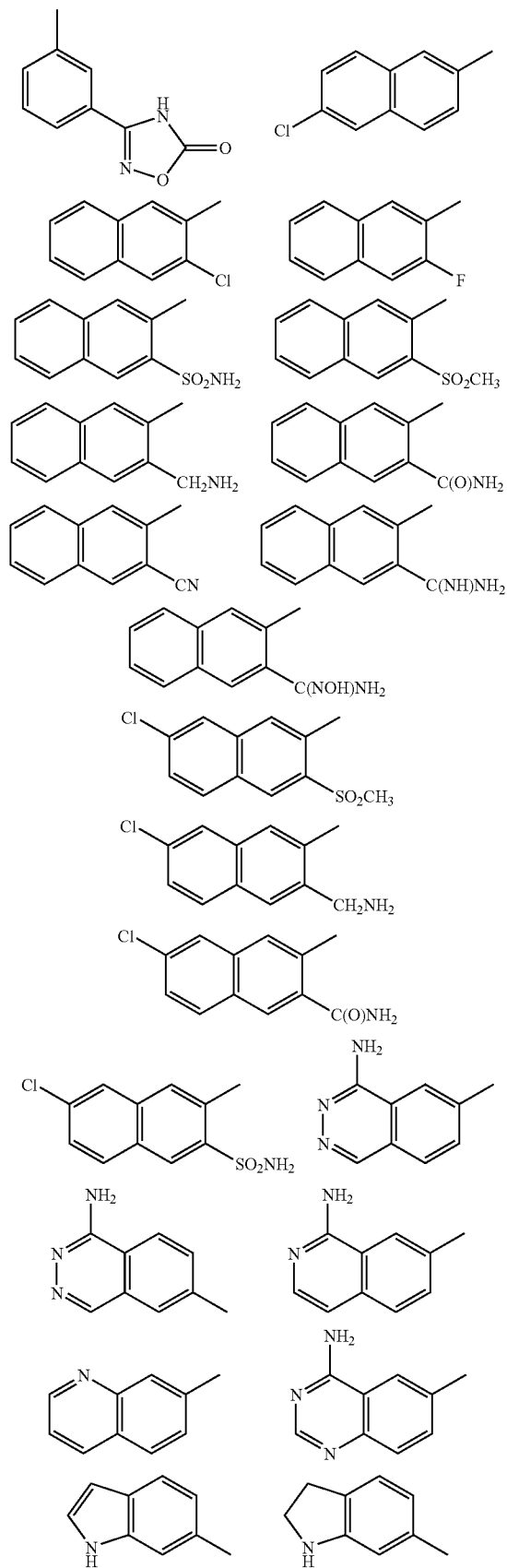
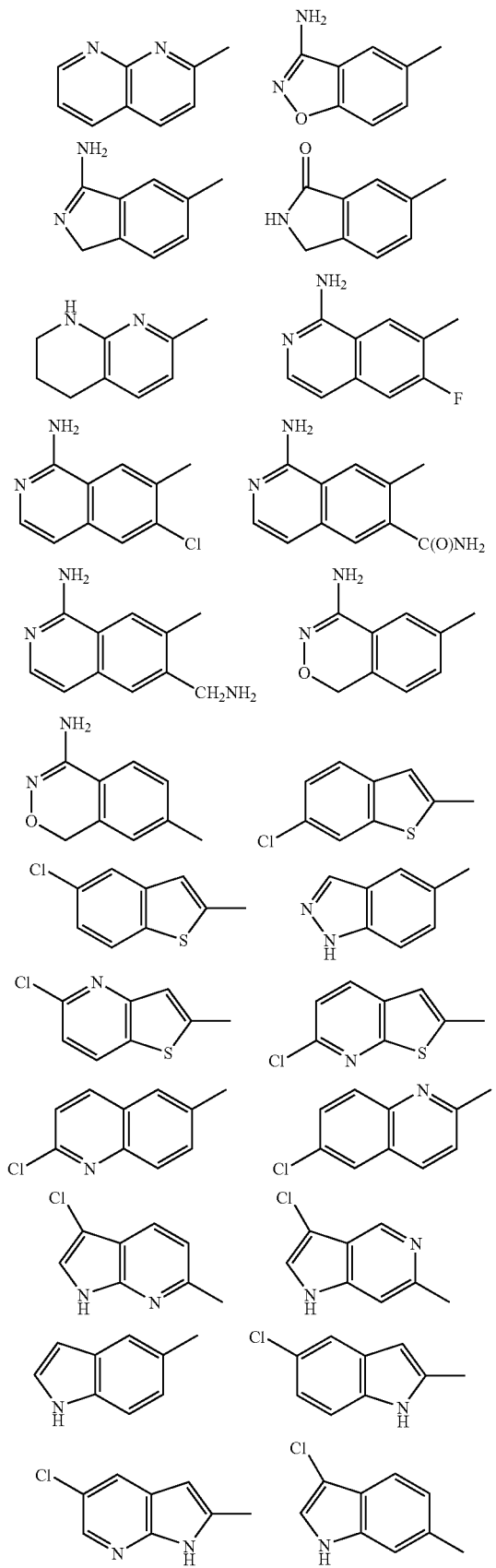

-continued

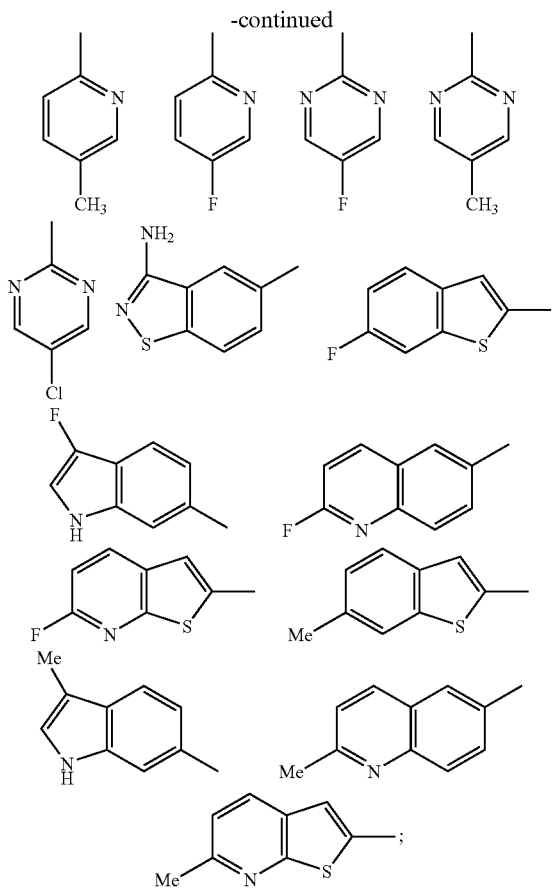

A is selected from the group: cyclohexyl, piperazinyl, indolinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from $-N(B^1)C(O)C(R^3R^{3g})NB^2B^3$,

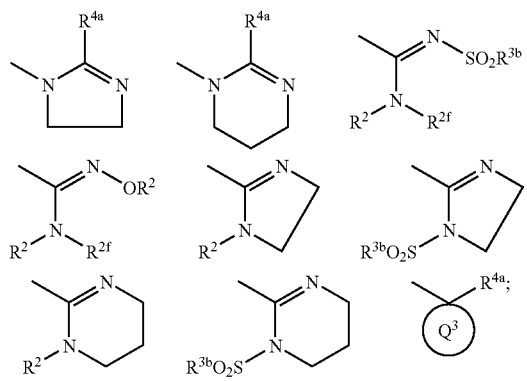

provided that the $R^{4d}$ shown is other than OH and that M and B are attached to different atoms on A;

$B^1$ is selected from H, $CH_3$, $-CH_2CH_3$, and $-CH_2CH_2CH_3$;

$B^2$ is selected from H, $CH_3$, and $-CH_2CH_3$;

$B^3$ is selected from $CH_3$, $-CH_2CH_3$, $-CH_2CH_2CH_3$, $-CH(CH_3)_2$, $-CH_2CH_2CH_2CH_3$, $-C(CH_3)_3$, $-CH$ $(CH_3)CH_2CH(CH_3)_2$, $-CH_2CH_2OH$, $-CH(CH_3)CH_2OH$, $-CH(phenyl)CH_2CH_3$, cyclopropyl, cyclobutyl, cyclopentyl, and $CH_2$-cyclopropyl;

ring $Q^3$ is selected from $-C(CH_3)_2$, $-C(CH_2CH_3)_2$, cyclopropyl, cyclobutyl, cyclopentyl, 2-cyclopentanonyl, cyclohexyl, 2-cyclohexanonyl, pyrrolidinyl (attached to A and $R^{4a}$ at the 2-position), pyrrolidinyl (attached to A and $R^{4a}$ at the 3-position), 2-pyrrolidinonyl (attached to A and $R^{4a}$ at the 3-position), piperazinyl (attached to A and $R^{4a}$ at the 4-position), 4-piperdinonyl (attached to A and $R^{4a}$ at the 3-position), tetrahydrofuranyl, and tetrahydropyranyl (attached to A and $R^{4a}$ at the 4-position);

$R^{1a}$ is, independently at each occurrence, selected from H, $CH_3$, $-CH_2CH_3$, $-CH_2CH_2CH_3$, $-CH_2(CH_3)_2$, $CF_3$, $-CH_2CF_3$, $-OCH_3$, $-CH_2OH$, $-C(CH_3)_2OH$, $-CH_2OCH_3$, $NH_2$, $-CH_2NH_2$, $-NHCH_3$, $-CH_2NHCH_3$, $-N(CH_3)_2$, $-CH_2N(CH_3)_2$, $-CO_2H$, $-COCH_3$, $-CO_2CH_3$, $-CH_2CO_2CH_3$, $-NHCOCH_3$, $-S(O)CH_3$, $-CH_2S(O)CH_3$, $-S(O)_2CH_3$, $-CH_2S(O)_2CH_3$, $-C(O)NH_2$, $-CH_2C(O)NH_2$, $-SO_2NH_2$, $-CH_2SO_2NH_2$, $-NHSO_2CH_3$, $-CH_2NHSO_2CH_3$, $-NHSO_2NHCH_3$, $-NHSO_2N(CH_3)_2$, $-NHCO_2R^{2a}$, $-NHC(O)NHR^{2a}$, $-CH_2OCH_2CH_2NR^2R^{2a}$, $-C(O)NR^2R^{2a}$, $-CH_2CH_2OR^2$, $-CH_2C(O)NR^2CH_2CH_2OR^2$, $-C(O)NHCH_2CH_2NR^2R^{2a}$, $-CH_2C(O)NHCH_2CH_2NR^2R^{2a}$, $-C(O)NCH_3CH_2CH_2NR^2R^{2a}$, $-CH_2C(O)NCH_3CH_2CH_2NR^2R^{2a}$, $-CH_2NHCH_2CH_2NR^2R^{2a}$, $-CH_2N(CH_3)CH_2CH_2NR^2R^{2a}$, phenyl substituted with 0-2 $R^{4b}$, $-CH_2$-phenyl substituted with 0-2 $R^{4b}$, 5-10 membered aromatic heterocycle consisting of carbon atoms and 1-4 heteroatoms selected from N, O, and $S(O)_p$, and substituted with 0-2 $R^{4b}$, and $-CH_2$-5-10 membered aromatic heterocycle consisting of carbon atoms and 1-4 heteroatoms selected from N, O, and $S(O)_p$, and substituted witlh 0-2 $R^{4b}$, provided that $R^{1a}$ forms other than an N-halo, N—S, O—O, or N—CN bond;

$R^2$ is, independently at each occurrence, selected from H, $CH_3$, $-CH_2CH_3$, $-CH_2CH_2CH_3$, $-CH(CH_3)_2$, phenyl substituted with 0-1 $R^{4b}$, benzyl substituted with 0-1 $R^{4b}$, and 5 membered aromatic heterocycle consisting of: carbon atoms and 1-4 heteroatoms selected from N, O, and $S(O)_p$, and substituted with 0-1 $R^{4b}$;

$R^{2a}$ is, independently at each occurrence, selected from H, $CH_3$, and $-CH_2CH_3$;

alternatively, $R^2$ and $R^{2a}$, together with the atom to which they are attached, combine to form a 5 or 6 membered saturated, partially saturated or unsaturated ring substituted with 0-1 $R^{4b}$ and consisting of: 0-1 additional heteroatoms selected from N, O, and $S(O)_p$;

$R^{2b}$ is, independently at each occurrence, selected from OH, $-OCH_3$, $-OCH_2CH_3$, $CH_3$, and $-CH_2CH_3$;

$R^{2c}$ is, independently at each occurrence, selected from OH, $-OCH_3$, $-OCH_2CH_3$, $CH_3$, and $-CH_2CH_3$;

$R^{2d}$ is, independently at each occurrence, selected from H, $R^{4c}$, $C_{1-4}$ alkyl substituted with 0-2 $R^{4c}$, $C_{3-6}$ cycloalkyl substituted with 0-2 $R^{4c}$, phenyl substituted with 0-2 $R^{4c}$, and 5-6 membered aromatic heterocycle substituted with 0-2 $R^{4c}$ and consisting of: carbon atoms and 1-4 heteroatoms selected from N, O, and $S(O)_p$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

alternatively, $NR^{2d}R^{2d}$ forms a 5 or 6 membered saturated, partially saturated, or unsaturated ring consisting of: 0-1 additional heteroatoms selected from N, O, and $S(O)_p$;

$R^{2e}$ is, independently at each occurrence, selected from H, $R^{4c}$, $C_{1-4}$ alkyl substituted with 0-2 $R^{4c}$, $C_{3-6}$ cycloalkyl substituted with 0-2 $R^{4c}$, phenyl substituted with 0-2 $R^{4c}$, and 5-6 membered aromatic heterocycle substituted with 0-2 $R^{4c}$ and consisting of: carbon atoms and 1-4 heteroatoms selected from N, O, and $S(O)_p$, provided that $R^{2e}$ forms other than a C(O)-halo or C(O)—$S(O)_p$ moiety;

$R^{2f}$ is, independently at each occurrence, selected from H, $CH_3$, and —$CH_2CH_3$;

alternatively, $NR^2R^{2f}$ forms a ring selected from morpholine, piperazine, piperidine, and pyrrolidine;

$R^4$ is, independently at each occurrence, selected from H, =O, $CH_3$, —$CH_2CH_3$, —$CH_2CH_2CH_3$, —$CH(CH_3)_2$, $CH_2CH_2CH_2CH_3$, $CH_2CH(CH_3)_2$, $CH(CH_3)CH_2CH_3$, and $C(CH_3)_3$;

$R^{4a}$ is selected from —$(CH_2)_r$—$C_{5-6}$ carbocycle substituted with 0-3 $R^{4c}$, and —$(CH_2)_r$-5-6 membered heterocycle substituted with 0-3 $R^{4c}$ and consisting of: carbon atoms and 1-4 heteroatoms selected from N, O, and $S(O)_p$;

alternatively, $R^{4a}$ is selected from —$(CH_2)_rNR^{2d}R^{2d}$, —$(CH_2)_rN(\rightarrow O)R^{2d}R^{2d}$, —$(CH_2)_rOR^{2d}$, —$(CH_2)_r$—C(O)$NR^{2d}R^{2d}$, —$(CH_2)_r$—$NR^{2d}C(O)R^{2e}$, —$(CH_2)_r$—$C(O)R^{2e}$, —$(CH_2)_r$—$NR^{2d}C(O)NR^{2d}R^{2d}$, —$(CH_2)_r$—$NR^{2d}C(O)OR^{2d}$, —$(CH_2)_r$—$NR^{2d}SO_2R^{2d}$, and —$(CH_2)_r$—$S(O)_pR^{2d}$, provided that —$S(O)_pR^{2d}$ forms other than —$S(O)_2H$ or —S(O)H;

$R^{4b}$ is, independently at each occurrence, selected from H, =O, —$OR^3$, —$CH_2OR^3$, F, Cl, $CH_3$, —$CH_2CH_3$, —$NR^3R^{3a}$, —$CH_2NR^3R^{3a}$, —$C(O)R^3$, —$C(O)OR^{3c}$, —$NR^3C(O)R^{3a}$, —$C(O)NR^3R^{3a}$, —$SO_2NR^3R^{3a}$, —$NR^3SO_2$-phenyl, —$S(O)_2CH_3$, —$S(O)_2$-phenyl, and $CF_3$;

$R^{4c}$ is, independently at each occurrence, selected from =O, OH, —$OCH_3$, —$OCH_2CH_3$, —$OCH_2CH_2CH_3$, —$OCH(CH_3)_2$, $CH_3$, —$CH_2CH_3$, —$CH_2CH_2CH_3$, —$CH(CH_3)_2$, $C_{2-3}$ alkenyl, $C_{2-3}$ alkynyl, —$CH_2OH$, —$CH_2OCH_3$, —$CH_2OCH_2CH_3$, —$CH_2OCH_2CH_2CH_3$, —$CH_2OCH(CH_3)_2$, F, Br, Cl, $CF_3$, —$NR^2R^{2a}$, —$CH_2NR^2R^{2a}$, —$N(\rightarrow O)R^2R^{2a}$, —$CH_2N(\rightarrow O)R^2R^{2a}$, —$C(O)R^{2c}$, —$CH_2C(O)R^{2c}$, —$NR^2C(O)R^{2b}$, —$CH_2NR^2C(O)R^{2b}$, —$C(O)NR^2R^{2a}$, —$CH_2C(O)NR^2R^{2a}$, —$SO_2NR^2R^{2a}$, —$CH_2SO_2NR^2R^{2a}$, —$NR^2SO_2R^{5a}$, —$CH_2NR^2SO_2R^{5a}$, —$S(O)_pR^{5a}$, —$CH_2S(O)_pR^{5a}$, $CF_3$, cyclopropyl substituted with 0-1 $R^{4b}$, cyclobutyl substituted with 0-1 $R^{4b}$, cyclopentyl substituted with 0-1 $R^{4b}$, phenyl substituted with 0-1 $R^{4b}$, —$CH_2$-cyclopropyl substituted with 0-1 $R^{4b}$, —$CH_2$-cyclobutyl substituted with 0-1 $R^{4b}$, —$CH_2$-cyclopentyl substituted with 0-1 $R^{4b}$, benzyl substituted with 0-2 $R^{4b}$, 5-6 membered aromatic heterocycle consisting of carbon atoms and 1-4 heteroatoms selected from N, O, and $S(O)_p$, and substituted with 0-2 $R^{4b}$, and —$(CH_2)$-5-6 membered aromatic heterocycle consisting of carbon atoms and 1-4 heteroatoms selected from N, O, and $S(O)_p$, and substituted with 0-2 $R^{4b}$;

$R^{4d}$ is, independently at each occurrence, selected from H, —$OCH_3$, $CH_3$, —$CH_2CH_3$, —$CH_2CH_2CH_3$, —$CH(CH_3)_2$, —$NR^2R^{2a}$, —$NR^2C(O)R^{2b}$, —$NR^2SO_2R^5$, phenyl, 2-oxo-pyrrolidinyl, and 2-oxo-piperazinyl;

$R^5$ is, independently at each occurrence, selected from H, =O, $CH_3$, —$CH_2CH_3$, —$OR^3$, —$CH_2OR^3$, F, Cl, —$NR^3R^{3a}$, —$CH_2NR^3R^{3a}$, —$C(O)R^3$, —$C(O)OR^{3c}$, —$NR^3C(O)R^{3a}$, —$C(O)NR^3R^{3a}$, —$SO_2NR^3R^{3a}$, —$NR^3SO_2$—$C_{1-4}$ alkyl, —$NR^3SO_2$-phenyl, —$S(O)_2$—$CH_3$, —$S(O)_2$-phenyl, $CF_3$, phenyl substituted with 0-2 $R^6$, naphthyl substituted with 0-2 $R^6$, and benzyl substituted with 0-2 $R^6$; and $R^6$ is, independently at each occurrence, selected from H, OH, —$OR^2$, F, Cl, $CH_3$, —$CH_2CH_3$, —$NR^2R^{2a}$, —$CH_2NR^2R^{2a}$, —$C(O)R^{2b}$, —$CH_2C(O)R^{2b}$, —$NR^2C(O)R^{2b}$, and —$SO_2NR^2R^{2a}$.

In another preferred embodiment, the present invention provides a novel compound, wherein the compound is selected from:

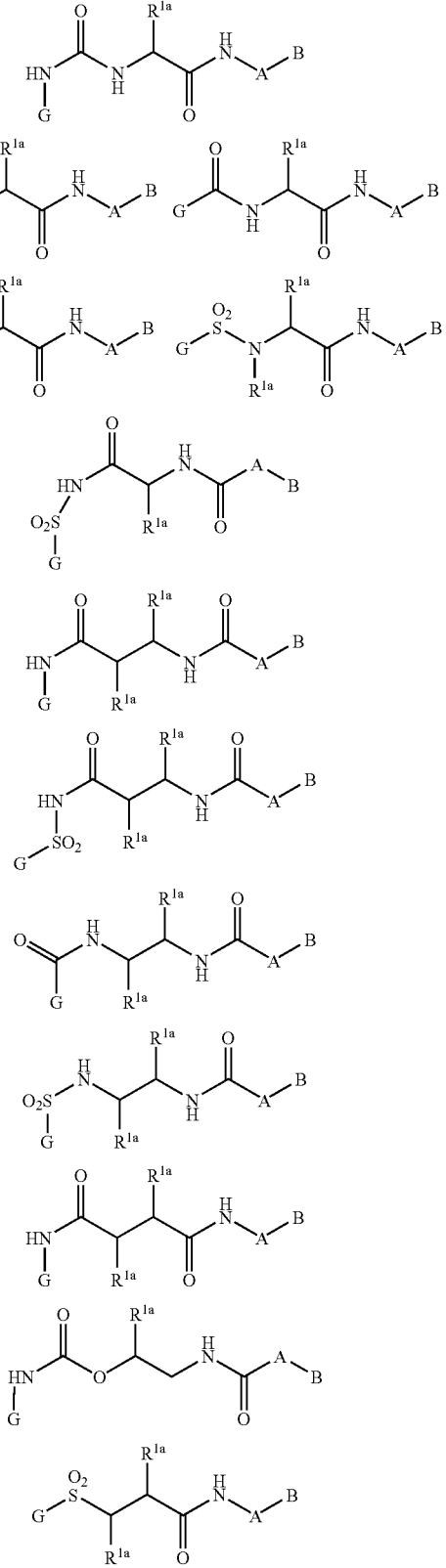

-continued
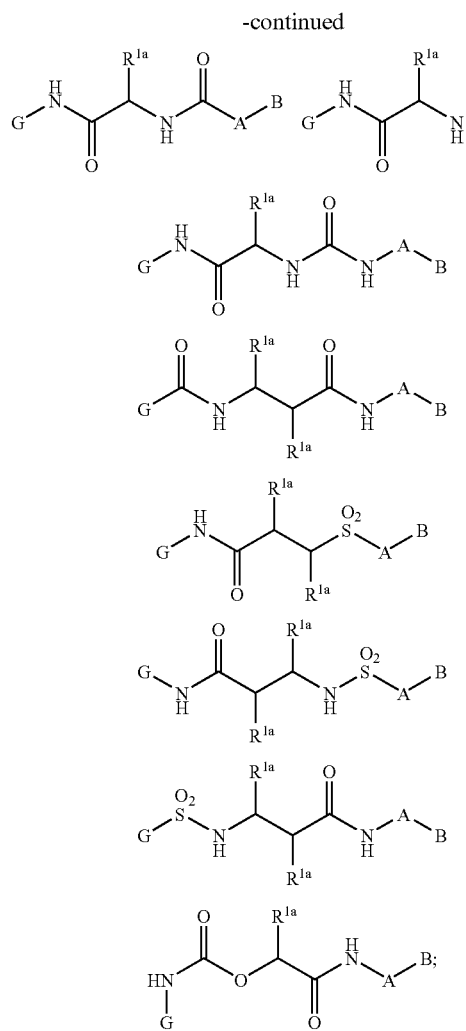
G is selected from:
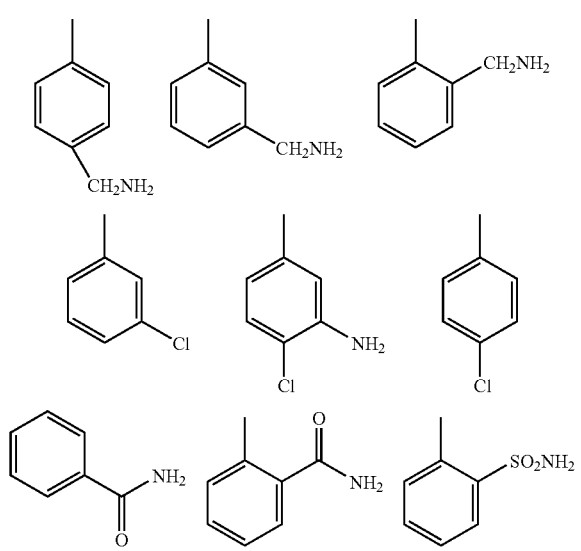
-continued
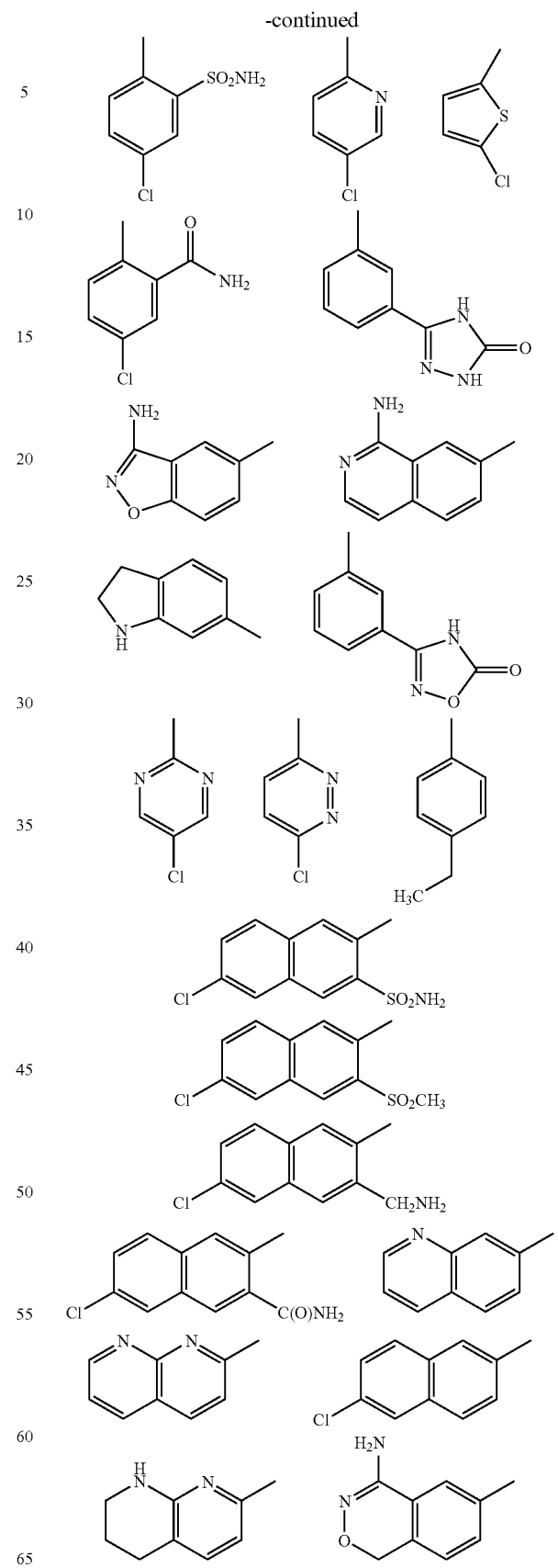

-continued
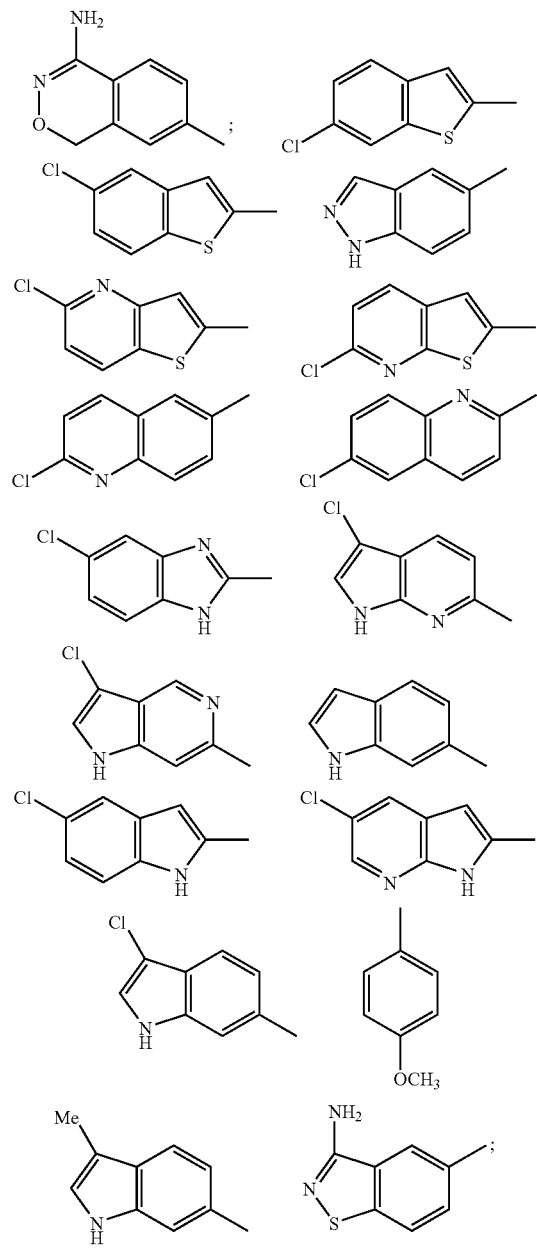
B is selected from:
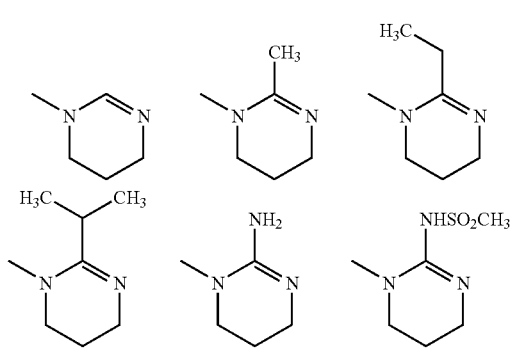
-continued
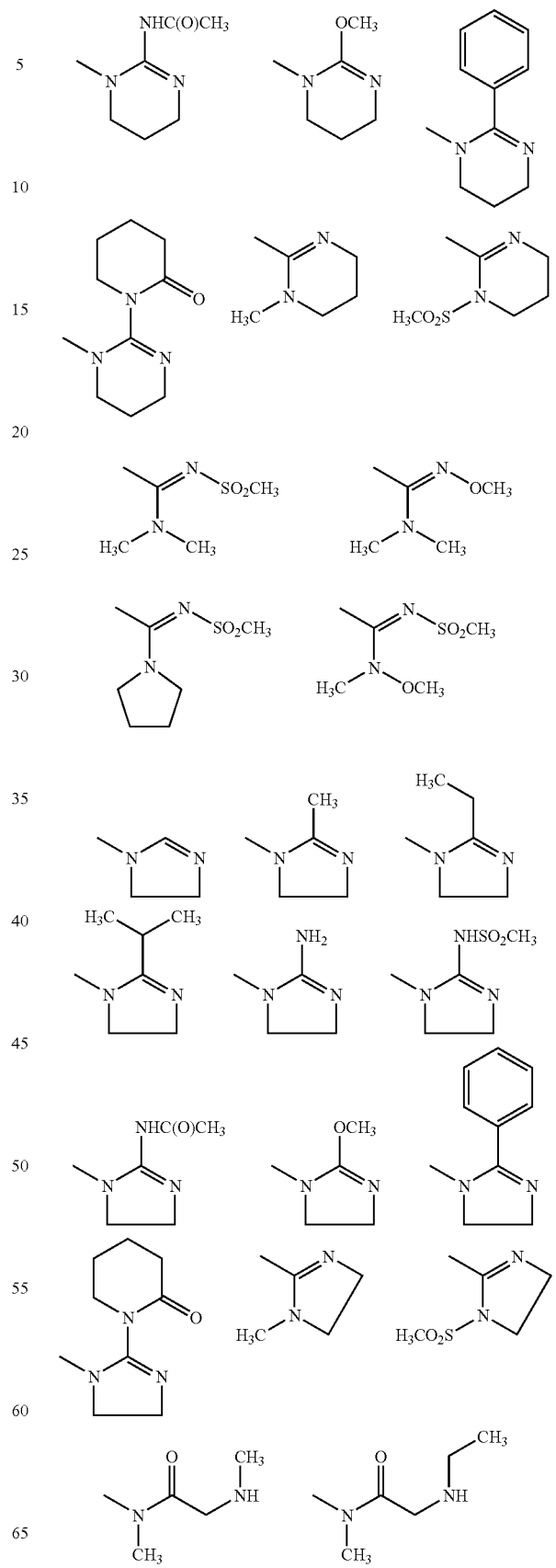

-continued

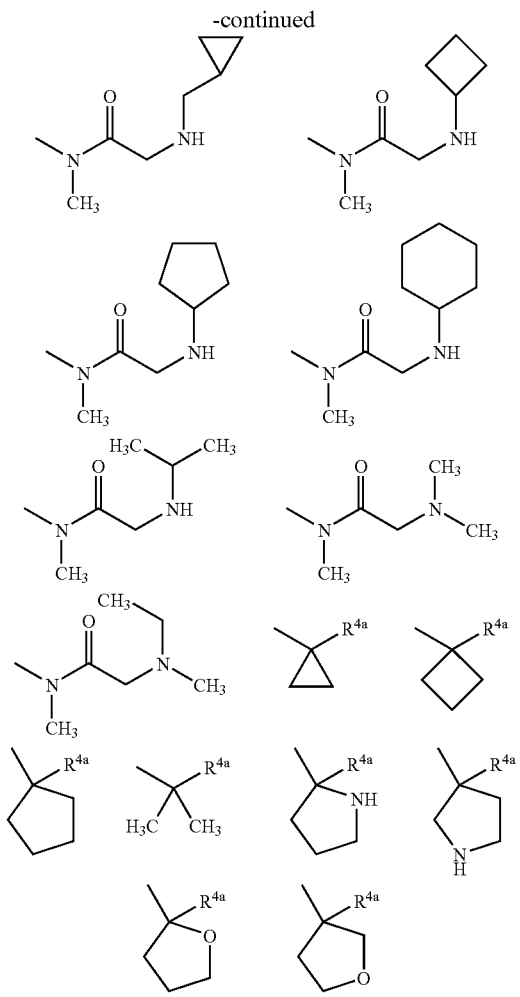

R$^{2d}$ is, independently at each occurrence, selected from H, C$_{1-4}$ alkyl substituted with 0-1 R$^{4c}$, C$_{3-6}$ cycloalkyl substituted with 0-2 R$^{4c}$, phenyl substituted with 0-2 R$^{4c}$, and a 5-6 membered aromatic heterocycle consisting of: carbon atoms and 1-4 heteroatoms selected from N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

alternatively, NR$^{2d}$R$^{2d}$ forms a 5 or 6 membered saturated or partially saturated ring consisting of: 0-1 additional heteroatoms selected from N, O, and S(O)$_p$;

R$^{2e}$ is, independently at each occurrence, selected from H, C$_{1-4}$ alkyl substituted with 0-1 R$^{4c}$, C$_{3-6}$ cycloalkyl substituted with 0-2 R$^{4c}$, phenyl, substituted with 0-2 R$^{4c}$, and 5-6 membered aromatic heterocycle consisting of: carbon atoms and 1-4 heteroatoms selected from N, O, and S(O)$_p$, provided that R$^{2e}$ forms other than a C(O)-halo or C(O)—S(O)$_p$ moiety;

R$^{4a}$ is selected from —NR$^{2d}$R$^{2d}$, —CH$_2$NR$^{2d}$R$^{2d}$, —N(→O)R$^{2d}$R$^{2d}$, —CH$_2$N(→O)R$^{2d}$R$^{2d}$, —CH$_2$OR$^{2d}$, —C(O)R$^{2e}$, —C(O)NR$^{2d}$R$^{2d}$, —CH$_2$C(O)NR$^{2d}$R$^{2d}$, —NR$^{2d}$C(O)R$^{2e}$, —CH$_2$NR$^{2d}$C(O)R$^{2e}$, —NR$^{2d}$C(O)NR$^{2d}$R$^{2d}$, —CH$_2$NR$^{2d}$C(O)NR$^{2d}$R$^{2d}$, —NR$^{2d}$C(O)OR$^{2d}$, —CH$_2$NR$^{2d}$C(O)OR$^{2d}$, —NR$^{2d}$SO$_2$R$^{2d}$, —CH$_2$NR$^{2d}$SO$_2$R$^{2d}$, —S(O)$_p$R$^{2d}$, —CH$_2$S(O)$_p$R$^{2d}$, —(CH$_2$)$_{0-1}$—C$_{5-6}$ carbocycle substituted with 0-2 R$^{4c}$, and —(CH$_2$)$_{0-1}$-5-6 membered heterocycle substituted with 0-2

R$^{4c}$ and consisting of: carbon atoms and 1-4 heteroatoms selected from N, O, and S(O)$_p$, provided that —S(O)$_p$R$^{2d}$ forms other than —S(O)$_2$H or —S(O)H; and R$^{4c}$ is, independently at each occurrence, selected from =O, OH, —OCH$_3$, —OCH$_2$CH$_3$, —OCH$_2$CH$_2$CH$_3$, —OCH(CH$_3$)$_2$, CH$_3$, —CH$_2$CH$_3$, —CH$_2$CH$_2$CH$_3$, —CH(CH$_3$)$_2$, —CH=CH$_2$, —CH≡CH, —CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, F, Br, Cl, CF$_3$, —NR$^2$R$^{2a}$, —CH$_2$NR$^2$R$^{2a}$, —C(O)R$^{2c}$, —CH$_2$C(O)R$^{2c}$, —NR$^2$C(O)R$^{2b}$, —CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, and CH$_2$S(O)$_p$R$^{5a}$.

In another preferred embodiment, the present invention provides a novel compound, wherein the compound is selected from:

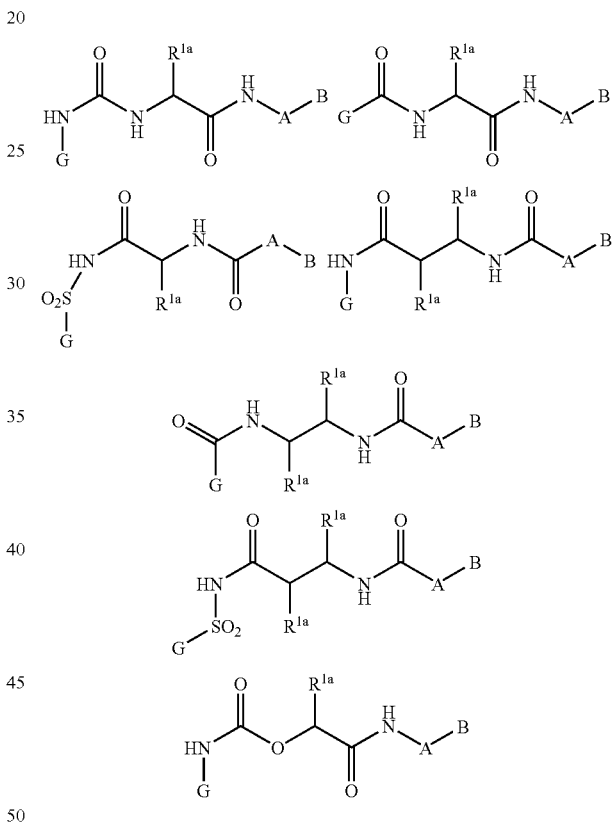

A-B is selected from:

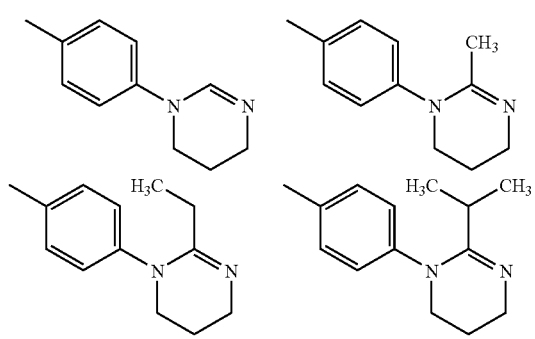

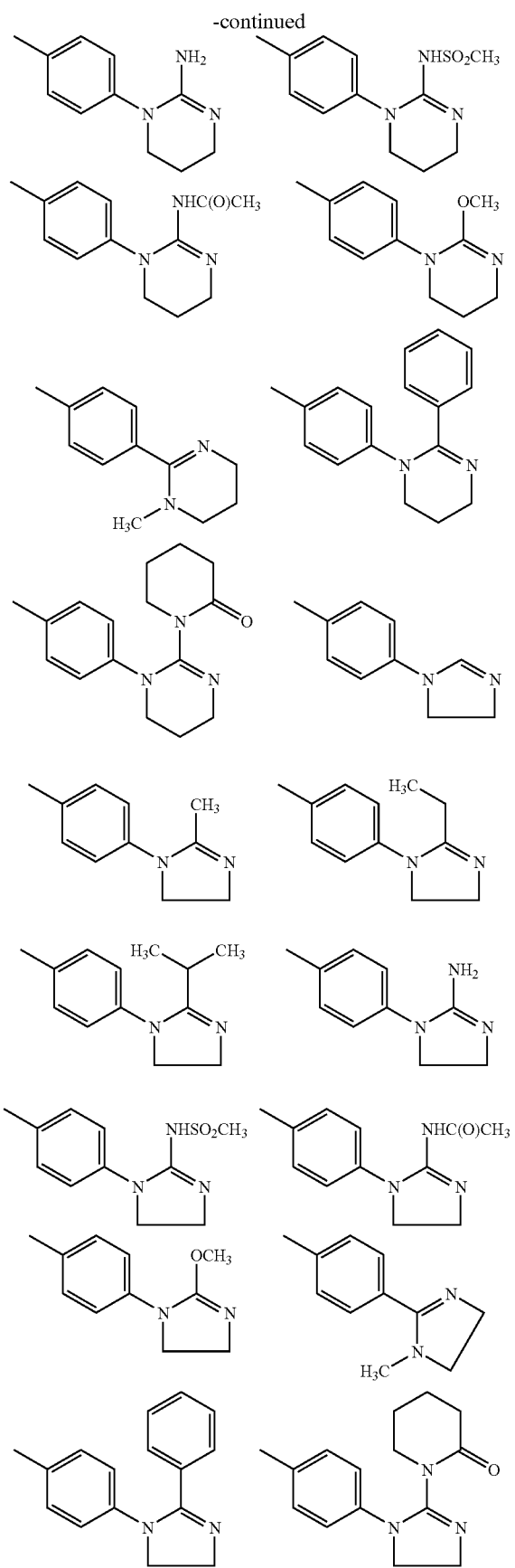
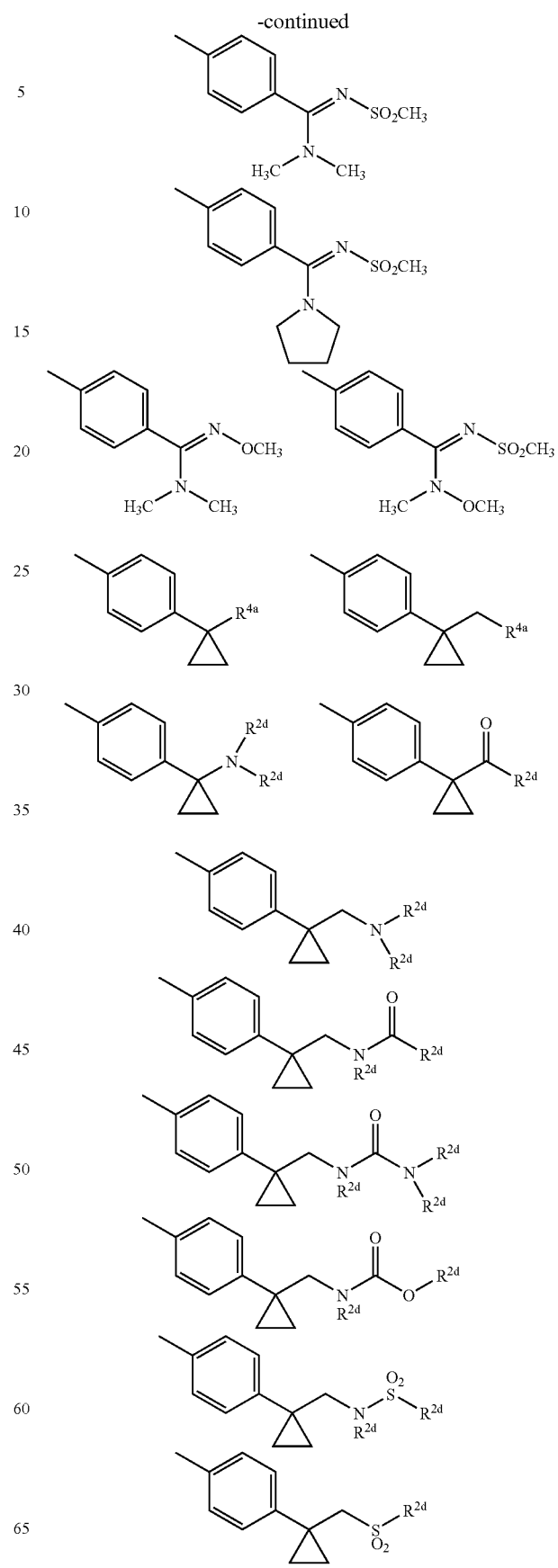

-continued
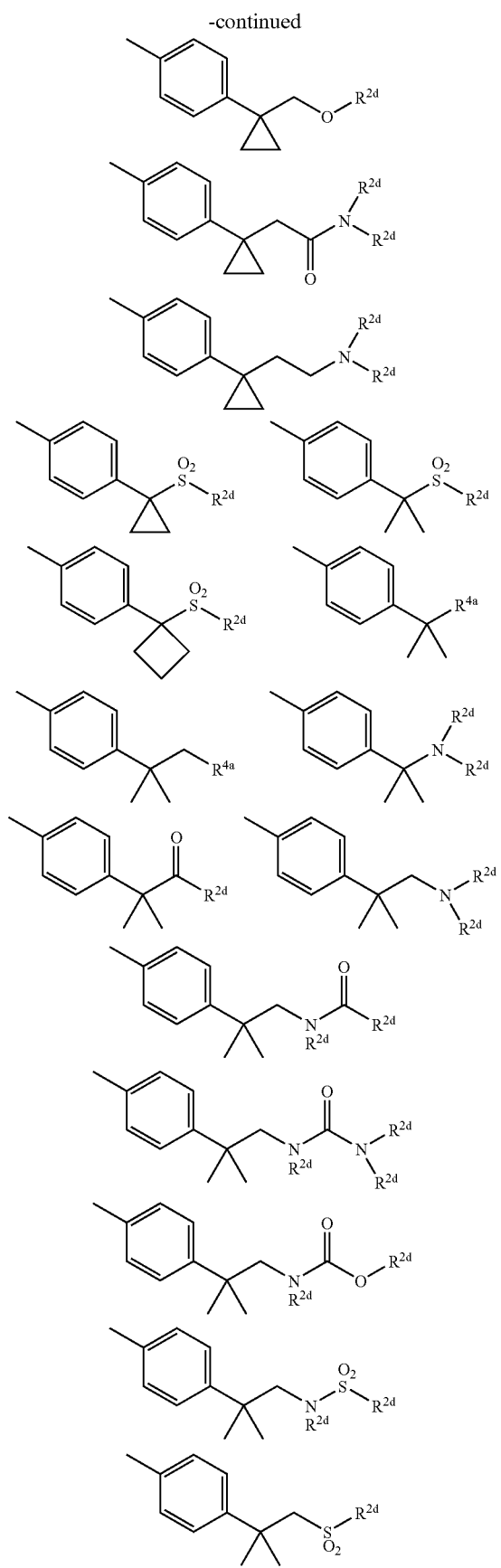
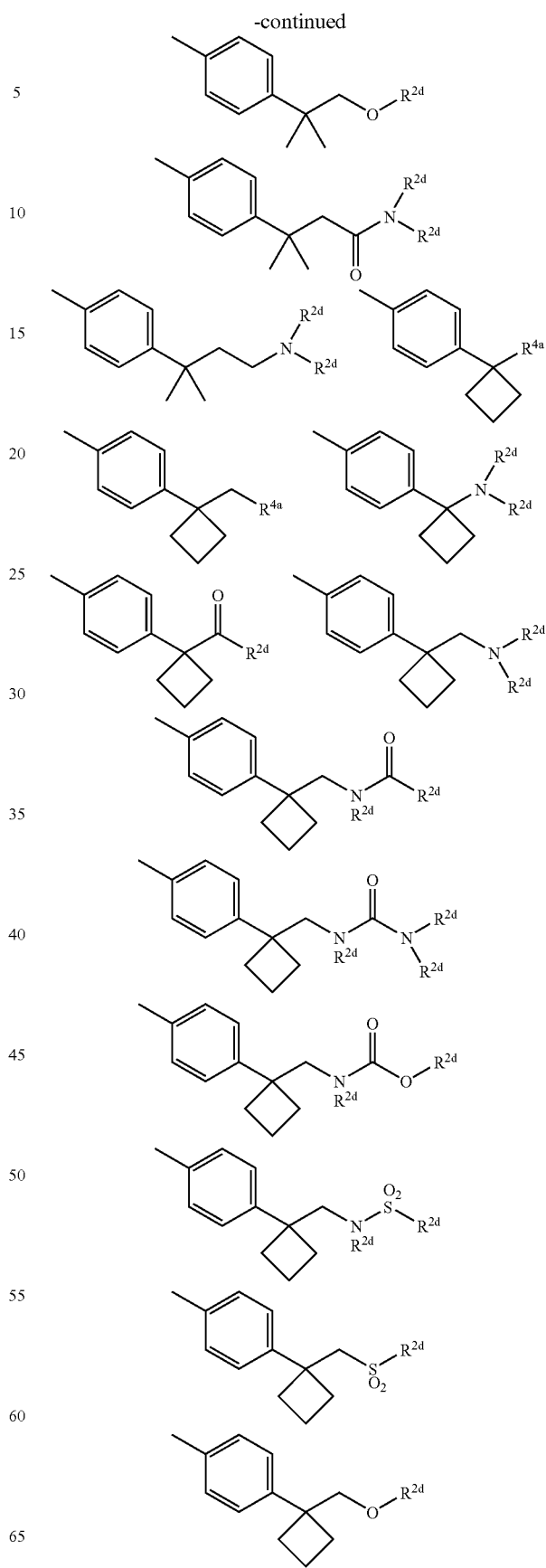

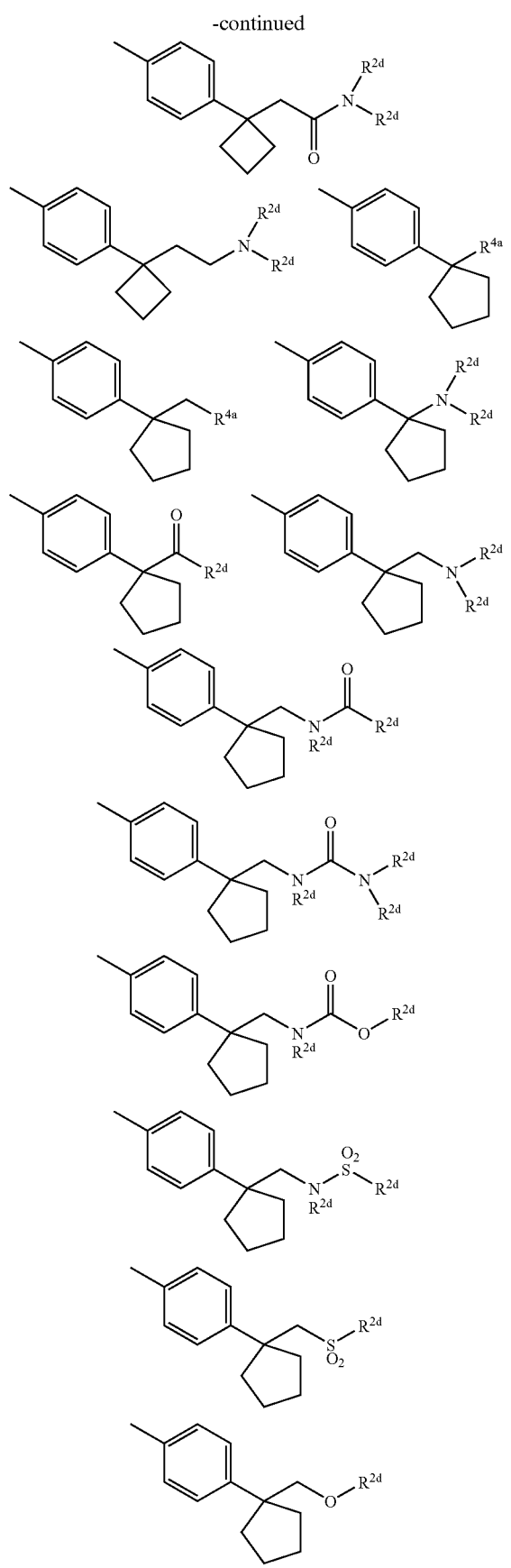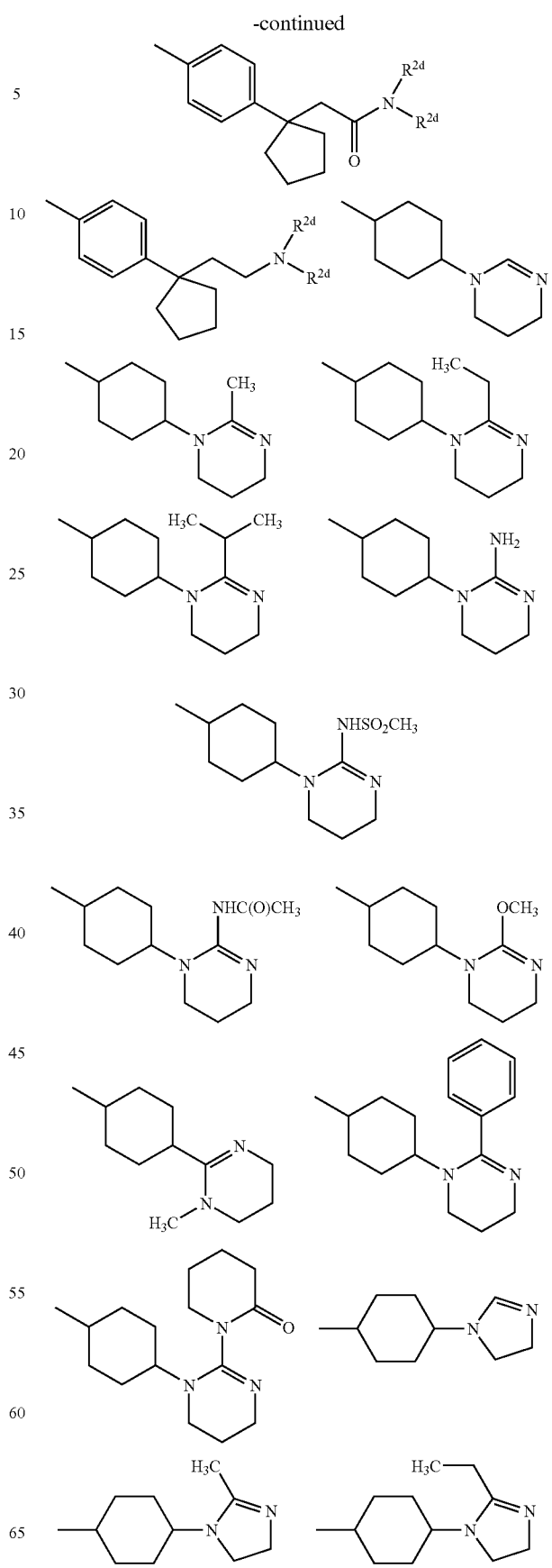

-continued

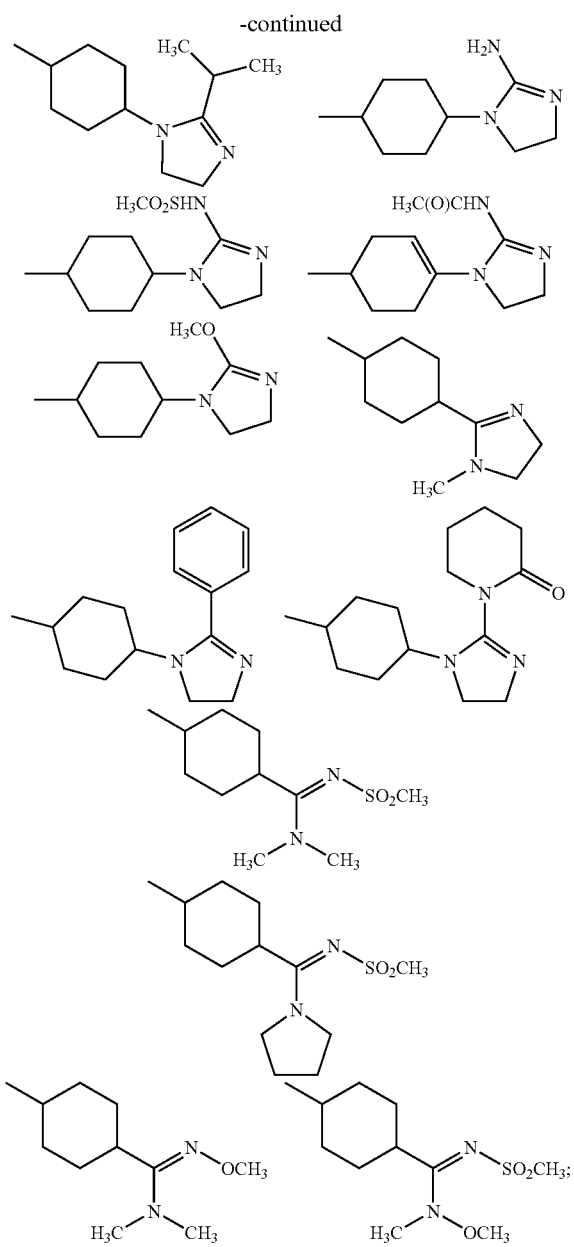

R$^{2d}$ is, independently at each occurrence, selected from H, CH$_3$, —CH$_2$CH$_3$, —CH$_2$CH$_2$CH$_3$, —CH(CH$_3$)$_2$, —CH$_2$CH(CH$_3$)$_2$, —CH$_2$CH$_2$CH(CH$_3$)$_2$, —CH$_2$C(CH$_3$)$_3$, —CH$_2$CH$_2$OH, —CH$_2$C(O)NH$_2$, cyclopropyl, —CH$_2$-cyclopropyl, cyclobutyl, cyclopentyl, and thiazolyl;

alternatively, NR$^{2d}$R$^{2d}$ forms a 5 or 6 membered saturated ring consisting of: 0-1 additional heteroatoms selected from N, O, and S(O)$_p$;

R$^{2e}$ is, independently at each occurrence, selected from CH$_3$, —CH$_2$CH$_3$, —CH$_2$CH$_2$CH$_3$, —CH(CH$_3$)$_2$, —CH$_2$CH(CH$_3$)$_2$, —CH$_2$CH$_2$CH(CH$_3$)$_2$, —CH$_2$-cyclopropyl, cyclopropyl, and cyclopentyl;

R$^{4a}$ is substituted with 0-2 R$^{4c}$ and selected from morpholine, 1,1-dioxo-thiomorpholine, dihydropyridine, piperidine, piperazine, pyrrolidine, imidazole, imidazoline, imidazolidine, oxazoline, and thiazoline; and R$^{4c}$ is selected from =O, OH, —OCH$_3$, and CH$_3$.

In another preferred embodiment, the present invention provides a novel compound, wherein the compound is selected from the group:

N-[2-(4-chloro-phenylcarbamoyl)-ethyl]-4-(1-pyrrolidin-1-ylmethyl-cyclopropyl)-benzamide;

5-chloro-thiophene-2-carboxylic acid {2-[4-(1-dimethyl-aminomethyl-cyclopropyl)-benzoylamino]-ethyl}-amide;

5-chloro-1H-indole-2-carboxylic acid {2-[4-(1-pyrrolidin-1-ylmethyl-cyclopropyl)-benzoylamino]-ethyl}-amide;

4-chloro-phenyl-carboxylic acid {2-[4-(1-pyrrolidin-1-ylmethyl-cyclopropyl)-benzoylamino]-ethyl}-amide;

4-chloro-phenyl-carboxylic acid {2-[4-(1-morpholin-4-ylmethyl-cyclopropyl)-benzoylamino]-ethyl}-amide;

4-chloro-phenyl-carboxylic acid {2-[4-(1-dimethyl-aminomethyl-cyclopropyl)-benzoylamino]-ethyl}-amide;

N-[2-(5-chloro-thiophene-2-sulfonylamino)-ethyl]-4-(1-pyrrolidin-1-ylmethyl-cyclopropyl)-benzamide; and 5-chloro-thiophene-2-carboxylic acid {phenyl-[4-(1-pyrrolidin-1-ylmethyl-cyclopropyl)-phenylcarbamoyl]-methyl}-amide; or a stereoisomer or pharmaceutically acceptable salt or solvate thereof.

In another preferred embodiment, the present invention provides a novel compound, wherein the compound is selected from those listed in table 1 or a stereoisomer or pharmaceutically acceptable salt or solvate thereof.

In another embodiment, the present invention provides a novel process for making a compound of the present invention or a stereoisomer or pharmaceutically acceptable salt or solvate thereof.

In another embodiment, the present invention provides a novel intermediate for making a compound of the present invention or a stereoisomer or pharmaceutically acceptable salt or solvate thereof.

In another embodiment, the present invention provides a novel pharmaceutical composition, comprising: a pharmaceutically acceptable carrier and a therapeutically effective amount of a compound of the present invention or a stereoisomer or pharmaceutically acceptable salt or solvate thereof.

In another embodiment, the present invention provides a novel method for treating a thromboembolic disorder, comprising: administering to a patient in need thereof a therapeutically effective amount of a compound of the present invention or a stereoisomer or pharmaceutically acceptable salt or solvate thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a stereoisomer or pharmaceutically acceptable salt or solvate thereof, in an amount effective to treat a thromboembolic disorder In another embodiment, the present invention provides a novel method, comprising: administering a compound of the present invention or a stereoisomer or pharmaceutically acceptable salt or solvate thereof, in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a stereoisomer or pharmaceutically acceptable salt or solvate thereof; and, (c) a package insert stating that the pharmaceutical composition can be used for the treatment of a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a stereoisomer or pharmaceutically acceptable salt or soivate thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Thus, the stereoisomeric configurations of each compound are considered part of the invention. Compounds of the present invention containing Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The term "linear chain," as used herein to describe linker M, is intended to mean a series of atoms (i.e., carbon, oxygen, nitrogen, and sulfur) that are connected together one at a time to form a chain. Thus, a chain atom is connected to one other chain atom if it is a terminal atom or two other chain atoms if is non-terminal. None of these chain atoms are bonded together, directly or indirectly, through a ring. Examples of a 5-membered linear chain include C(O)NHCH$_2$NHC(O) and NHC(O)CH$_2$S(O)$_2$NH, but not 1-amino-2-carbamoyl-cyclohexane. The number of chain atoms is determined by counting each atom in the chain, but not any atom substituted thereon. Thus, the 3 oxygen atoms and 4 hydrogen atoms of the group S(O)$_2$NHCH$_2$NHC(O)

are not counted, and S(O)$_2$NHCH$_2$NHC(O) is a 5-membered chain, not a 12-membered chain.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and SO$_2$H.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0-2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with an oxidizing agent (e.g., MCPBA and/or hydrogen peroxides) to afford other compounds of this invention. Thus, all shown and claimed amines are considered to cover both the shown amine and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —C$_v$F$_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge. Spiro rings are also included. Spiro rings are formed when to or more atoms (i.e., C, O, N, or S) of a chain are attached to the same carbon atom of the carbocycle. When a spiro ring is present, the substituents recited for the ring may also be present on the spiro.

As used herein, the term "heterocycle" or "heterocyclic group" is intended to mean a stable 3, 4, 5, 6, or 7-membered monocyclic or 7, 8, 9, 10, 11, or 12-membered bicyclic or tricyclic heterocyclic ring which is saturated, partially unsaturated or unsaturated (aromatic), and which consists of carbon atoms and 1, 2, 3, 4, or 5 ring heteroatoms independently selected from the group consisting of N, O and S. Heterocycle includes any bicyclic group in which one heterocyclic ring is fused to a second ring, which may be carbocyclic (e.g. benzo fusion) or heterocyclic. When a heterocycle is referred to as an "aromatic heterocycle" or "heteroaryl," this means that a fully unsaturated, i.e., aromatic, ring is present in the heterocycle. An aromatic heterocycle only requires one ring to be aromatic, if more than one ring is present. The aromatic portion of the aromatic heterocycle can be a carbocycle or heterocycle. The nitrogen and sulfur heteroatoms in the heterocycle may optionally be oxidized (i.e., N→O and S(O)$_p$). The nitrogen atom may be unsubstituted (i.e., N or NH) or substituted (i.e., NR wherein R is a substituent) and may optionally be quaternized. The heterocyclic ring may be attached to its pendant group at any heteroatom or carbon atom that results in a stable structure. The heterocyclic rings described herein may be substituted on a carbon or on a nitrogen atom, if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. It is to be noted that total number of S and O atoms in the aromatic heterocycle is not more than 1. Bridged and spiro rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge. Spiro rings are formed when to or more atoms (i.e., C, O, N, or S) of a chain are attached to the same carbon atom of a heterocycle (or carbocycle if fused to a heterocycle). When a spiro ring is present, the substituents recited for the ring may also be present on the spiro.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperazinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimnidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group. respectively. Examples of prodrugs include, but are not limited to, acetate, formate, and benzoate derivatives of alcohol and amine functional groups in the compounds of the present invention.

It should further be understood that solvates (e.g., hydrates) of the compounds of the present invention are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27-55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

All references cited herein are hereby incorporated in their entirety herein by reference.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. Those skilled in the art of organic synthesis understand that the functionality present on the molecule should be consistent with the transformations proposed. This will sometimes require a judgment to modify the order of the synthetic steps or to select one particular process scheme over another in order to obtain a desired compound of the invention.

Another major consideration in the planning of any synthetic route in this field is the judicious choice of the protecting group used for protection of reactive functional groups present in the compounds described in this invention. An authoritative account describing the many alternatives to the trained practitioner is Greene and Wuts (*Protective Groups In Organic Synthesis*, Wiley and Sons, 1991).

The synthesis of compounds of the present invention that involves the usage of intermediate A-B is accomplished via standard methods known to those skilled in the art.

Construction of compounds with general structure G-M-A-B can be performed in two directions: 1) From G to G-M (or a derivative of M) then to G-M-A-B or 2) From A-B to M-A-B (or a derivative of M) then to G-M-A-B. The general route that involves this type of methodology is outlined in Scheme 1. During the synthesis of these compounds, protecting groups to prevent cross-reaction during the coupling conditions optionally protect the functional groups of the substituents. Examples of suitable blocking groups and their uses are described in "The Peptides: analysis, Synthesis, Biology", Academic Press, Vol. 3 (Groii, et. al. Eds., 1981). Functional group transformations and coupling reactions that can be used to prepare compounds of the present invention are described in "Advanced Organic Chemistry: Reaction, Mechanism, and Structure", (March, et. al. fourth Ed.) and "Comprehensive Organic Transformations", (Larock, second Ed.).

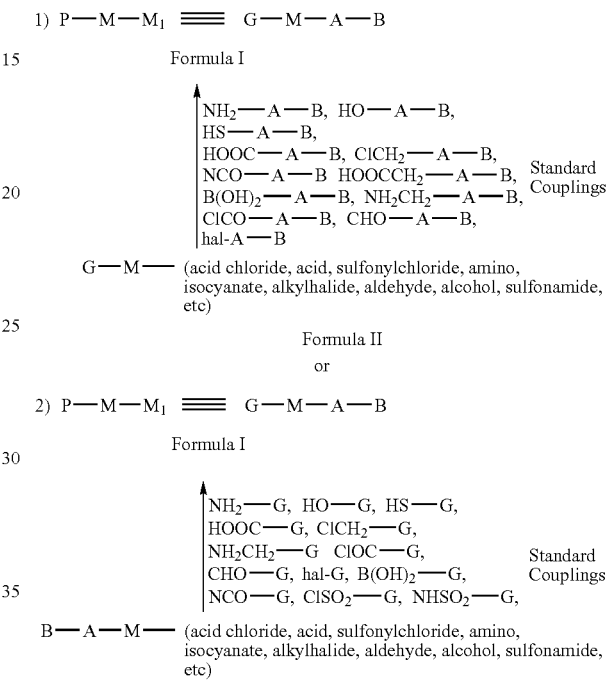

Compounds of the present invention where B is Y—$R^{4a}$ (provided that A and $R^{4a}$ are attached to the same carbon atom in Y, and Y is $C_{3-7}$ cycloalkyl) can be prepared as shown in Scheme 2. Commercially available 4-nitrophenylacetonitrile (or properly protected 4-aminophenylacetonitrile) can be used as the starting material. Alkylation with NaH, KtOBu, $NaNH_2$, n-BuLi, s-BuLi, NaOEt, aq NaOH, etc. as the base, and X—$(CH_2)_n$—Y (X and Y can be Cl, Br, I, OMs, OTs, or $^+S(CH_3)_2$ and n=2-6) as the alkylating reagent can afford the cycloalkyl intermediate 1. Hydrolysis of the nitrile group, followed by reduction of the ester group can provide the alcohol 2. Oxidation of 2, then reductive amiination with $NHR^{2d}R^{2d}$ can provide 3. Reduction of the nitro group or deprotection of the amino group can produce the A-B precursor 4, which can be coupled with 5 using standard coupling conditions as described in Scheme 1 to provide 6. When one of the $R^{2d}$ groups is H, 6 can react with acid chlorides, carbamoyl chlorides, sulfonyl chlorides, and isocyanates to provide compounds of the invention with structures 7, 8, 9, and 10. Alternatively, alcohol 2 can react with alkyl halides and amines to form compounds of the invention with structures 11 and 12. Alcohol 2 can also be transferred into a halide or its equivalents (X═Cl, Br, I, OMs, or OTs), followed by alkylation with a variety of alkylating reagents to afford compounds of the invention with structures 13, 14, and 15.

Scheme 2
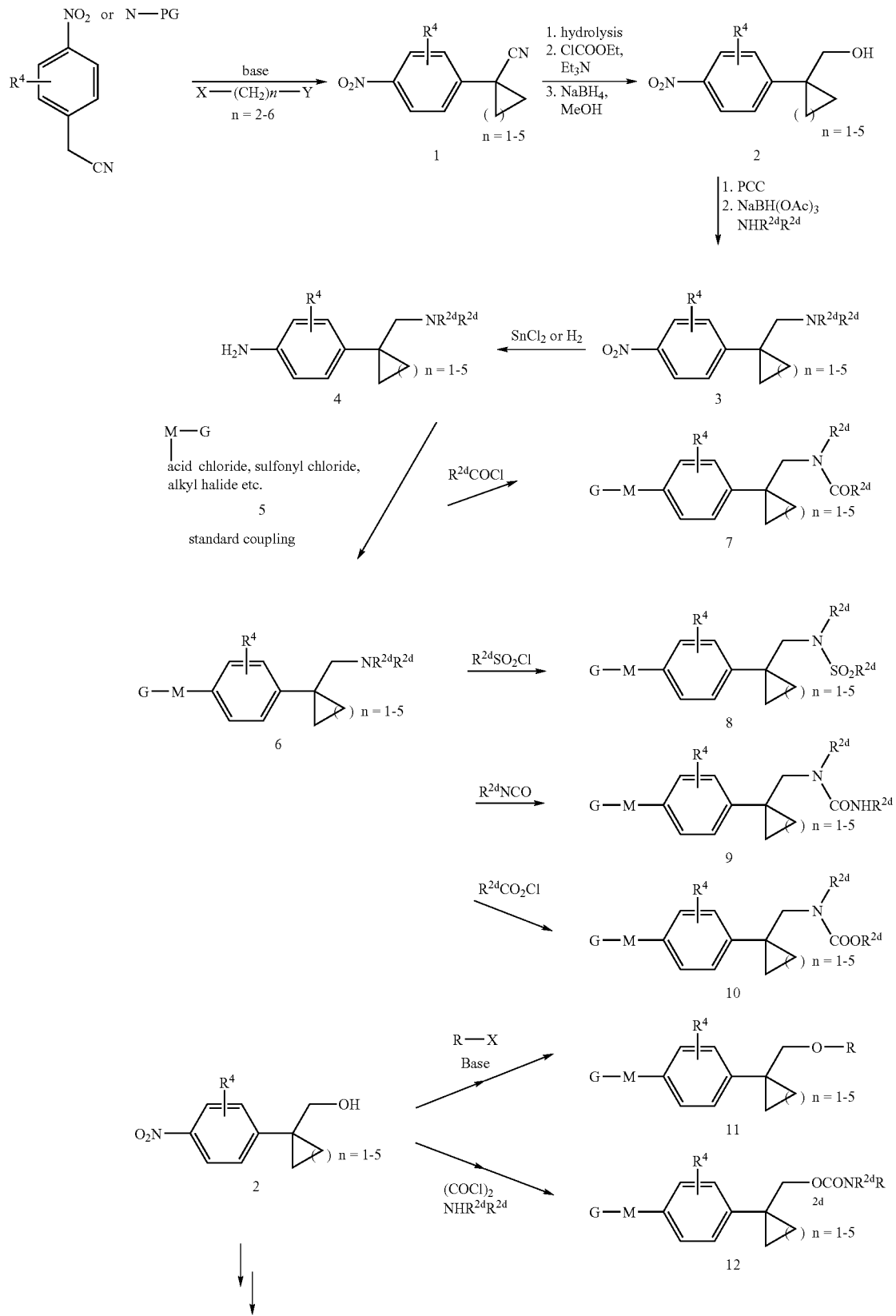

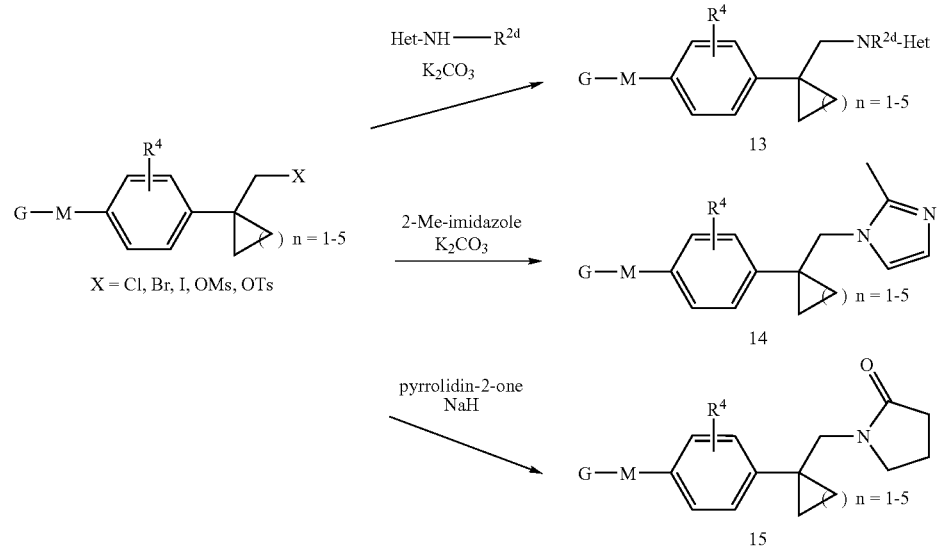

Other compounds of the present invention where Y is a cycloalkyl derivative can be prepared using commercially available 1-phenylcycloalkylcarboxylic acids (or 1-phenylcycloalkylcarbonitriles) as the starting materials illustrated in Scheme 3. Thus, nitration, followed by reduction of the NO$_2$ group and protection of the acid group can provide the A-B precursor 16, which can be coupled with 5 using standard coupling conditions to provide 17. Alternatively, iodination can provide the desired para-substituted compound 18, which can in turn be transformed to the amine 16 via Buchwald palladium-catalyzed amination (*Tetrahedron Lett.* 1997, 38, 6367-6370) and to the acid 19 via paladium-catalyzed carboxylation (CO, Pd(OAc)$_2$, dppf). Additional A-B intermediates can be synthesized by chemical manipulation of the amino and carboxylic acid functionality in 16 and 19, respectively. Compound 19 can be homologated via the Arndt-Eistert methodology to afford other A-B intermediates in 20. Alternatively, the acid functionality in 19 can be reduced to the alcohol that in turn can be converted to a variety of A-B intermediates 20 by procedures known to those skilled in the art. Further elaboration of these intermediates using the methods described above and by those known in the art should provide compounds of the present invention.

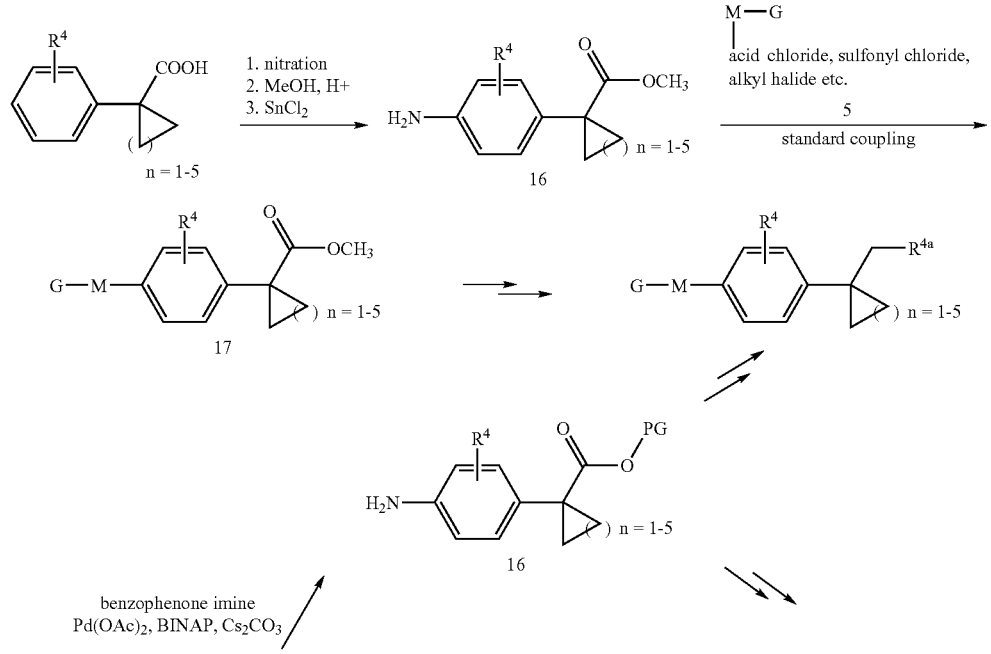

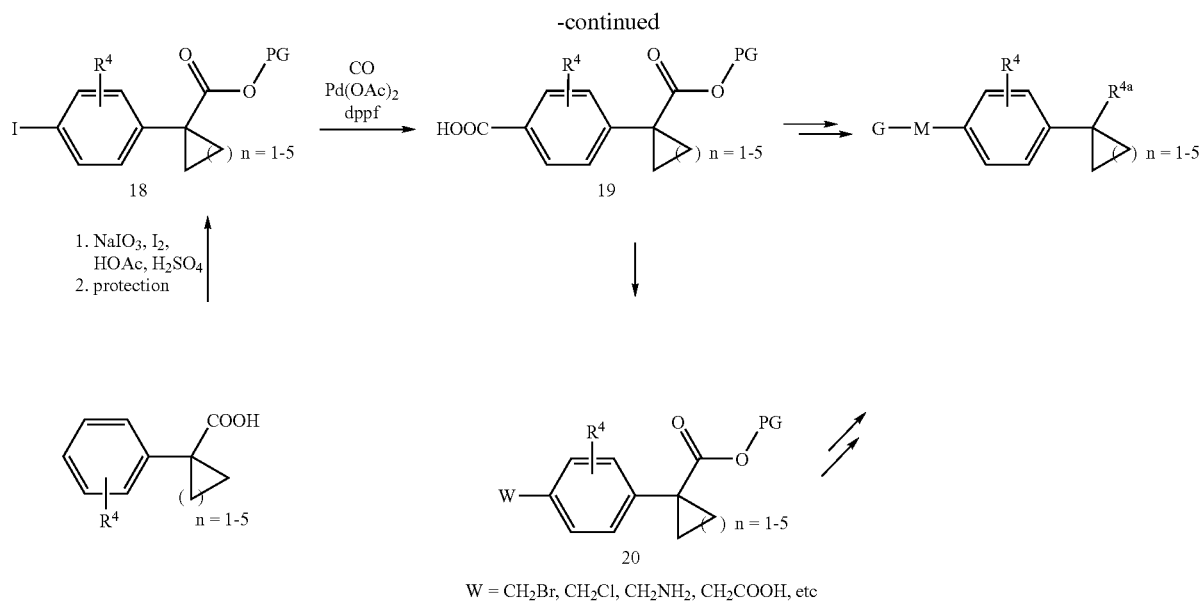

Other compounds of the present invention where Y is a cycloalkyl derivative can be prepared using organometalic reagents (Zn, Mg, etc) 21 as starting materials as shown in Scheme 4. Reaction of 21 with properly substituted cycloalkyl halides 22 (X=Cl, Br, I, OMs, OTs, etc.) using Pd(dba)$_2$/1,2-bis(diphenylphosphino)ethane (dppe) or NiCl$_2$(PPh$_3$)$_2$ as the catalyst system can provide intermediate 23. Alternatively, Grignard reaction of 21 with cycloalkyl ketones can provide intermediate 24. Further elaboration of 23 and 24 using the methods described above and by those known in the art should provide compounds of the present invention.

Compounds of the present invention where Y is a pyrrolidine or piperidine derivative can be prepared as shown in Scheme 5. Thus, phenylcyanoacetate can be alkylated with X—(CH$_2$)$_n$—Cl (X and Y=Br, I, OMs, OTs, etc and n=2-3) to provide the chloronitrile 25, which can be reduced to the corresponding primary amine, followed by cyclization in refluxing EtOH to form 3-pyrrolidine or 3-piperdine derivatives 26. Alkylation or reductive amination can provide the N-substituted intermediate 27. Further elaboration using the methods described above and by those known in the art should provide compounds of the present invention.

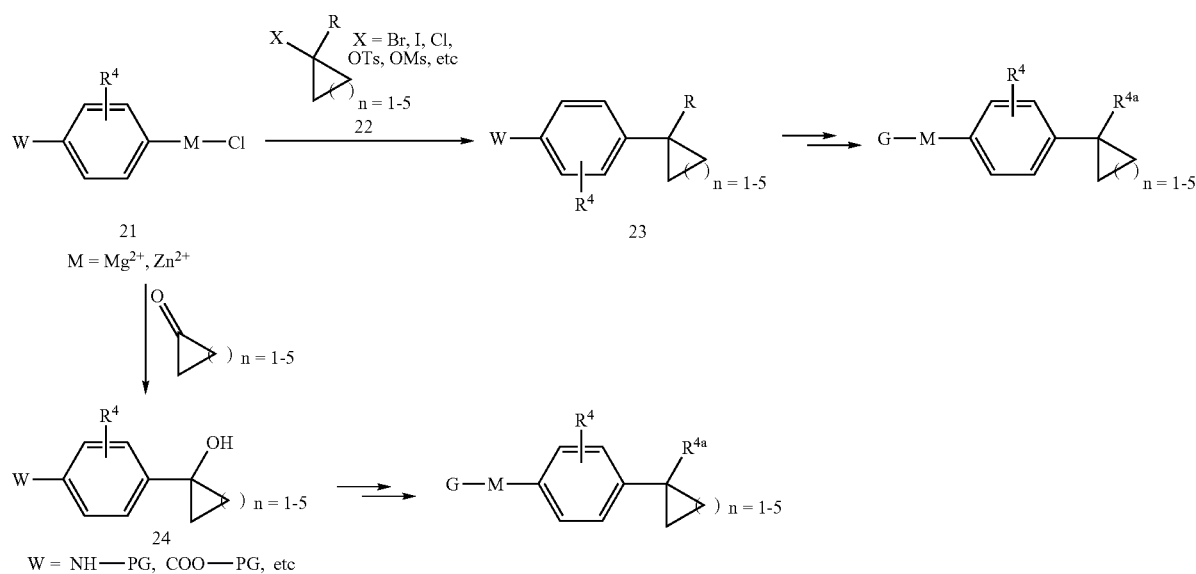

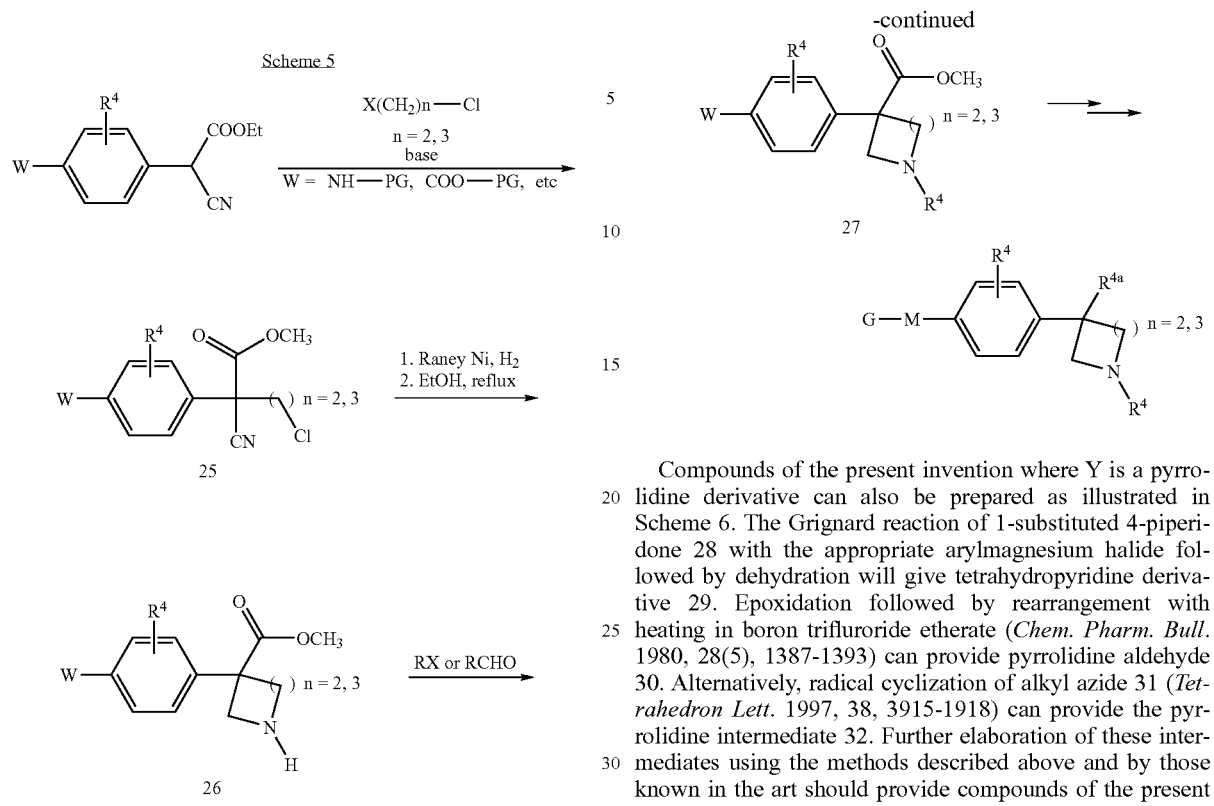

Compounds of the present invention where Y is a pyrrolidine derivative can also be prepared as illustrated in Scheme 6. The Grignard reaction of 1-substituted 4-piperidone 28 with the appropriate arylmagnesium halide followed by dehydration will give tetrahydropyridine derivative 29. Epoxidation followed by rearrangement with heating in boron trifluroride etherate (*Chem. Pharm. Bull.* 1980, 28(5), 1387-1393) can provide pyrrolidine aldehyde 30. Alternatively, radical cyclization of alkyl azide 31 (*Tetrahedron Lett.* 1997, 38, 3915-1918) can provide the pyrrolidine intermediate 32. Further elaboration of these intermediates using the methods described above and by those known in the art should provide compounds of the present invention.

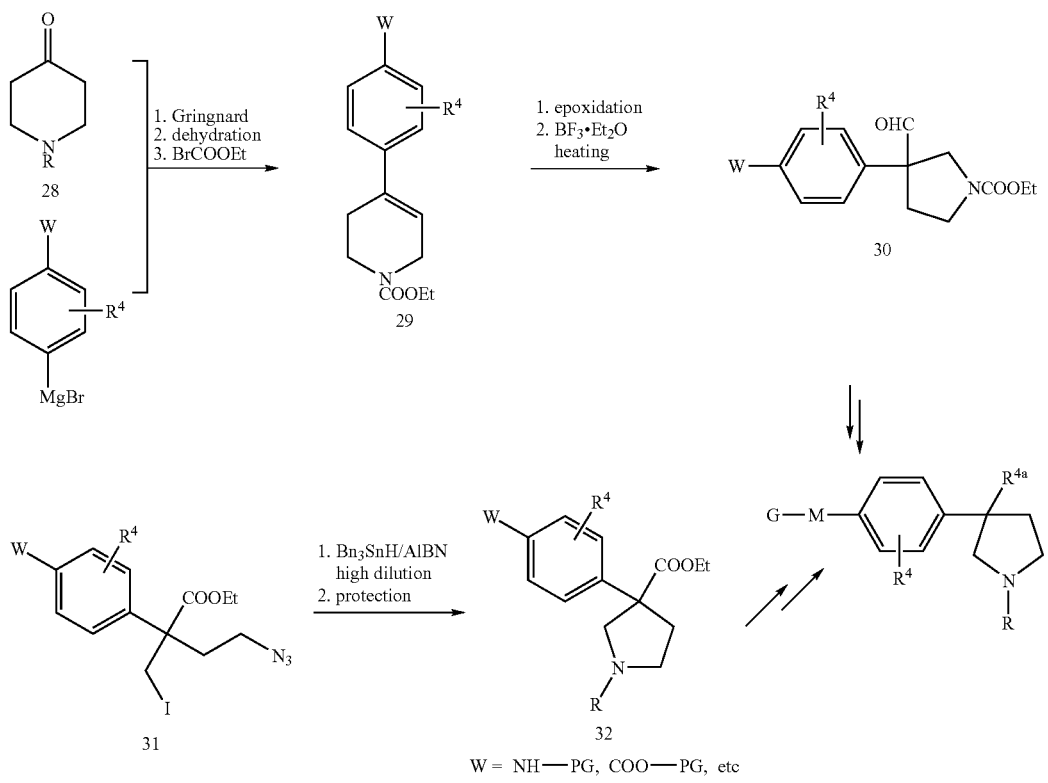

Compounds of the present invention where Y is a 4-piperidine derivative can be prepared using 2-aryl acetonitriles 33 as starting materials as shown in Scheme 7. Dialkylation of 33 with bromoacetaldehyde dimethyl acetal, followed by hydrolysis of the acetals and reductive amination will give the 4-aryl-4-cyanopiperidine 34. Further elaboration of these intermediates using the methods described above and by those known in the art should provide compounds of the present invention.

Scheme 7

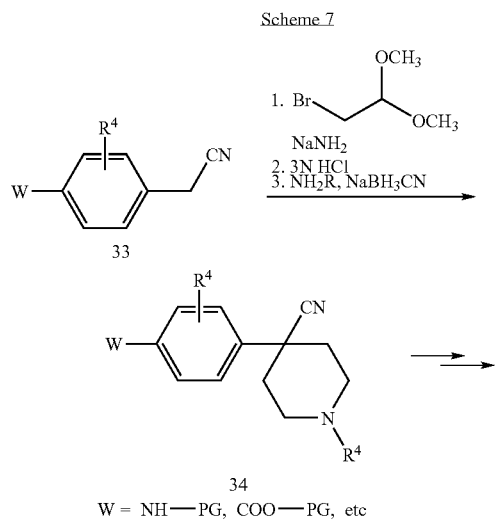

34
W = NH—PG, COO—PG, etc

Compounds of the present invention where Y is a 4-tetrahydrfuran derivative can be prepared using diol 35 as the starting material as illustrated in Scheme 8. Cyclization of 35 with HBr will give the 4-aryl-4-substituted tetrahydrofuran 36. Further elaboration using the methods described above and by those known in the art should provide compounds of the present invention.

Scheme 8

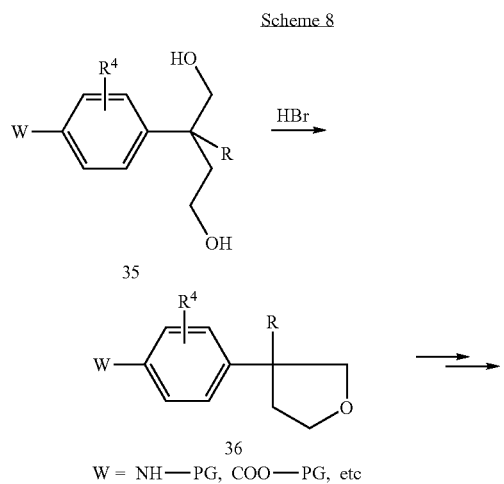

36
W = NH—PG, COO—PG, etc

-continued

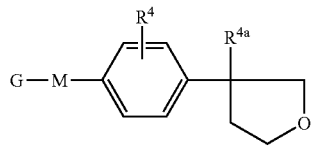

Compounds of the present invention where Y is a 4-tetrahydropyran derivative can be prepared using 2-aryl acetonitriles 33 as starting materials as shown in Scheme 9. Alkylation of 33 with di-2-chloroethyl ether will give the 4-aryl-4-cyanotetrahydropyran 37. Further elaboration using the methods described above and by those known in the art should provide compounds of the present invention.

Scheme 9

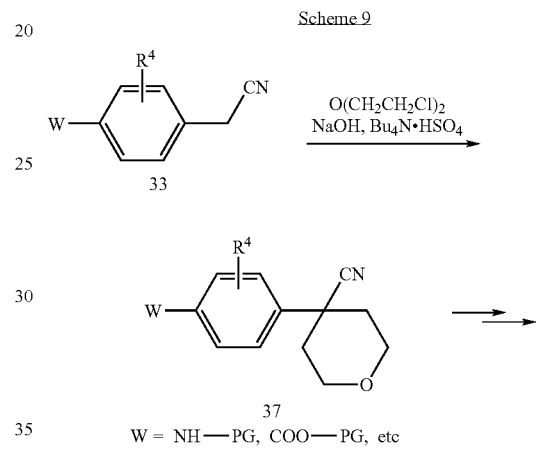

37
W = NH—PG, COO—PG, etc

Compounds of the present invention where Y is a lactam derivative can be prepared using intermediate 38 as the starting material as shown in Scheme 10. Reduction of $NO_2$ group or nitrile group can provide the primary amine 39, which can be coupled intramolecularly with the acid or ester to form the lactam 40. Further elaboration using the methods described above and by those known in the art should provide compounds of the present invention.

Scheme 10

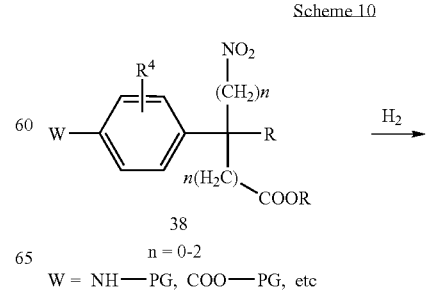

38
n = 0-2
W = NH—PG, COO—PG, etc

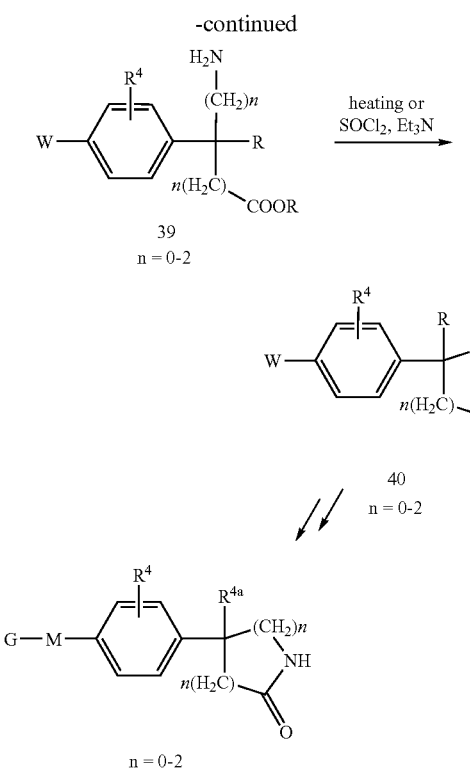

Aminopyridyl, aminopyrimidyl, cyclohexyl, and piperazinyl A-B analogs (see structures in Scheme 11) can be prepared using routes similar to those of Schemes 2-10 and by those known in the art. These intermediates can then be further manipulated to compounds of the present invention via procedures previously described.

Scheme 11

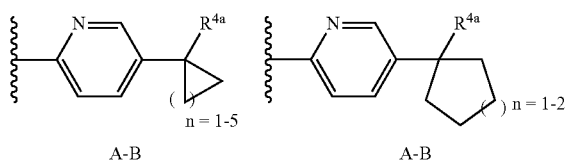

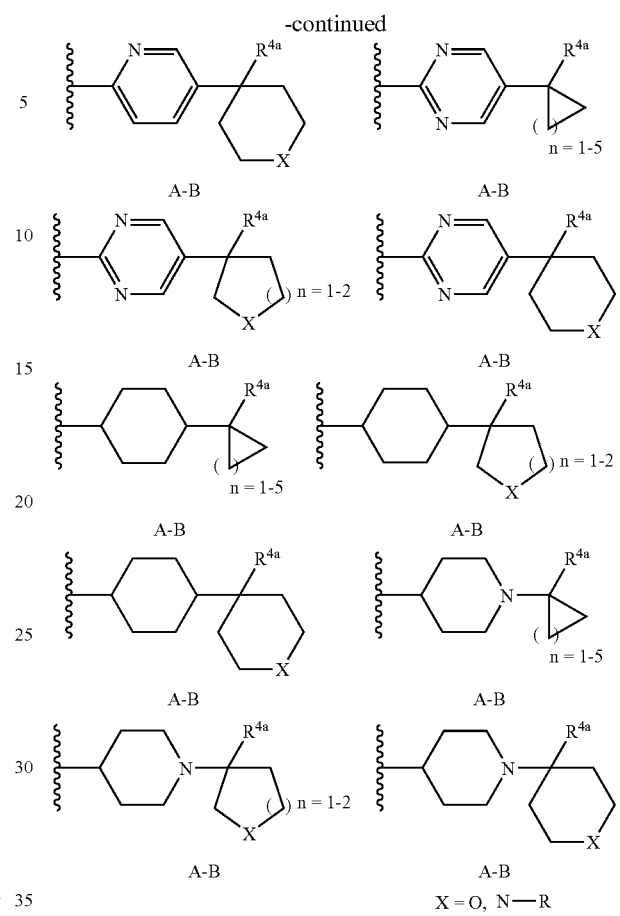

Compounds of the present invention (Scheme 1) where $R^{4a}$ is $CH_2CH_2NR^{2d}R^{2d}$ or $CH_2CONR^{2d}R^{2d}$ can be prepared as outlined in Scheme 12, and via standard methods known to those skilled in the art. The ester or nitrile intermediates 41 illustrated in Scheme 12 can be subjected to alkylation conditions, followed by other manipulations as described in Schemes 2-10 to form 42. Homologation of intermediates 42 can afford 43 with $TMSCHN_2$ as the reagent. Further elaboration of 43 to form 44 and compounds of the present invention can be achieved using the methods described above and by those known in the art.

Scheme 12

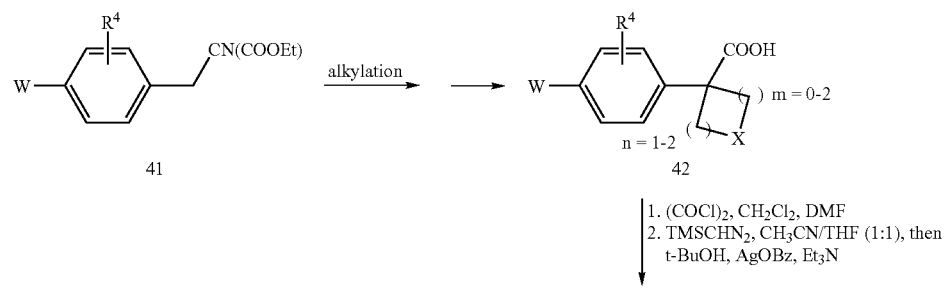

1. $(COCl)_2$, $CH_2Cl_2$, DMF
2. $TMSCHN_2$, $CH_3CN/THF$ (1:1), then t-BuOH, AgOBz, $Et_3N$

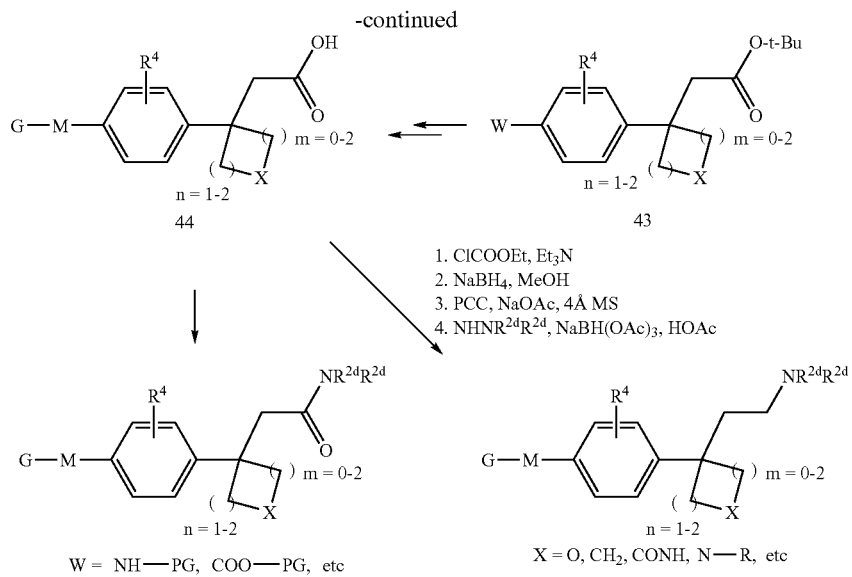

Compounds of the present invention where $R^{4a}$ is $NR^{2d}R^{2d}$ can be prepared as outlined in Scheme 13, and via standard methods known to those skilled in the art. The acid intermediates 42 illustrated in Scheme 13 can undergo Curtius rearrangement with DPPA in $CH_2Cl_2$ followed by heating in t-BuOH to afford Boc-protected cyclopropylamine intermediates 45. Alkylation of 45 with $R^{2d}$—I and NaH in THF followed by manipulations described previously will give amines 46. Reductive amination of 46 with aqueous formaldehyde and $NaBH_3CN$ in $CH_3CN$ can afford the methyl alkyl amine analogues. On the other hand, alkylation with dibromides using $K_2CO_3$ as the base can afford tertiary or cyclic amines, respectively. Further elaboration of 46 to form compounds of the present invention can be achieved using the methods described above and by those known in the art.

Scheme 13

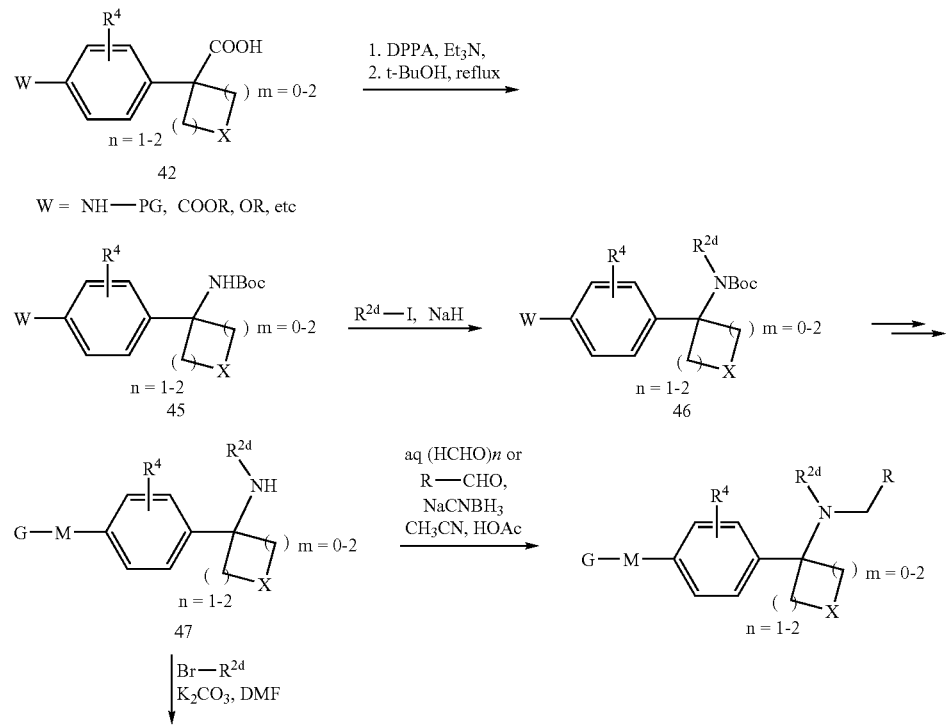

-continued

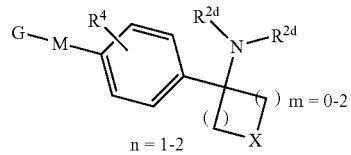

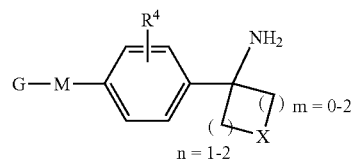

Schemes 2-13 describe how to make the A-B moieties of the present invention and how to couple them to prepare compounds of the present invention. Schemes 2-13 describe A-B wherein B is Y—$R^{4a}$ and Y is a cycloalkyl or heterocyclyl. Compounds of the present invention wherein Y is $CY^1Y^2$ can be made analogously to the cycloalkyl/heterocyclyl compounds of Schemes 2-13. For example, in Scheme 2, instead of intermediate 1 being a cycloalkyl intermediate, it can be $Y^1Y^2$ disubstituted intermediate. This intermediate could be made by a number of methods including di-substituting the starting 4-nitrophenyl-acetonitrile by reaction with a base and a $Y^1$-leaving group and a $Y^2$-leaving group. One of ordinary skill in the art would recognize that other routes to the $Y^1Y^2$ disubstituted intermediate are available. The remainder of the chemistry shown in Scheme 2 will then follow. In Scheme 3, instead of use the starting 1-phenylcycloalkylcarboxylic acids or 1-phenylcycloalkyl-carbonitriles, one could use the corresponding $Y^1Y^2$ disubstituted intermediates. Just like in Scheme 2, these intermediates could be prepared by di-substituting a phenylcarboxylic acid or phenylcarbonitrile. One of ordinary skill in the art would recognize that other routes to these types of $Y^1Y^2$ disubstituted intermediate are also available. The remainder of the chemistry shown in Scheme 3 will then follow.

Compounds of the present invention wherein Y is $N(B^1)C(O)C(R^3R^{3g})_{2-4}NB^2B^3$ can be made as described in Schemes 14-16. Scheme 14 describes the syntheses of A-B intermediate via Buchwald Ullman coupling reaction (*J. Am. Chem. Soc.* 2001, 123, 7727) using CuI and 1,2-cyclohexyldiamine or 1,10-phenanthroline as the catalyst.

-continued

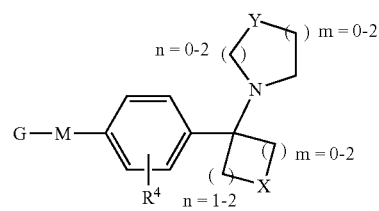

A-B

W = NH—PG, NO$_2$, Br, COOR, OR, etc standard coupling | M—G
acid chloride, sulfonyl chloride, alkyl halide etc.
5

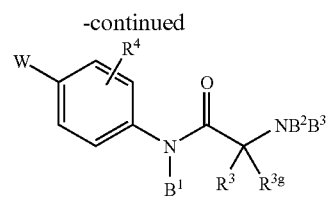

Alternatively, the A-B intermediates containing amides $NH(B^1)C(O)C(R^3R^{3g})_{2-4}NB^2B^3$ can also be prepared from readily available anilines as shown in Scheme 15.

Scheme 15

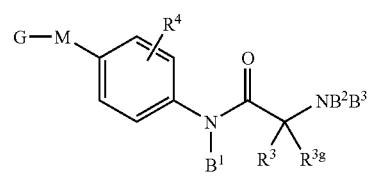

1. Boc$_2$O Heat
2. NaH, $B^1$—I
3. TFA

W = NH—PG, NO$_2$, Br, COOR, OR, etc

Scheme 14

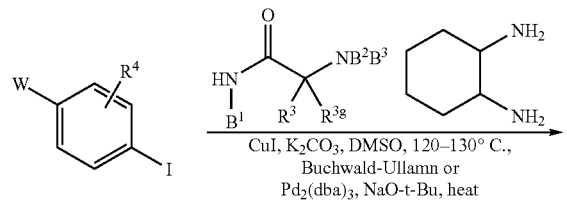

CuI, K$_2$CO$_3$, DMSO, 120–130° C., Buchwald-Ullamn or Pd$_2$(dba)$_3$, NaO-t-Bu, heat

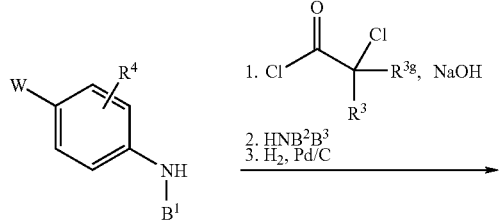

1. Cl—C(=O)—C(R$^3$)(R$^{3g}$)—Cl, NaOH
2. HNB$^2$B$^3$
3. H$_2$, Pd/C

-continued

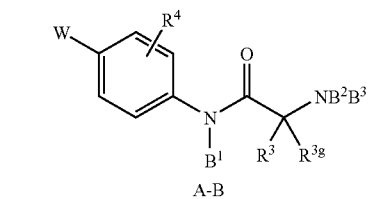

A-B

↓↓

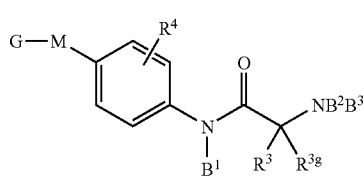

Aminopyridyl, aminopyrimidyl, indonyl, cyclohexyl, and piperazinyl A-B analogs (see structures in Scheme 16) can be prepared using routes similar to those of Schemes 14-15 and by those known in the art. These intermediates can then be further manipulated to compounds of the present invention via procedures previously described.

Scheme 16

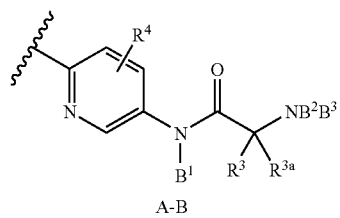

A-B

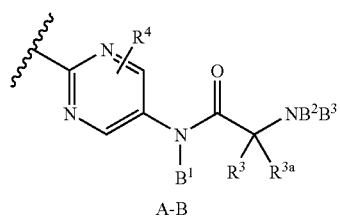

A-B

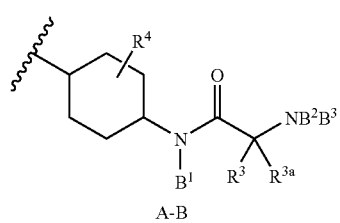

A-B

-continued

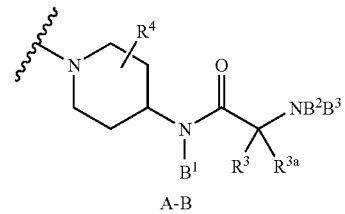

A-B

Compounds of the present invention wherein B is cyclic phenyl amidino derivatives can be prepared following the general procedure outlined in Scheme 17. Boc-protection of the aniline followed by alkylation with chloroiodo alkane can provide the Boc-protected intermediate. Azide displacement followed by reduction and deprotection can afford the diamine compound. Reaction with ethylformate, etc. can generate the corresponding A-B intermediate. Compounds wherein $R^{4a}$ is a H, alkyl, or ether can then be obtained using the methods described previously and by those known in the art.

Scheme 17

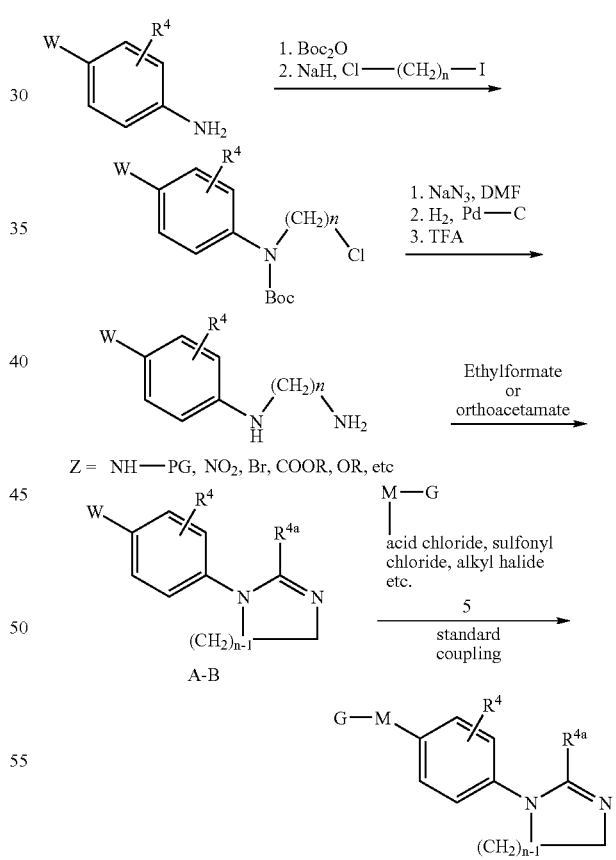

The diamino intermediate from Scheme 17 can also be cyclized with carbonyl diimidazole followed by treatment with $POCl_3$, $POBr_3$, $Tf_2O$, or an alkylating agent. Further manipulations of these versatile intermediates to the compounds of the present invention can be achieved using the methods described in Scheme 18 and by those known in the art.

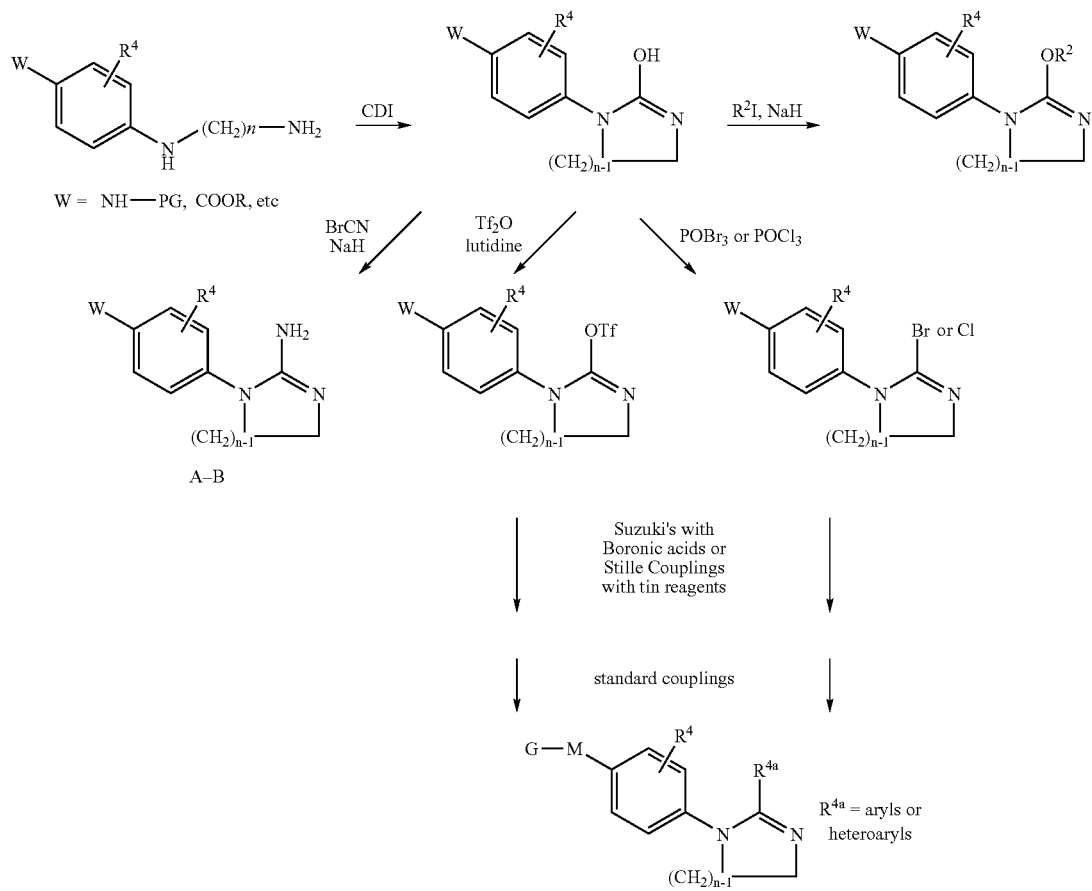
The guanidino derivative from Scheme 18 can be converted to a number of compounds of the present invention by techniques known to those of skill in the art of organic synthesis, as outlined in Scheme 19.
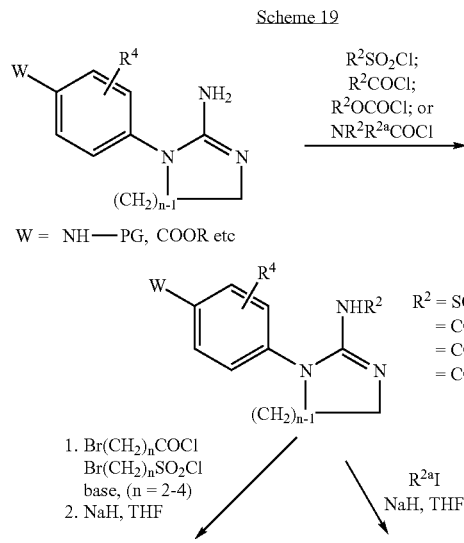
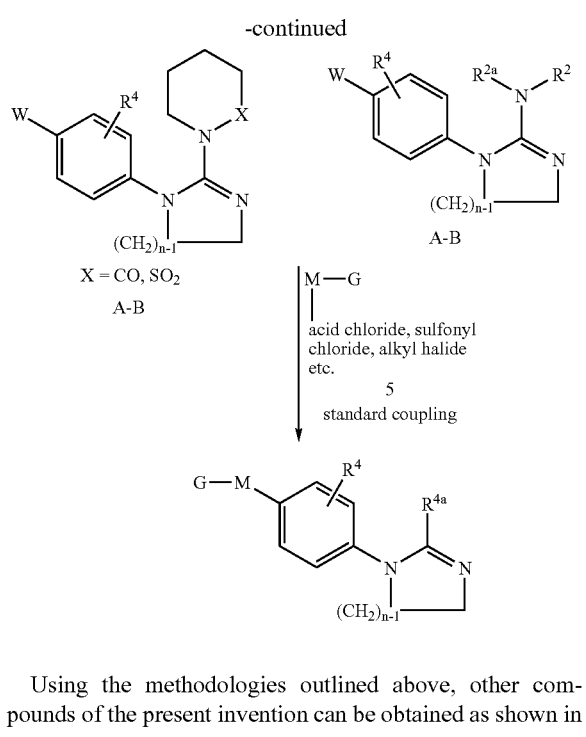
Using the methodologies outlined above, other compounds of the present invention can be obtained as shown in Scheme 20 by functional manipulations and cyclization techniques known to those of skill in the art of organic synthesis.

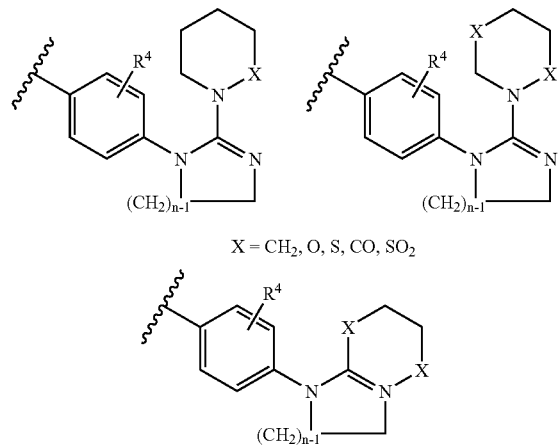

Phenylamidino-sulfonyl and -carbonyl compounds of the present invention can be obtained from the readily available amidino compounds shown in Scheme 21 below.

The compounds of this invention and the intermediates described above wherein the B group contains an oxidizable group can be oxidized, e.g., N to N-oxide.

The functionalized G moiety of the present invention, can be commercially available or can be prepared using methods known to those of ordinary skill in the art. All of the following patents and publications are incorporated herein by reference. For compounds wherein G is a ring substituted with a basic moiety, one of ordinary skill in the art can look to U.S. Pat. Nos. 5,939,418, 5,925,635, 6,057,342, 6,187,797, 6,020,357, 6,060,491, 6,191,159, WO98/57951, WO99/32454 WO00/059902, WO01/32628, WO00/39131, WO02/00651, WO02/102380, WO02/094197, U.S. Ser. No. 10/104,467, and USPA 2003/0018023 for starting materials. For compounds wherein G is a ring substituted with a non-basic group, one of ordinary skill in the art can look to U.S. Pat. No. 5,998,424, WO00/39131, WO00/059902, WO01/32628, WO02/00651, WO02/102380, WO02/094197, U.S. Ser. No. 10/104,467, and USPA 2003/0018023 for starting materials. For compounds wherein G is a bicyclic moiety, one of ordinary skill in the art can look to WO98/57951 WO00/039108, WO00/39131, WO02/00651, WO02/102380, WO02/094197, U.S. Ser. No. 10/104,467,

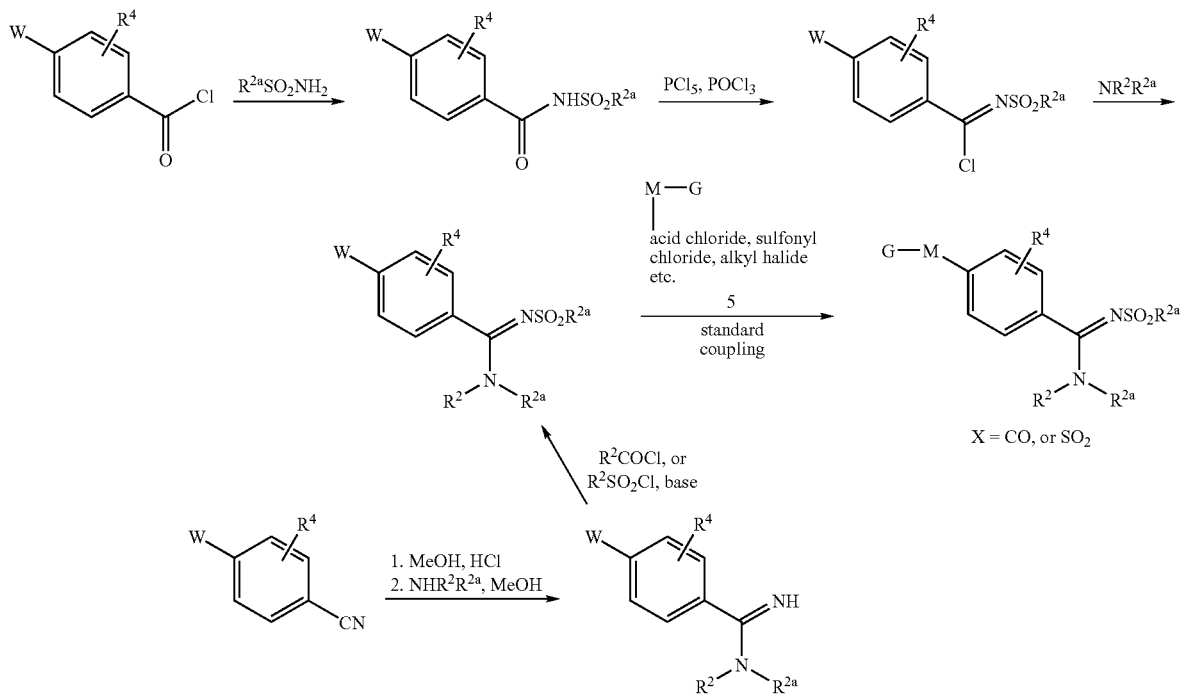

The chemistry leading to the compounds of the present invention described above can be implemented at various stages of the synthetic process. Those knowledgeable in the art may decide to prepare various sulfonyl, carbonylamidino, or suitably protected cyclic amidino intermediates and couple these via known techniques to various templates described herein to afford compounds of the present invention.

and USPA 2003/0018023 for starting materials. For compounds wherein A is an indoline or similar bicycle, one of ordinary skill in the art can look to WO01/005785 for starting materials and intermediates to which the present B group can be coupled or from which the present A-B groups can be formed.

Schemes 22-24 depict several examples for the synthesis of the compounds of the present invention. A properly protected amino acid derivative 48 (naturally or synthetically available) can couple with NH$_2$-A-B, followed by deprotection and transformations to compounds 49-53 in the present invention.

Similarly, the properly substituted ethylene diamine derivative 57 can couple with COOH-A-B (or ClCO-A-B) to form compounds 58 in this invention as illustrated in Scheme 24.

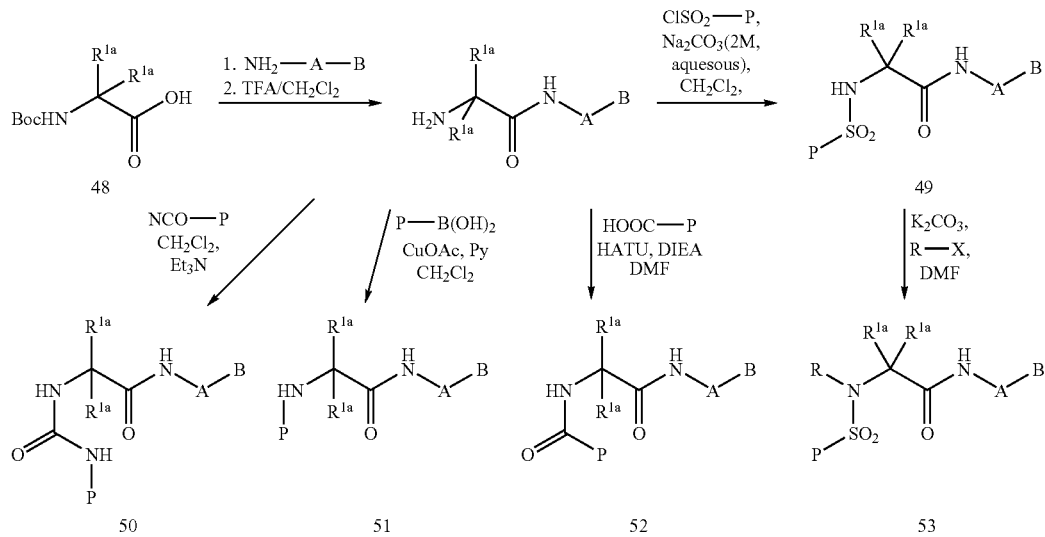

On the other hand, a properly protected β-amino acid derivative 54, can couple with COOH-A-B, followed by deprotaction and transformation to form compounds 55 and 56 in this invention as shown in Scheme 23.

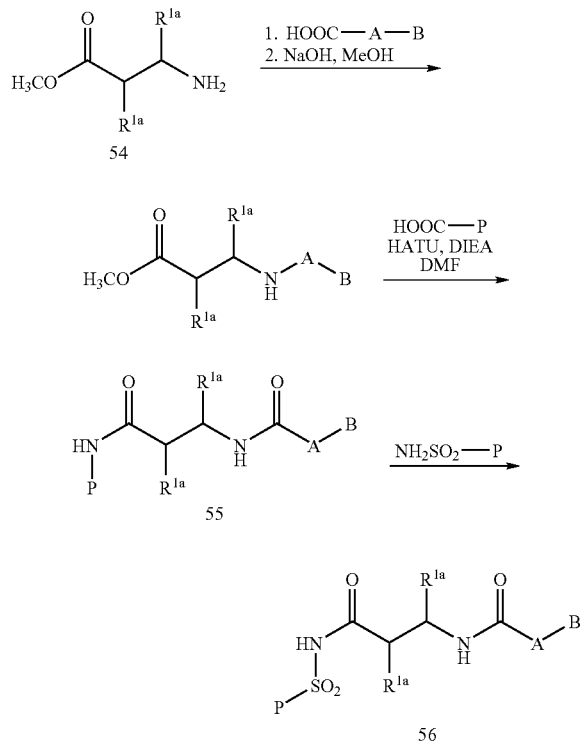

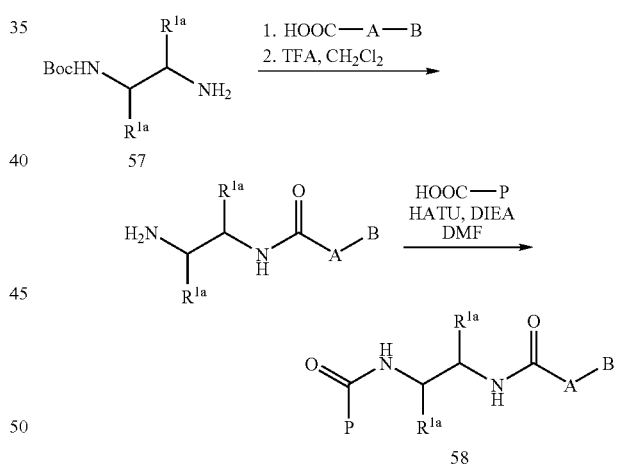

One stereoisomer of a compound of Formula I may display superior activity compared with the other. Thus, compounds of the present invention may be chiral and accordingly in various enantiomeric forms. They therefore may exist in racemic or in optically active form. When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of the present invention may also be obtained by chiral synthesis known to the person with skills in the art, e.g., synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis. An enantiomerically pure compound can be obtained with enantiomerically pure starting materials. Alternately, single stereoisomers can be obtained by chiral synthesis known to the person with skills in the art.

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nm. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2-0.5 nM human factor Xa (Enzyme Research Laboratories, South Bend, Ind.) to react with the substrate (0.20 mM -1 mM) in the presence of inhibitor. Reactions were allowed to go for 30 min and the velocities (rate of absorbance change vs. time) were measured in the time frame of 25-30 min. The following relationship was used to calculate $K_i$ values:

$$(v_o-v_s)/v_s=I/(K_i(1+S/K_m))$$

where:

$v_o$ is the velocity of the control in the absence of inhibitor;
$v_s$ is the velocity in the presence of inhibitor;
I is the concentration of inhibitor;
$K_i$ is the dissociation constant of the enzyme:inhibitor complex;
S is the concentration of substrate;
$K_m$ is the Michaelis constant.

Compounds tested in the above assay are considered to be active if they exhibit a $K_i$ of $\leq 10$ µM. Preferred compounds of the present invention have $K_i$'s of $\leq 1$ µM. More preferred compounds of the present invention have $K_i$'s of $\leq 0.1$ µM. Even more preferred compounds of the present invention have $K_i$'s of $\leq 0.01$ µM. Still more preferred compounds of the present invention have $K_i$'s of $\leq 0.001$ µM. Using the methodology described above, a number of compounds of the present invention were found to exhibit $K_i$'s of $\leq 10$ µM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After 40 min, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289-18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 min of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K+ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diuretics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congutated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/min during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70-80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

N-[2-(4-Chloro-phenylcarbamoyl)-ethyl]-4-(1-pyrrolidin-1-ylmethyl-cyclopropyl)-benzamide, trifluoroacetic acid salt

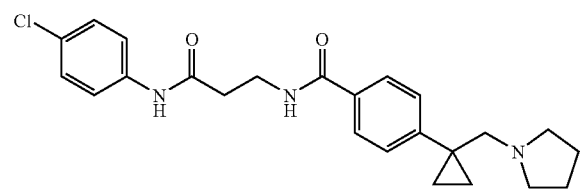

Part A. 4-Iodophenylcyclopropyl acid, methyl ester (1.40 g, 4.63 mmol) was dissolved in DMF/H$_2$O (1:2, v/v, 5 mL total) and K$_2$CO$_3$ (1.28 g, 9.26 mmol, 2 eq) and was added to a slurry of Pd(OAc)$_2$ (2.08 g, 9.26 mmol, 2 eq) under CO atmosphere (1 atm). After overnight at rt, the mixture was quenched by diluting with EtOAc and H$_2$O. The organic layer was washed with H$_2$O (2×). The combined aqueous layers were acidified with conc. HCl, extracted with CH$_2$Cl$_2$ (3×), dried over MgSO₄, filtered, and concentrated under vacuum overnight to give 4-(1-methoxycarbonyl-cyclopropyl)-benzoic acid (0.987 g, yield: 97%). ¹H NMR (acetone-d₆) δ 7.95 (d, J=8.1 Hz, 2H), 7.46 (d, J=8.1 Hz, 2H), 3.55 (s, 3H), 1.55 (m, 2H), 1.22 (m, 2H) ppm.

Part B. The product from Part A (250 mg, 1.14 mmol) was stirred in CH₂Cl₂ (2.0 mL) at rt. Oxalyl chloride (1.2 mL, 2.0 M, 2.4 mmol, 2.11 eq) was added followed by the addition of one drop of DMF. The mixture was stirred at rt for 2 h. The reaction was evaporated in vacuo to give crude 1-(4-chlorocarbonyl-phenyl)-cyclopropane-carboxylic acid methyl ester.

Part C. The product from Part B was stirred in CH₂Cl₂ (6 mL) at rt. β-Alan-o-tBu (excess) and DIEA (diisopropyl-ethyl amine)(excess) were added. The mixture was stirred at rt overnight. EtOAc was added. The mixture was washed with H₂O, brine, dried over MgSO₄, filtered, and concentrated to dryness to give 1-[4-(2-tert-butoxycarbonyl-ethylcarbamoyl)-phenyl]-cyclopropane-carboxylic acid methyl ester (0.27 g, yield: 69%). ¹H NMR (CDCl₃), δ 7.71 (d, J=8.4 Hz, 2H), 7.40 (d, J=8.4 Hz, 2H), 3.68 (q, J=5.8 Hz, 2H), 3.62 (s, 3H), 2.55 (t, J=5.8 Hz, 2H), 1.64 (m, 2H), 1.47 (s, 9H), 1.20 (m, 2H) ppm.

Part D. The product from Part C (0.27 g, 0.79 mmol) and TFA (4 mL) were stirred in CH₂Cl₂ (6 mL) at rt for 1 h. It was concentrated and stripped with CHCl₃ (3×) and then concentrated under vacuum. The residue was dissolved in a mixture of DMF and CH₂Cl₂ (8 mL total). 4-chloroaniline (0.09 g, 0.705 mmol) was added, followed by the addition of DIEA (1.5 mL, 8.61 mmol, 10 eq). The mixture was stirred at rt overnight. It was diluted with H₂O, extracted with EtOAc, washed with 1N HCl (2×), brine, dried over Na₂SO₄, filtered, and concentrated to dryness. The residue was purified by silica gel column chromatography (hexanes:EtOAc, 3:1 to 1:1) to give 1-{4-[2-(4-chloro-phenylcarbamoyl)-ethylcarbamoyl]-phenyl}-cyclopropane-carboxylic acid methyl ester (0.47 g, 100%). The residue (0.47 g, 0.78 mmol) was stirred in a mixture of 1N NaOH (8 mL) and methanol (16 mL) at rt for 5 h. The mixture was concentrated and extracted with Et₂O. The aqueous layer was acidified with conc. HCl, extracted with EtOAc and CH₂Cl₂, dried over MgSO₄, filtered, and concentrated to dryness to give 1-{4-[2-(4-chloro-phenylcarbamoyl)-ethylcarbamoyl]-phenyl}-cyclopropane-carboxylic acid (0.30 g, yield: 98%). ¹H NMR (CD₃OD) δ 7.72 (d, J=8.4 Hz, 2H), 7.54 (d, J=8.8 Hz, 2H), 7.42 (d, J=8.5 Hz, 2H), 7.26 (d, J=8.8 Hz, 2H), 3.67 (m, 2H), 2.68 (m, 2H), 1.58 (m, 2H), 1.20 (m, 2H) ppm.

Part E: The product from Part D (0.30 g, 0.78 mmol) and Et₃N (0.18 mL, 1.29 mmol, 1.7 eq) were stirred in THF (4.0 mL) at 0° C. under N₂. ClCOOEt (0.09 ml, 0.95 mmol, 1.2 eq) was added dropwise. The mixture was stirred at 0° C. for 20 min. It was filtered and stirred in a mixture of THF (8 mL) and MeOH (3 mL) at 0° C. NaBH₄ (0.18 g, 6.1 eq) was added. The mixture was stirred at 0° C. for 20 min. The reaction was quenched by brine, dried over Na₂SO₄, filtered, and concentrated to give N-[2-(4-chloro-phenylcarbamoyl)-ethyl]-4-(1-hydroxymethyl-cyclopropyl)-benzamide (0.12 g, yield: 42%). ¹H NMR (CD₃OD) δ 7.71 (d, J=8.4Hz, 2H), 7.54 (d, J=8.7 Hz, 2H), 7.41 (d, J=8.4 Hz, 2H), 7.26 (d, J=8.8 Hz, 2H), 3.64 (m, 4H), 2.67 (m, 2H), 0.89 (m, 2H), 0.81 (m, 2H) ppm.

Part F. The product from Part E (0.12 g, 0.32 mmol), molecular sieves (0.12 g), NaOAc (0.165 g, 2.01 mmol, 6.3 eq), and PCC (0.20 g, 0.94 mmol, 2.9 eq) were stirred in CH₂Cl₂ (2 mL) at rt for 3 h. The mixture was filtered through Celite®, washed with H₂O (2×), brine, dried over MgSO₄, filtered, and concentrated to give the crude aldehyde (72.8 mg, 61%). The residue (72.8 mg, 0.20 mmol) was stirred in ClCH₂CH₂Cl, pyrrolidine (40 ml, 0.48 mmol, 2.44 eq) and HOAc (1 drop) were added, followed by NaBH(OAc)₃ (0.13 g, 0.61 mmol, 3.1 eq). The mixture was stirred at rt for 3 h. It was purified by prep LC/MS to give pure final compound (5 mg, yield: 5% yield due to the poor solubility). LC/MS (ESI) 426.6 (M+H), $t_R$=2.36 min (5-98% CH₃CN in H₂O in a 10-min run).

Following a procedure analogous to that described in Example 1, Examples 2-8 were obtained.

Example 2

5-Chloro-thiophene-2-carboxylic acid {2-[4-(1-dimethyl-aminomethyl-cyclopropyl)-benzoylamino]-ethyl}-amide, trifluoroacetic acid salt

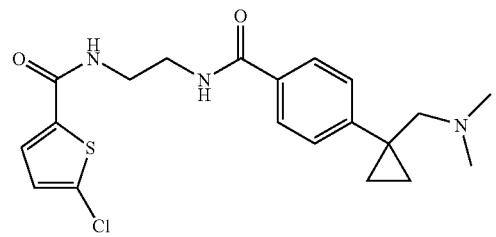

LC/MS ESI (M+H)⁺ 406.6.

Example 3

5-Chloro-1H-indole-2-carboxylic acid {2-[4-(1-pyrrolidin-1-ylmethyl-cyclopropyl)-benzoylamino]-ethyl}-amide, trifluoroacetic acid salt

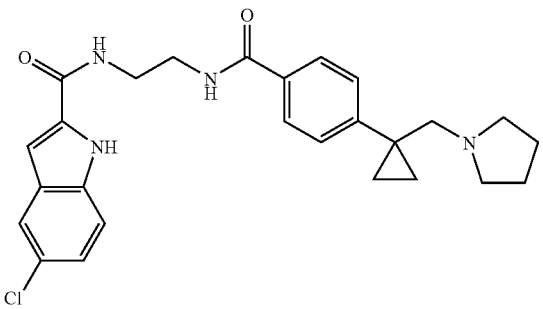

LC/MS ESI (M+H)⁺ 465.6.

Example 4

4-Chloro-phenyl-carboxylic acid {2-[4-(1-pyrrolidin-1-ylmethyl-cyclopropyl)-benzoylamino]-ethyl}-amide, trifluoroacetic acid salt

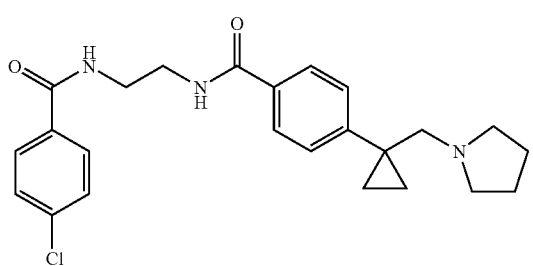

LC/MS ESI (M+H)⁺ 426.2.

Example 5

4-Chloro-phenyl-carboxylic acid {2-[4-(1-morpholin-4-ylmethyl-cyclopropyl)-benzoylamino]-ethyl}-amide, trifluoroacetic acid salt

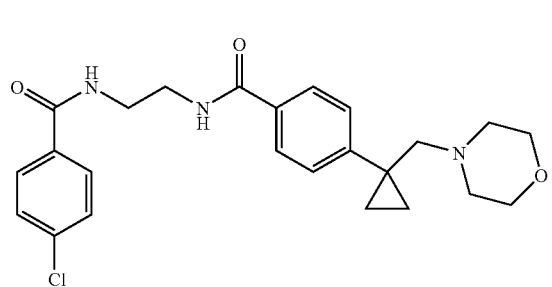

LC/MS ESI (M+H)$^+$ 442.2.

Example 6

4-Chloro-phenyl-carboxylic acid {2-[4-(1-dimethyl-aminomethyl-cyclopropyl)-benzoylamino]-ethyl}-amide, trifluoroacetic acid salt

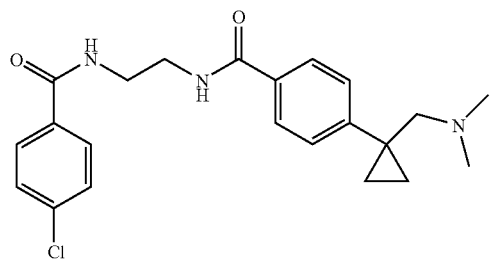

LC/MS ESI (M+H)$^+$ 400.2.

Example 7

N-[2-(5-Chloro-thiophene-2-sulfonylamino)-ethyl]-4-(1-pyrrolidin-1-ylmethyl-cyclopropyl)-benzamide, trifluoroacetic acid salt

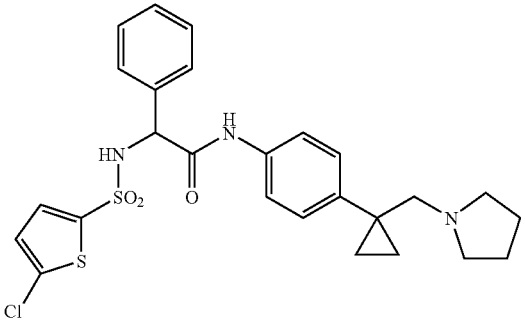

LC/MS ESI (M+H)$^+$ 468.2.

Example 8

5-Chloro-thiophene-2-carboxylic acid {phenyl-[4-(1-pyrrolidin-1-ylmethyl-cyclopropyl)-phenylcarbamoyl]-methyl}-amide, trifluoroacetic acid salt

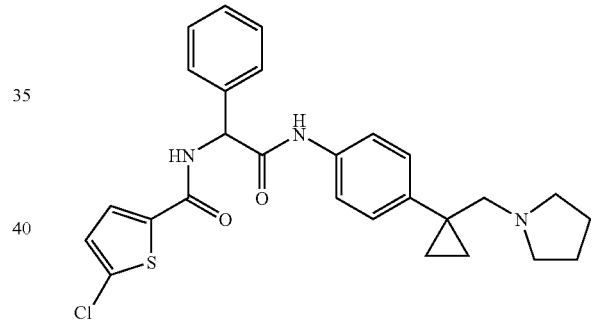

LC/MS ESI (M+H)$^+$ 494.2.

Examples 9-146, shown in Table 1 below, can be made using procedures similar to those of Examples 1-8.

TABLE 1

| Example | Name |
| --- | --- |
| 9. | 5-Chloro-1H-indole-2-carboxylic acid {phenyl-[4-(1-pyrrolidin-1-ylmethyl-cyclopropyl)-phenylcarbamoyl]-methyl}-amide |
| 10. | 3-Chloro-1H-indole-6-carboxylic acid {phenyl-[4-(1-pyrrolidin-1-ylmethyl-cyclopropyl)-phenylcarbamoyl]-methyl}-amide |
| 11. | 2-[3-(4-Chloro-phenyl)-ureido]-2-phenyl-N-[4-(1-pyrrolidin-1-ylmethyl-cyclopropyl)-phenyl]-acetamide |
| 12. | 5-Chloro-thiophene-2-carboxylic acid {[4-(1-dimethylaminomethyl-cyclopropyl)-phenylcarbamoyl]-phenyl-methyl}-amide |
| 13. | 5-Chloro-1H-indole-2-carboxylic acid {[4-(1-dimethylaminomethyl-cyclopropyl)-phenylcarbamoyl]-phenyl-methyl}-amide |
| 14. | 3-Chloro-1H-indole-6-carboxylic acid {[4-(1-dimethylaminomethyl-cyclopropyl)-phenylcarbamoyl]-phenyl-methyl}-amide |
| 15. | 2-[3-(4-Chloro-phenyl)-ureido]-N-[4-(1-dimethylaminomethyl-cyclopropyl)-phenyl]-2-phenyl-acetamide |
| 16. | 5-Chloro-thiophene-2-carboxylic acid {[4-(1,1-dimethyl-2-pyrrolidin-1-yl-ethyl)-phenylcarbamoyl]-phenyl-methyl}-amide |
| 17. | 5-Chloro-1H-indole-2-carboxylic acid {[4-(1,1-dimethyl-2-pyrrolidin-1-yl-ethyl)- |

TABLE 1-continued

| Example | Name |
|---|---|
| | phenylcarbamoyl]-phenyl-methyl}-amide |
| 18. | 3-Chloro-1H-indole-6-carboxylic acid {[4-(1,1-dimethyl-2-pyrrolidin-1-yl-ethyl)-phenylcarbamoyl]-phenyl-methyl}-amide |
| 19. | 5-Chloro-thiophene-2-carboxylic acid {[4-(1-methanesulfonyl-1-methyl-ethyl)-phenylcarbamoyl]-phenyl-methyl}-amide |
| 20. | 5-Chloro-thiophene-2-carboxylic acid {[4-(1-acetyl-cyclopropyl)-phenylcarbamoyl]-phenyl-methyl}-amide |
| 21. | 5-Chloro-thiophene-2-carboxylic acid {[2-fluoro-4-(1-pyrrolidin-1-ylmethyl-cyclopropyl)-phenylcarbamoyl]-phenyl-methyl}-amide |
| 22. | 5-Chloro-thiophene-2-carboxylic acid {(2-fluoro-phenyl)-[4-(1-pyrrolidin-1-ylmethyl-cyclopropyl)-phenylcarbamoyl]-methyl}-amide |
| 23. | 5-Chloro-thiophene-2-carboxylic acid [(4-{dimethylamino-[methanesulfonylimino]-methyl}-phenylcarbamoyl)-phenyl-methyl]-amide |
| 24. | 5-Chloro-thiophene-2-carboxylic acid [(4-{[methanesulfonylimino]-pyrrolidin-1-yl-methyl}-phenylcarbamoyl)-phenyl-methyl]-amide |
| 25. | 5-Chloro-thiophene-2-carboxylic acid {[4-(5,6-dihydro-4H-pyrimidin-1-yl)-phenylcarbamoyl]-phenyl-methyl}-amide |
| 26. | 5-Chloro-thiophene-2-carboxylic acid {[4-(2-methyl-5,6-dihydro-4H-pyrimidin-1-yl)-phenylcarbamoyl]-phenyl-methyl}-amide |
| 27. | 5-Chloro-thiophene-2-carboxylic acid {[4-(2-isopropyl-5,6-dihydro-4H-pyrimidin-1-yl)-phenylcarbamoyl]-phenyl-methyl}-amide |
| 28. | 5-Chloro-thiophene-2-carboxylic acid {phenyl-[4-(2-phenyl-5,6-dihydro-4H-pyrimidin-1-yl)-phenylcarbamoyl]-methyl}-amide |
| 29. | 5-Chloro-thiophene-2-carboxylic acid {[4-(2-acetylamino-5,6-dihydro-4H-pyrimidin-1-yl)-phenylcarbamoyl]-phenyl-methyl}-amide |
| 30. | 5-Chloro-thiophene-2-carboxylic acid {[4-(2-methanesulfonylamino-5,6-dihydro-4H-pyrimidin-1-yl)-phenylcarbamoyl]-phenyl-methyl}-amide |
| 31. | 5-Chloro-thiophene-2-carboxylic acid ({4-[2-(2-oxo-piperidin-1-yl)-5,6-dihydro-4H-pyrimidin-1-yl]-phenylcarbamoyl}-phenyl-methyl)-amide |
| 32. | 3-Chloro-1H-indole-6-carboxylic acid {2-[4-(1-pyrrolidin-1-ylmethyl-cyclopropyl)-benzoylamino]-ethyl}-amide |
| 33. | 3-Chloro-1H-indole-6-carboxylic acid {2-[4-(1-dimethylaminomethyl-cyclopropyl)-benzoylamino]-ethyl}-amide |
| 34. | N-[2-(4-Chloro-phenylcarbamoyl)-ethyl]-4-(1-dimethyl-aminomethyl-cyclopropyl)-benzamide |
| 35. | N-[2-(5-Chloro-pyridin-2-ylcarbamoyl)-ethyl]-4-(1-pyrrolidin-1-ylmethyl-cyclopropyl)-benzamide |
| 36. | N-[2-(5-Chloro-pyridin-2-ylcarbamoyl)-ethyl]-4-(1-dimethyl-aminomethyl-cyclopropyl)-benzamide |
| 37. | N-[2-(3-Chloro-1H-indol-6-ylcarbamoyl)-ethyl]-4-(1-pyrrolidin-1-ylmethyl-cyclopropyl)-benzamide |
| 38. | N-[2-(3-Chloro-1H-indol-6-ylcarbamoyl)-ethyl]-4-(1-dimethylaminomethyl-cyclopropyl)-benzamide |
| 39. | 3-Chloro-1H-indole-6-carboxylic acid {2-[4-(1-pyrrolidin-1-ylmethyl-cyclopropyl)-benzoylamino]-ethyl}-amide |
| 40. | 3-Chloro-1H-indole-6-carboxylic acid {1-methyl-2-[4-(1-pyrrolidin-1-ylmethyl-cyclopropyl)-benzoylamino]-ethyl}-amide |
| 41. | 3-Chloro-1H-indole-6-carboxylic acid {1,1-dimethyl-2-[4-(1-pyrrolidin-1-ylmethyl-cyclopropyl)-benzoylamino]-ethyl}-amide |
| 42. | 3-Chloro-1H-indole-6-carboxylic acid (1-{[4-(1-pyrrolidin-1-ylmethyl-cyclopropyl)-benzoylamino]-methyl}-cyclopentyl)-amide |
| 43. | 3-Chloro-1H-indole-6-carboxylic acid {2-[4-(1-pyrrolidin-1-ylmethyl-cyclopropyl)-benzoylamino]-propyl}-amide |
| 44. | 3-Chloro-1H-indole-6-carboxylic acid {2-methyl-2-[4-(1-pyrrolidin-1-ylmethyl-cyclopropyl)-benzoylamino]-propyl}-amide |
| 45. | 3-Chloro-1H-indole-6-carboxylic acid {3-methyl-2-[4-(1-pyrrolidin-1-ylmethyl-cyclopropyl)-benzoylamino]-butyl}-amide |
| 46. | 3-Chloro-1H-indole-6-carboxylic acid {2-phenyl-2-[4-(1-pyrrolidin-1-ylmethyl-cyclopropyl)-benzoylamino]-ethyl}-amide |
| 47. | 3-Chloro-1H-indole-6-carboxylic acid {3-phenyl-2-[4-(1-pyrrolidin-1-ylmethyl-cyclopropyl)-benzoylamino]-propyl}-amide |
| 48. | 3-[(3-Chloro-1H-indole-6-carbonyl)-amino]-2-[4-(1-pyrrolidin-1-ylmethyl-cyclopropyl)-benzoylamino]-propionic acid methyl ester |
| 49. | 5-Chloro-thiophene-2-carboxylic acid {2-[4-(1-pyrrolidin-1-ylmethyl-cyclopropyl)-benzoylamino]-propyl}-amide |
| 50. | 5-Chloro-thiophene-2-carboxylic acid {2-methyl-2-[4-(1-pyrrolidin-1-ylmethyl-cyclopropyl)-benzoylamino]-propyl}-amide |
| 51. | 5-Chloro-thiophene-2-carboxylic acid {1-methyl-2-[4-(1-pyrrolidin-1-ylmethyl-cyclopropyl)-benzoylamino]-ethyl}-amide |
| 52. | 5-Chloro-thiophene-2-carboxylic acid {1,1-dimethyl-2-[4-(1-pyrrolidin-1-ylmethyl-cyclopropyl)-benzoylamino]-ethyl}-amide |
| 53. | 5-Chloro-thiophene-2-carboxylic acid {3-methyl-2-[4-(1-pyrrolidin-1-ylmethyl-cyclopropyl)-benzoylamino]-butyl}-amide |
| 54. | 5-Chloro-thiophene-2-carboxylic acid {2-phenyl-2-[4-(1-pyrrolidin-1-ylmethyl-cyclopropyl)-benzoylamino]-ethyl}-amide |
| 55. | 3-[(5-Chloro-thiophene-2-carbonyl)-amino]-2-[4-(1-pyrrolidin-1-ylmethyl-cyclopropyl)-benzoylamino]-propionic acid methyl ester |

TABLE 1-continued

| Example | Name |
|---|---|
| 56. | 3-[(5-Chloro-thiophene-2-carbonyl)-amino]-2-[4-(1,1-dimethyl-2-pyrrolidin-1-yl-ethyl)-benzoylamino]-propionic acid methyl ester |
| 57. | 5-Chloro-thiophene-2-carboxylic acid [2-(4-{dimethylamino-[methanesulfonylimino]-methyl}-benzoylamino)-ethyl]-amide |
| 58. | N-[2-(5-Chloro-pyridin-2-ylcarbamoyl)-ethyl]-4-{dimethylamino-[methanesulfonylimino]-methyl}-benzamide |
| 59. | N-[2-(5-Chloro-pyridin-2-ylcarbamoyl)-ethyl]-4-{[methanesulfonylimino]-pyrrolidin-1-yl-methyl}-benzamide |
| 60. | N-[2-(5-Chloro-pyridin-2-ylcarbamoyl)-ethyl]-4-{[methoxyimino]-pyrrolidin-1-yl-methyl}-benzamide |
| 61. | N-[2-(4-Chloro-phenylcarbamoyl)-ethyl]-4-(2-phenyl-5,6-dihydro-4H-pyrimidin-1-yl)-benzamide |
| 62. | N-[2-(4-Chloro-phenylcarbamoyl)-ethyl]-4-(2-ethyl-5,6-dihydro-4H-pyrimidin-1-yl)-benzamide |
| 63. | N-[2-(4-Chloro-phenylcarbamoyl)-ethyl]-4-(2-isopropyl-5,6-dihydro-4H-pyrimidin-1-yl)-benzamide |
| 64. | 5-Chloro-thiophene-2-carboxylic acid [2-(4-{[methanesulfonylimino]-pyrrolidin-1-yl-methyl}-benzoylamino)-ethyl]-amide |
| 65. | 5-Chloro-thiophene-2-carboxylic acid [2-(4-{dimethylamino-[methanesulfonylimino]-methyl}-benzoylamino)-ethyl]-amide |
| 66. | 5-Chloro-thiophene-2-carboxylic acid {2-[4-(N'-methoxy-N,N-dimethyl-carbamimidoyl)-benzoylamino]-ethyl}-amide |
| 67. | 5-Chloro-thiophene-2-carboxylic acid {2-[4-(5,6-dihydro-4H-pyrimidin-1-yl)-benzoylamino]-ethyl}-amide |
| 68. | 5-Chloro-thiophene-2-carboxylic acid {2-[4-(2-isopropyl-5,6-dihydro-4H-pyrimidin-1-yl)-benzoylamino]-ethyl}-amide |
| 69. | 5-Chloro-thiophene-2-carboxylic acid {2-[4-(2-phenyl-5,6-dihydro-4H-pyrimidin-1-yl)-benzoylamino]-ethyl}-amide |
| 70. | 5-Chloro-thiophene-2-carboxylic acid {2-[4-(2-methanesulfonylamino-5,6-dihydro-4H-pyrimidin-1-yl)-benzoylamino]-ethyl}-amide |
| 71. | 5-Chloro-thiophene-2-carboxylic acid (2-{[4-(2-phenyl-5,6-dihydro-4H-pyrimidin-1-yl)-cyclohexanecarbonyl]-amino}-ethyl)-amide |
| 72. | 5-Chloro-thiophene-2-carboxylic acid (2-{[4-(2-methyl-5,6-dihydro-4H-pyrimidin-1-yl)-cyclohexanecarbonyl]-amino}-ethyl)-amide |
| 73. | 5-Chloro-thiophene-2-carboxylic acid (2-{[4-(2-isopropyl-5,6-dihydro-4H-pyrimidin-1-yl)-cyclohexanecarbonyl]-amino}-ethyl)-amide |
| 74. | 5-Chloro-thiophene-2-carboxylic acid {2-[(4-{dimethylamino-[methanesulfonylimino]-methyl}-cyclohexanecarbonyl)-amino]-ethyl}-amide |
| 75. | 5-Chloro-thiophene-2-carboxylic acid {2-[(4-{(butyl-methyl-amino)-[methanesulfonylimino]-methyl}-cyclohexanecarbonyl)-amino]-ethyl}-amide |
| 76. | 5-Chloro-thiophene-2-carboxylic acid (2-{[4-(1-pyrrolidin-1-ylmethyl-cyclopropyl)-cyclohexanecarbonyl]-amino}-ethyl)-amide |
| 77. | 5-Chloro-thiophene-2-carboxylic acid (2-{[4-(1-dimethylaminomethyl-cyclopropyl)-cyclohexanecarbonyl]-amino}-ethyl)-amide |
| 78. | 5-Chloro-thiophene-2-carboxylic acid {phenyl-[4-(1-pyrrolidin-1-ylmethyl-cyclopropyl)-cyclohexylcarbamoyl]-methyl}-amide |
| 79. | 5-Chloro-thiophene-2-carboxylic acid {[4-(1,1-dimethyl-2-pyrrolidin-1-yl-ethyl)-cyclohexylcarbamoyl]-phenyl-methyl}-amide |
| 80. | 5-Chloro-thiophene-2-carboxylic acid {[4-(5,6-dihydro-4H-pyrimidin-1-yl)-cyclohexylcarbamoyl]-phenyl-methyl}-amide |
| 81. | 5-Chloro-thiophene-2-carboxylic acid {[4-(2-methyl-5,6-dihydro-4H-pyrimidin-1-yl)-cyclohexylcarbamoyl]-phenyl-methyl}-amide |
| 82. | 5-Chloro-thiophene-2-carboxylic acid [(4-{dimethylamino-[methanesulfonylimino]-methyl}-cyclohexylcarbamoyl)-phenyl-methyl]-amide |
| 83. | 5-Chloro-thiophene-2-carboxylic acid [(4-{[methanesulfonylimino]-pyrrolidin-1-yl-methyl}-cyclohexylcarbamoyl)-phenyl-methyl]-amide |
| 84. | 5-Chloro-thiophene-2-carboxylic acid [(4-{[methoxyimino]-pyrrolidin-1-yl-methyl}-cyclohexylcarbamoyl)-phenyl-methyl]-amide |
| 85. | 2-[3-(4-Chloro-phenyl)-ureido]-N-(4-{[methanesulfonylimino]-pyrrolidin-1-yl-methyl}-cyclohexyl)-2-phenyl-acetamide |
| 86. | 5-Chloro-thiophene-2-carboxylic acid {phenyl-[4-(1-pyrrolidin-1-ylmethyl-cyclobutyl)-phenylcarbamoyl]-methyl}-amide |
| 87. | 5-Chloro-thiophene-2-carboxylic acid {[4-(1-dimethylaminomethyl-cyclopentyl)-phenylcarbamoyl]-phenyl-methyl}-amide |
| 88. | 5-Chloro-thiophene-2-carboxylic acid {[4-(1,1-dimethyl-2-pyrrolidin-1-yl-ethyl)-phenylcarbamoyl]-phenyl-methyl}-amide |
| 89. | 2-[3-(5-Chloro-thiophen-2-yl)-ureido]-2-phenyl-N-[4-(1-pyrrolidin-1-ylmethyl-cyclopropyl)-phenyl]-acetamide |
| 90. | 2-[3-(5-Chloro-thiophen-2-yl)-ureido]-N-[4-(1-dimethylaminomethyl-cyclopropyl)-phenyl]-2-phenyl-acetamide |
| 91. | 2-[3-(5-Chloro-thiophen-2-yl)-ureido]-N-[4-(1-diethylaminomethyl-cyclopropyl)-phenyl]-2-phenyl-acetamide |

TABLE 1-continued

| Example | Name |
|---|---|
| 92. | 2-[3-(5-Chloro-thiophen-2-yl)-ureido]-N-[4-(1-methylaminomethyl-cyclopropyl)-phenyl]-2-phenyl-acetamide |
| 93. | 2-[3-(5-Chloro-thiophen-2-yl)-ureido]-N-{4-[1-((R)-3-hydroxy-pyrrolidin-1-ylmethyl)-cyclopropyl]-phenyl}-2-phenyl-acetamide |
| 94. | 2-[3-(5-Chloro-thiophen-2-yl)-ureido]-N-[4-(1-morpholin-4-ylmethyl-cyclopropyl)-phenyl]-2-phenyl-acetamide |
| 95. | 2-[3-(5-Chloro-thiophen-2-yl)-ureido]-N-{4-[1-(1,1-dioxo-1$\lambda^6$-thiomorpholin-4-ylmethyl)-cyclopropyl]-phenyl}-2-phenyl-acetamide |
| 96. | 2-[3-(5-Chloro-thiophen-2-yl)-ureido]-N-[4-(1-methanesulfonyl-cyclopropyl)-phenyl]-2-phenyl-acetamide |
| 97. | 2-[3-(5-Chloro-thiophen-2-yl)-ureido]-N-[4-(1,1-dimethyl-2-pyrrolidin-1-yl-ethyl)-phenyl]-2-phenyl-acetamide |
| 98. | 2-[3-(5-Chloro-thiophen-2-yl)-ureido]-2-phenyl-N-[4-(1-pyrrolidin-1-ylmethyl-cyclobutyl)-phenyl]-acetamide |
| 99. | 2-[3-(5-Chloro-thiophen-2-yl)-ureido]-2-phenyl-N-[4-(1-pyrrolidin-1-ylmethyl-cyclopentyl)-phenyl]-acetamide |
| 100. | 2-[3-(5-Chloro-thiophen-2-yl)-ureido]-N-{4-[methyl-(2-pyrrolidin-1-yl-acetyl)-amino]-phenyl}-2-phenyl-acetamide |
| 101. | 2-[3-(5-Chloro-thiophen-2-yl)-ureido]-N-{4-[(2-dimethylamino-acetyl)-methyl-amino]-phenyl}-2-phenyl-acetamide |
| 102. | 2-[3-(5-Chloro-thiophen-2-yl)-ureido]-N-{4-[methyl-(2-morpholin-4-yl-acetyl)-amino]-phenyl}-2-phenyl-acetamide |
| 103. | 2-[3-(5-Chloro-thiophen-2-yl)-ureido]-N-(4-{dimethylamino-[methanesulfonylimino]-methyl}-phenyl)-2-phenyl-acetamide |
| 104. | 2-[3-(5-Chloro-thiophen-2-yl)-ureido]-N-(4-{[methanesulfonylimino]-pyrrolidin-1-yl-methyl}-phenyl)-2-phenyl-acetamide |
| 105. | 2-[3-(5-Chloro-thiophen-2-yl)-ureido]-N-[4-(N'-methoxy-N,N-dimethyl-carbamimidoyl)-phenyl]-2-phenyl-acetamide |
| 106. | (5-Chloro-thiophen-2-yl)-carbamic acid [4-(N'-methoxy-N,N-dimethyl-carbamimidoyl)-phenylcarbamoyl]-phenyl-methyl ester |
| 107. | (5-Chloro-thiophen-2-yl)-carbamic acid (4-{dimethylamino-[methanesulfonylimino]-methyl}-phenylcarbamoyl)-phenyl-methyl ester |
| 108. | (5-Chloro-thiophen-2-yl)-carbamic acid (4-{[methanesulfonylimino]-pyrrolidin-1-yl-methyl}-phenylcarbamoyl)-phenyl-methyl ester |
| 109. | (5-Chloro-thiophen-2-yl)-carbamic acid [4-(1-morpholin-4-ylmethyl-cyclopropyl)-phenylcarbamoyl]-phenyl-methyl ester |
| 110. | (5-Chloro-thiophen-2-yl)-carbamic acid {4-[1-((R)-3-hydroxy-pyrrolidin-1-ylmethyl)-cyclopropyl]-phenylcarbamoyl}-phenyl-methyl ester |
| 111. | (5-Chloro-thiophen-2-yl)-carbamic acid [4-(1-dimethylaminomethyl-cyclopropyl)-phenylcarbamoyl]-phenyl-methyl ester |
| 112. | (5-Chloro-thiophen-2-yl)-carbamic acid phenyl-[4-(1-pyrrolidin-1-ylmethyl-cyclopropyl)-phenylcarbamoyl]-methyl ester |
| 113. | (5-Chloro-thiophen-2-yl)-carbamic acid phenyl-[4-(1-pyrrolidin-1-ylmethyl-cyclobutyl)-phenylcarbamoyl]-methyl ester |
| 114. | (5-Chloro-thiophen-2-yl)-carbamic acid [4-(1,1-dimethyl-2-pyrrolidin-1-yl-ethyl)-phenylcarbamoyl]-phenyl-methyl ester |
| 115. | (5-Chloro-thiophen-2-yl)-carbamic acid {4-[methyl-(2-pyrrolidin-1-yl-acetyl)-amino]-phenylcarbamoyl}-phenyl-methyl ester |
| 116. | (5-Chloro-thiophen-2-yl)-carbamic acid {4-[(2-dimethylamino-acetyl)-methyl-amino]-phenylcarbamoyl}-phenyl-methyl ester |
| 117. | N-[2-(5-Chloro-pyridin-2-ylcarbamoyl)-ethyl]-4-( 1-pyrrolidin-1-ylmethyl-cyclopropyl)-benzamide |
| 118. | N-[2-(5-Chloro-pyridin-2-ylcarbamoyl)-ethyl]-4-(1-dimethylaminomethyl-cyclopropyl)-benzamide |
| 119. | N-[2-(5-Chloro-pyridin-2-ylcarbamoyl)-1-methyl-ethyl]-4-(1-pyrrolidin-1-ylmethyl-cyclopropyl)-benzamide |
| 120. | N-{1-[(5-Chloro-pyridin-2-ylcarbamoyl)-methyl]-2-methyl-propyl}-4-(1-pyrrolidin-1-ylmethyl-cyclopropyl)-benzamide |
| 121. | N-[2-(5-Chloro-pyridin-2-ylcarbamoyl)-1-phenyl-ethyl]-4-(1-pyrrolidin-1-ylmethyl-cyclopropyl)-benzamide |
| 122. | N-[2-(5-Chloro-pyridin-2-ylcarbamoyl)-ethyl]-4-(2-methyl-5,6-dihydro-4H-pyrimidin-1-yl)-benzamide |
| 123. | N-[2-(5-Chloro-pyridin-2-ylcarbamoyl)-ethyl]-4-[methyl-(2-pyrrolidin-1-yl-acetyl)-amino]-benzamide |
| 124. | 5-Chloro-thiophene-2-carboxylic acid {1-[4-(1-pyrrolidin-1-ylmethyl-cyclopropyl)-phenylcarbamoyl]-pentyl}-amide |
| 125. | 5-Chloro-thiophene-2-carboxylic acid {cyclohexyl-[4-(1-pyrrolidin-1-ylmethyl-cyclopropyl)-phenylcarbamoyl]-methyl}-amide |
| 126. | 5-Chloro-thiophene-2-carboxylic acid {3-methyl-1-[4-(1-pyrrolidin-1-ylmethyl-cyclopropyl)-phenylcarbamoyl]-butyl}-amide |
| 127. | 5-Chloro-thiophene-2-carboxylic acid ({4-[1-((R)-3-hydroxy-pyrrolidin-1-ylmethyl)-cyclopropyl]-phenylcarbamoyl}-phenyl-methyl)-amide |
| 128. | 5-Chloro-thiophene-2-carboxylic acid {[4-(1-diethylaminomethyl-cyclopropyl)-phenylcarbamoyl]-phenyl-methyl}-amide |
| 129. | 5-Chloro-thiophene-2-carboxylic acid {[4-(1-methanesulfonyl-cyclopropyl)-phenylcarbamoyl]-phenyl-methyl}-amide |
| 130. | 5-Chloro-thiophene-2-carboxylic acid {[4-(1-methoxymethyl-cyclopropyl)-phenylcarbamoyl]-phenyl-methyl}-amide |

TABLE 1-continued

| Example | Name |
|---|---|
| 131. | 5-Chloro-thiophene-2-carboxylic acid {phenyl-[4-(1-pyrrolidin-l-yl-cyclopropyl)-phenylcarbamoyl]-methyl}-amide |
| 132. | 5-Chloro-thiophene-2-carboxylic acid {[4-(1-dimethylamino-cyclopropyl)-phenylcarbamoyl]-phenyl-methyl}-amide |
| 133. | 5-Chloro-thiophene-2-carboxylic acid {[4-(1-methylamino-cyclopropyl)-phenylcarbamoyl]-phenyl-methyl}-amide |
| 134. | 5-Chloro-thiophene-2-carboxylic acid {[4-(1-amino-cyclopropyl)-phenylcarbamoyl]-phenyl-methyl}-amide |
| 135. | 5-Chloro-thiophene-2-carboxylic acid ({4-[1-(2-dimethylamino-ethyl)-cyclopropyl]-phenylcarbamoyl}-phenyl-methyl)-amide |
| 136. | 5-Chloro-thiophene-2-carboxylic acid (phenyl-{4-[1-(2-pyrrolidin-1-yl-ethyl)-cyclopropyl]-phenylcarbamoyl}-methyl)-amide |
| 137. | 5-Chloro-thiophene-2-carboxylic acid ({4-[1-(2-morpholin-4-yl-ethyl)-cyclopropyl]-phenylcarbamoyl}-phenyl-methyl)-amide |
| 138. | 5-Chloro-thiophene-2-carboxylic acid {[4-(1-carbamoylmethyl-cyclopropyl)-phenylcarbamoyl]-phenyl-methyl}-amide |
| 139. | 2-[3-(4-Chloro-phenyl)-ureido]-2-phenyl-N-[4-(1-pyrrolidin-1-ylmethyl-cyclopropyl)-phenyl]-acetamide |
| 140. | 2-[3-(4-Chloro-phenyl)-ureido]-N-[4-(1-dimethylaminomethyl-cyclopropyl)-phenyl]-2-phenyl-acetamide |
| 141. | 2-[3-(4-Chloro-phenyl)-ureido]-N-[4-(1-diethylaminomethyl-cyclopropyl)-phenyl]-2-phenyl-acetamide |
| 142. | 2-[3-(4-Chloro-phenyl)-ureido]-N-{4-[1-(2-dimethylamino-ethyl)-cyclopropyl]-phenyl}-2-phenyl-acetamide |
| 143. | 2-[3-(4-Chloro-phenyl)-ureido]-N-[4-(1-dimethylaminomethyl-cyclobutyl)-phenyl]-2-phenyl-acetamide |
| 144. | 2-[3-(4-Chloro-phenyl)-ureido]-N-{4-[methyl-(2-pyrrolidin-1-yl-acetyl)-amino]-phenyl}-2-phenyl-acetamide |
| 145. | 2-[3-(4-Chloro-phenyl)-ureido]-N-[4-(5,6-dihydro-4H-pyrimidin-1-yl)-phenyl]-2-phenyl-acetamide |
| 146. | 2-[3-(4-Chloro-phenyl)-ureido]-N-(4-{dimethylamino-[methanesulfonylimino]-methyl}-phenyl)-2-phenyl-acetamide |

Numerous modifications and variations of the present invention are possible in light of the above teachings. It is therefore to be understood that within the scope of the appended claims, the invention may be practiced otherwise that as specifically described herein.

What is claimed is:

1. A compound is selected from:

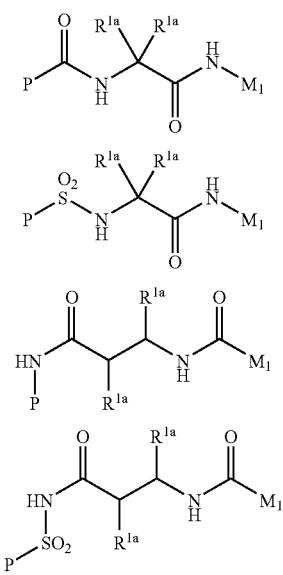

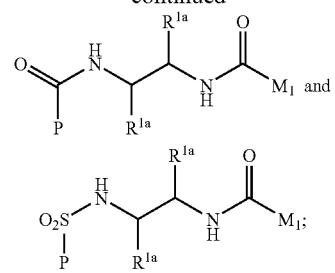

or a stereoisomer or pharmaceutically acceptable salt thereof, wherein;

P is selected from phenyl, pyridyl, thienyl, and indolyl; and P is substituted with 1-3 R;

$M_1$ is -A-B;

R is independently at each occurrence, selected from H, $C_{1-4}$ alkyl, F, Cl, Br, I, OH, —$OCH_3$, —$OCH_2CH_3$, —$OCH(CH_3)_2$, —$OCH_2CH_2CH_3$, CN, —C(=$NR^8$)$NR^7R^9$, —NHC(=$NR^8$)$NR^7R^9$, —ONHC(=$NR^8$)$NR^7R^9$, —$NR^8$CH(=$NR^7$), $NH_2$, —NH($C_{1-3}$ alkyl), —N($C_{1-3}$ alkyl)$_2$, —C(=NH)$NH_2$, —$CH_2NH_2$, —$CH_2$NH($C_{1-3}$ alkyl), —$CH_2$N($C_{1-3}$ alkyl)$_2$, —$CH_2CH_2NH_2$, —$CH_2CH_2$NH($C_{1-3}$ alkyl), —$CH_2CH_2$N($C_{1-3}$ alkyl)$_2$, —$(CR^8R^9)_rC(O)H$, —$(CR^8R^9)_rC(O)R^{2c}$, —$(CR^8R^9)_rNR^7R^8$, —$(CR^8R^9)_rC(O)NR^7R^8$, —$(CR^8R^9)_rNR^7C(O)R^7$, —$(CR^8R^9)_rOR^3$, —$(CR^8R^9)_rS(O)_pNR^7R^8$, —$(CR^8R^9)_rNR^7S(O)_pR^7$, —$(CR^8R^9)_rSR^3$, —$(CR^8R^9)_rS(O)R^3$, —$(CR^8R^9)_rS(O)_2R^3$, and —$OCF_3$;

A is phenyl substituted with 0-2 R$^4$;

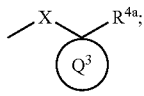

B is
X is absent;
ring Q$^3$ is a C$_{3-6}$ cycloalkyl substituted with 0-2 R$^4$;
R$^{1a}$ is, independently at each occurrence, selected from H, R$^{1b}$, —C(CH$_3$)$_2$R$^{1b}$, —CH(CH$_3$)R$^{1b}$, —CH$_2$R$^{1b}$, and —CH$_2$CH$_2$R$^{1b}$;
R$^{1b}$ is, independently at each occurrence, selected from H, CH$_3$, CH$_2$CH$_3$, F, Cl, Br, CN, CF$_3$, and phenyl;
R$^2$ is, independently at each occurrence, selected from H, CH$_3$, —CH$_2$CH$_3$, —CH$_2$CH$_2$CH$_3$, —CH(CH$_3$)$_2$, phenyl substituted with 0-1 R$^{4b}$, benzyl substituted with 0-1 R$^{4b}$, and 5-6 membered aromatic heterocycle consisting of: carbon atoms and 1-4 heteroatoms selected from N, O, and S(O)$_p$, and substituted with 0-1 R$^{4b}$;
R$^{2a}$ is, independently at each occurrence, selected from H, CH$_3$, —CH$_2$CH$_3$, —CH$_2$CH$_2$CH$_3$, —CH(CH$_3$)$_2$, benzyl, phenyl substituted with 0-1 R$^{4b}$, and 5-6 membered aromatic heterocycle consisting of: carbon atoms and 1-4 heteroatoms selected from N, O, and S(O)$_p$, and substituted with 0-1 R$^{4b}$;
R$^{2b}$ is, independently at each occurrence, selected from —OCH$_3$, —OCH$_2$CH$_3$, —OCH$_2$CH$_2$CH$_3$, —OCH(CH$_3$)$_2$, CH$_3$, —CH$_2$CH$_3$, —CH$_2$CH$_2$CH$_3$, —CH(CH$_3$)$_2$, benzyl, phenyl substituted with 0-1 R$^{4b}$, and 5-6 membered aromatic heterocycle consisting of: carbon atoms and 1-4 heteroatoms selected from N, O, and S(O)$_p$, and substituted with 0-1 R$^{4b}$;
R$^{2c}$ is, independently at each occurrence, selected from OH, —OCH$_3$, —OCH$_2$CH$_3$, —OCH$_2$CH$_2$CH$_3$, —OCH(CH$_3$)$_2$, CH$_3$, —CH$_2$CH$_3$, —CH$_2$CH$_2$CH$_3$, —CH(CH$_3$)$_2$, benzyl, phenyl substituted with 0-1 R$^{4b}$, and 5-6 membered aromatic heterocycle containing from 1-4 heteroatoms selected from N, O, and S(O)$_p$, and substituted with 0-1 R$^{4b}$;
R$^{2d}$ is, independently at each occurrence, selected from H, R$^{4c}$, C$_{1-4}$ alkyl substituted with 0-2 R$_{4c}$, C$_{3-6}$ carbocycle substituted with 0-2 R$^{4c}$, —(CH$_2$)—C$_{3-6}$ carbocycle substituted with 0-2 R$^{4c}$, 5-6 membered heterocycle substituted with 0-2 R$^{4c}$ and consisting of: carbon atoms and 1-4 heteroatoms selected from N, O, and S(O)$_p$, and —(CH$_2$)-5-6 membered heterocycle substituted with 0-2 R$^{4c}$ and consisting of: carbon atoms and 1-4 heteroatoms selected from N, O, and S(O)$_p$, provided that R$^{2d}$ forms other than a N-halo, N—C-halo, S(O)$_p$-halo, O-halo, N—S, S—N, S(O)$_p$,—S(O)$_p$, S—O, O—N, O,—S, or O—O moiety;
alternatively, NR$^{2d}$R$^{2d}$ forms a 5 or 6 membered saturated, partially saturated, or unsaturated ring substituted with 0-1 R$^{4b}$ and consisting of: 0-1 additional heteroatoms selected from N, O, and S(O)$_p$;
R$^{2e}$ is, independently at each occurrence, selected from H, R$^{4c}$, C$_{1-4}$ alkyl substituted with 0-2 R$^{4c}$, C$_{3-6}$ carbocycle substituted with 0-2 R$^{4c}$, —(CH$_2$)—C$_{3-6}$ carbocycle substituted with 0-2 R$^{4c}$, 5-6 membered heterocycle substituted with 0-2 R$^{4c}$ and consisting of: carbon atoms and 1-4 heteroatoms selected from N, O, and S(O)$_p$, and —(CH2)-5-6 membered heterocycle and consisting of: carbon atoms and 1-4 heteroatoms selected from N, O, and S(O)$_p$, provided that R$^{2e}$ forms other than a C(O)-halo or C(O)—S(O)$_p$ moiety;
R$^3$ is, independently at each occurrence, selected from H, CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$) CH$_2$CH$_3$, —C(CH$_3$)$_3$, benzyl, and phenyl;
R$^{3a}$ is, independently at each occurrence, selected from H, CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$) CH$_2$CH$_3$, —C(CH$_3$)$_3$, benzyl, and phenyl;
R$^{3c}$ is, independently at each occurrence, selected from CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$) CH$_2$CH$_3$, —C(CH$_3$)$_3$, benzyl, and phenyl;
R$^{3g}$ is, independently at each occurrence, selected from H, CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$,—CH(CH$_3$) CH$_2$CH$_3$, —C(CH$_3$)$_3$, —(CH$_2$)$_r$—C$_{3-6}$ carbocycle, and —(CH$_2$)$_r$-5-6 membered heterocycle consisting of: carbon atoms and 1-4 heteroatoms selected from N, O, and S(O)$_p$;
R$^4$ is, independently at each occurrence, selected from H, =O , —OR$^2$, —CH$_2$OR$^2$, —(CH$_2$)$_2$OR$^2$, F, Br, Cl, I, CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$) CH$_2$CH$_3$, —C(CH$_3$)$_3$, —NR$^2$R$^{2a}$, —CH$_2$NR$^2$R$^{2a}$, —(CH$_2$)$_2$NR$^2$R$^{2a}$, —C(O)R$^{2c}$, —NR$^2$C(O)R$^{2b}$, —C(O)NR$^2$R$^{2a}$, —SO$_2$NR$^2$R$^{2a}$, CF$_3$, and —CF$_2$CF$_3$;
R$^{4a}$ is selected from —(CR$^3$R$^{3g}$)$_r$—C$_{5-6}$ carbocycle substituted with 0-3 R$^{4c}$, and —(CR$^3$R$^{3g}$)$_r$-5-6 membered heterocycle substituted with 0-3 R$^{4c}$ and consisting of: carbon atoms and 1-4 heteroatoms selected from N, O, and S(O)$_p$;
alternatively, R$^{4a}$ is selected from —(CR$^3$R$^{3g}$)$_r$NR$^{2d}$R$^{2d}$, —(CR$^3$R$^{3g}$)$_r$N(→O)R$^{2d}$R$^{2d}$, —(CR$^3$R$^{3g}$)$_r$OR$^{2d}$, —(CR$^3$R$^{3g}$)$_r$—C(O)NR$^{2d}$R$^{2d}$, —(CR$^3$R$^{3g}$)$_r$—NR$_{2d}$C (O)R$^{2e}$, —(CR$^3$R$^{3g}$)$_r$—C(O)R$^{2e}$, —(CR$^3$R$^{3g}$)$_r$—NR$^{2d}$C(O)NR$^{2d}$R$^{2d}$, —(CR$^3$R$^{3g}$)$_r$—NR$^{2d}$C(O)OR$^{2d}$, —(CR$^3$R$^{3g}$)$_r$—NR$^{2d}$SO$_2$R$^{2d}$, and —(CR$^3$R$^{3g}$)$_r$—S(O)$_p$R$^{2d}$, provided that —S(O)$_p$R$^{2d}$ forms other than —S(O)$_2$ H or —S(O)H;
R$^{4b}$ is, independently at each occurrence, selected from H, =O, —OR$^3$, —CH$_2$OR$^3$, F, Cl, CH$_3$, —CH$_2$CH$_3$, —CH$_2$CH$_2$CH$_3$, —CH(CH$_3$)$_2$, CN, NO$_2$, —NR$^3$R$^{3a}$, —CH$_2$NR$^3$R$^{3a}$, —C(O)R$^3$, —C(O)OR$^{3c}$, —NR$^3$C(O) R$^{3a}$, —C(O)NR$^3$R$^{3a}$, —SO$_2$NR$^3$R$^{3a}$, —NR$_3$SO$_2$—C$_{1-4}$ alkyl, —NR$^3$SO$_2$-phenyl, —S(O)$_p$—C$_{1-4}$ alkyl, —S(O)$_p$-phenyl, and CF$_3$;
R$^{4c}$ is, independently at each occurrence, selected from =O, —(CR$^3$R$^{3a}$)$_r$OR$^2$, —(CR$^3$R$^{3a}$)$_r$F, —(CR$^3$R$^{3a}$)$_r$Br, —(CR$^3$R$^{3a}$)$_r$Cl, —(CR$^3$R$^{3a}$)$_r$CF$_3$, C$_{1-4}$ alkyl, C$_{2-6}$ alkenyl, C$_{2-6}$ alkynyl, —(CR$^3$R$^{3a}$)$_r$CN, —(CR$^3$R$^{3a}$)$_r$NO$_2$, —(CR$^3$R$^{3a}$)$_r$NR$^2$R$^{2a}$,—(CR$^3$R$^{3a}$)$_r$N(→O)R$^2$R$^{3a}$, —(CR$^3$R$^{3a}$)$_r$C(O)R$^{2c}$, —(CR$^3$R$^{3a}$)$_r$NR$^2$C(O)R$^{2b}$, —(CR$^3$R$^{3a}$)$_r$C(O)NR$^2$R$^{2a}$, —(CR$^3$R$^{3a}$)$_r$N=CHOR$^3$, —(CR$^3$R$^{3a}$)$_r$C(O)NR$^2$(CH$_2$)$_2$NR$^2$R$^{2a}$, —(CR$^3$R$^{3a}$)$_r$NR$^2$C(O)NR$^2$R$^{2a}$, —(CR$^3$R$^{3a}$)$_r$C(=NR$^2$)NR$^2$R$^{2a}$, —(CR$^3$R$^{3a}$)$_r$NR$^2$C(=NR$^2$)NR$^2$R$^{2a}$, —(CR$^3$R$^{3a}$)$_r$SO$_2$NR$^2$R$^{2a}$, —(CR$^3$R$^{3a}$)$_r$NR$^2$SO$_2$NR$^2$R$^{2a}$, —(CR$_3$R$^{3a}$)$_r$C(O)NR$^2$SO$_2$—C$_{1-4}$ alkyl, —(CF$_2$)$_r$CF$_3$, —(CR$_3$R$^{3a}$)$_r$C$_{3-10}$ carbocycle substituted with 0-2 R$^{4b}$, and —(CR$^3$R$^{3a}$)$_r$4-10 membered heterocycle substituted with 0-2 R$^{4b}$ and consisting of carbon atoms and 1-4 heteroatoms selected from N, O, and S(O)$_p$;
R$^7$ is, independently at each occurrence, selected from H, OH, C$_{1-6}$ alkyl, C$_{1-6}$ alkyl-C(O)—, C$_{1-6}$ alkyl-O—, —(CH$_2$)$_n$-phenyl, C$_{1-4}$ alkyl-OC(O)—, C$_{6-10}$ aryl-O—, $C_{6-10}$ aryl-OC(O)—, $C_{6-10}$ aryl-CH$_2$—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-NH$_2$—C(O)—, phenyl-NH$_2$—C(O)—, and phenyl $C_{1-4}$ alkyl-C(O)—;

$R^8$ is, independently at each occurrence, selected from H, $C_{1-6}$ alkyl, and —(CH$_2$)$_n$-phenyl;

alternatively, $R^7$ and $R^8$, when attached to the same nitrogen, combine to form a 5-10 membered heterocyclic ring consisting of carbon atoms and 0-2 additional heteroatoms selected from N, O, and S(O)$_p$;

$R^9$ is, independently at each occurrence, selected from H, $C_{1-6}$ alkyl, and —(CH$_2$)$_n$-phenyl;

n, at each occurrence, is selected from 0, 1, 2, and 3;
p, at each occurrence, is selected from 0, 1, and 2;
r, at each occurrence, is selected from 0, 1, 2, 3, 4, 5, and 6; and
t, at each occurrence, is selected from 0, 1, 2, and 3.

2. A compound according to claim 1, wherein:
R is, independently at each occurrence, selected from H, $C_{1-4}$ alkyl, F, Cl, OH, —OCH$_3$, —OCH$_2$CH$_3$, —OCH(CH$_3$)$_2$, CN, —C(=NH)NH$_2$, —C(=NH)NHOH, —C(=NH)NHOCH$_3$, NH$_2$, —NH(C$_{1-3}$ alkyl), —N(C$_{1-3}$ alkyl)$_2$, —C(=NH)NH$_2$, —CH$_2$NH$_2$, —CH$_2$NH(C$_{1-3}$ alkyl), —CH$_2$N(C$_{1-3}$ alkyl)$_2$, C(=NR$^8$)NR$^7$R$^9$, —(CR$^8$R$^9$)$_r$NR$^7$R$^8$, —C(O)NR$^7$R$^8$, —CH$_2$C(O)NR$^7$R$^8$, —S(O)$_2$R$^3$, —S(O)$_p$NR$^7$R$^8$, —CH$_2$S(O)$_p$NR$^7$R$^8$, and —OCF$_3$;

$R^3$ is, independently at each occurrence, selected from H, CH$_3$, —CH$_2$CH$_3$, —CH$_2$CH$_2$CH$_3$, —CH(CH$_3$)$_2$, benzyl, and phenyl;

$R^{3a}$ is, independently at each occurrence, selected from H, CH$_3$, —CH$_2$CH$_3$, —CH$_2$CH$_2$CH$_3$, —CH(CH$_3$)$_2$, benzyl, and phenyl;

$R^{3c}$ is, independently at each occurrence, selected from CH$_3$, —CH$_2$CH$_3$, —CH$_2$CH$_2$CH$_3$, —CH(CH$_3$)$_2$, benzyl, and phenyl; and $R^{4c}$ is, independently at each occurrence, selected from =O, —(CR$^3$R$^{3a}$)$_r$OR$^2$, —(CR$^3$R$^{3a}$)$_r$F, —(CR$^3$R$^{3a}$)$_r$Br, —(CR$^3$R$^{3a}$)$_r$Cl, —(CR$^3$R$^{3a}$)$_r$CF$_3$, $C_{1-4}$ alkyl, $C_{2-3}$ alkenyl, $C_{2-3}$ alkynyl, —(CR$^3$R$^{3a}$)$_r$CN, —(CR$^3$R$^{3a}$)$_r$NO$_2$, —(CR$^3$R$^{3a}$)$_r$NR$^2$R$^{2a}$, —(CR$^3$R$^{3a}$)$_r$N(→O)R$^2$R$^{2a}$, —(CR$^3$R$^{3a}$)$_r$C(O)R$^{2c}$, —(CR$^3$R$^{3a}$)$_r$NR$^2$C(O)R$^{2b}$, —(CR$^3$R$^{3a}$)$_r$C(O)NR$^2$R$^{2a}$, —(CR$^3$R$^{3a}$)$_r$NR$^2$C(O)NR$^2$R$^{2a}$, —(CR$^3$R$^{3a}$)$_r$SO$_2$NR$^2$R$^{2a}$, —(CR$^3$R$^{3a}$)$_r$NR$^2$SO$_2$NR$^2$R$^{2a}$, —(CF$_2$)$_r$CF$_3$, —(CR$^3$R$^{3a}$)$_r$C$_{3-10}$ carbocycle substituted with 0-2 R$^{4b}$, and —(CR$^3$R$^{3a}$)$_r$5-10 membered heterocycle consisting of carbon atoms and 1-4 heteroatoms selected from N, O, and S(O)$_p$, and substituted with 0-2 R$^{4b}$.

3. A compound according to claim 2, wherein:
P is selected from the group:

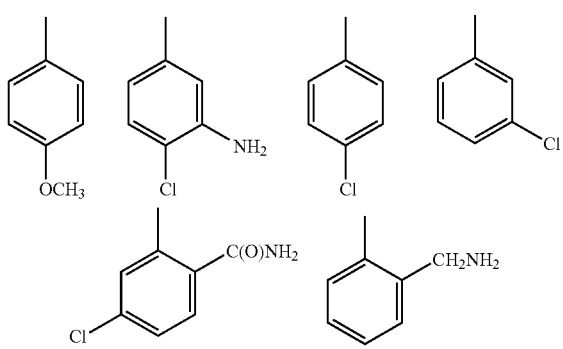

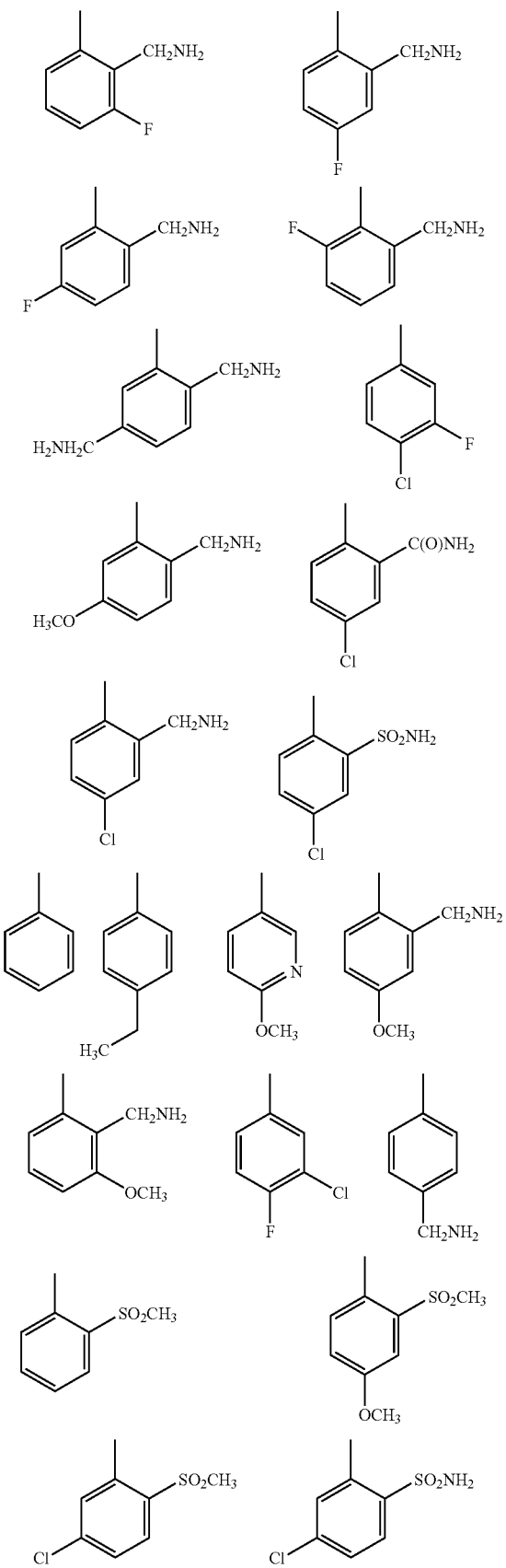

-continued

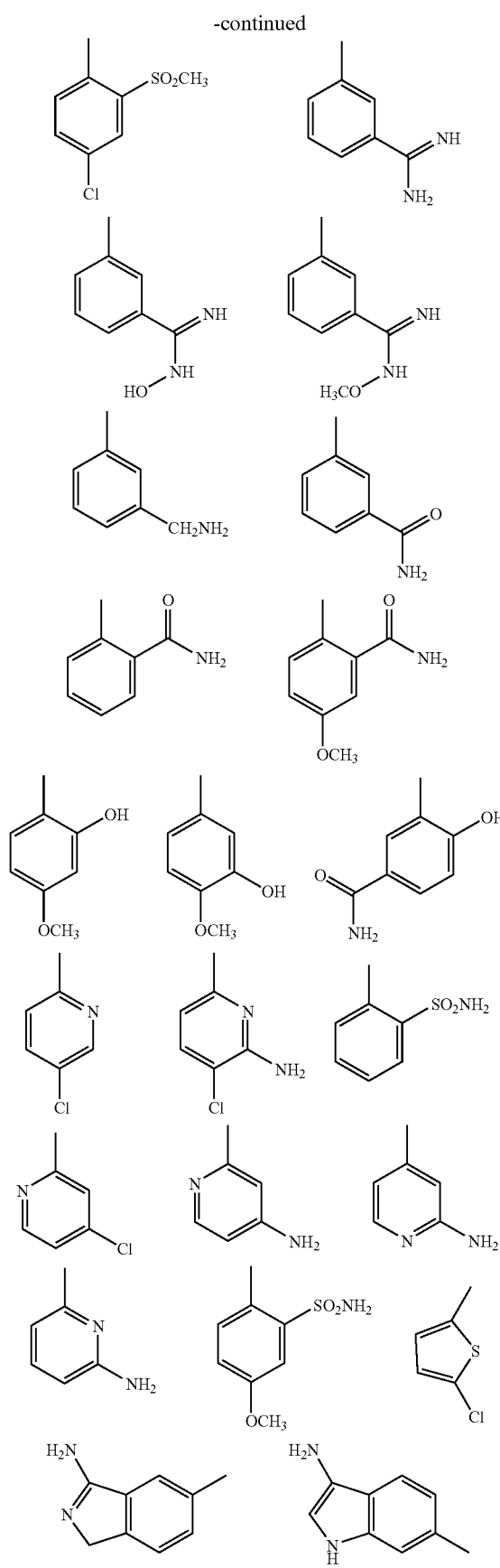

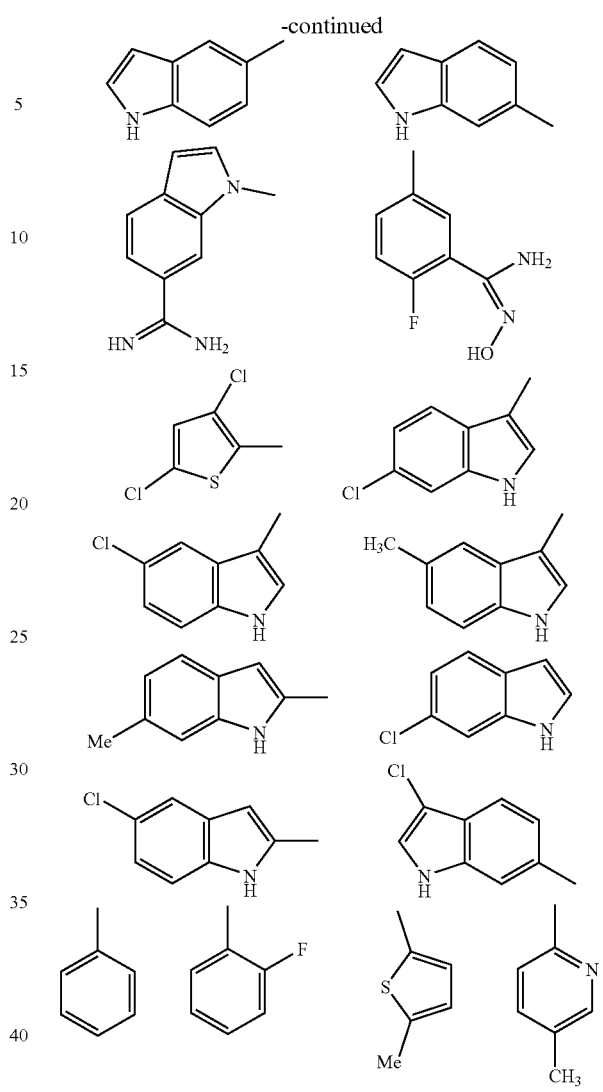

R$^{4c}$ is, independently at each occurrence, selected from =O, OR$^2$, —(CR$^3$R$^{3a}$)OR$^2$, F, —(CR$^3$R$^{3a}$)F, Br, —(CR$^3$R$^{3a}$)Br, Cl, —(CR$^3$R$^{3a}$)Cl, CF$_3$, —(CR$^3$R$^{3a}$)CF$_3$, C$_{2-3}$ alkenyl, C$_{2-3}$ alkynyl, C$_{1-4}$ alkyl, CN, —(CR$^3$R$^{3a}$)CN, NO$_2$, —(CR$^3$R$^{3a}$)NO$_2$, —NR$^2$R$^{2a}$, —(CR$^3$R$^{3a}$)NR$^2$R$^{2a}$, —N(→O)R$^2$R$^{2a}$, —(CR$^3$R$^{3a}$)N(→O)R$^2$R$^{2a}$, —C(O)R$^{2c}$, —(CR$^3$R$^{3a}$)C(O)R$^{2c}$, —NR$^2$C(O)R$^{2b}$, —(CR$^3$R$^{3a}$)NR$^2$C(O)R$^{2b}$, —C(O)NR$^2$R$^{2a}$, —(CR$^3$R$^{3a}$)C(O)NR$^2$R$^{2a}$, —NR$^2$C(O)NR$^2$R$^{2a}$, —(CR$^3$R$^{3a}$)NR$^2$C(O)NR$^2$R$^{2a}$, —SO$_2$NR$^2$R$^{2a}$, —(CR$^3$R$^{3a}$)SO$_2$NR$^2$R$^{2a}$, —NR²SO₂NR²R²ᵃ, —(CR³R³ᵃ)NR²SO₂NR²R²ᵃ, CF₃, —CF₂CF₃, C₃₋₁₀ carbocycle substituted with 0-2 R⁴ᵇ, —(CR³R³ᵃ)C₃₋₁₀ carbocycle substituted with 0-2 R⁴ᵇ, 5-10 membered heterocycle consisting of carbon atoms and 1-4 heteroatoms selected from N, O, and S(O)ₚ, and substituted with 0-2 R⁴ᵇ, and —(CR³R³ᵃ)-5-10 membered heterocycle consisting of carbon atoms and 1-4 heteroatoms selected from N, O, and S(O)ₚ, and substituted with 0-2 R⁴ᵇ.

4. A compound according to claim 3, wherein:

P is selected from:

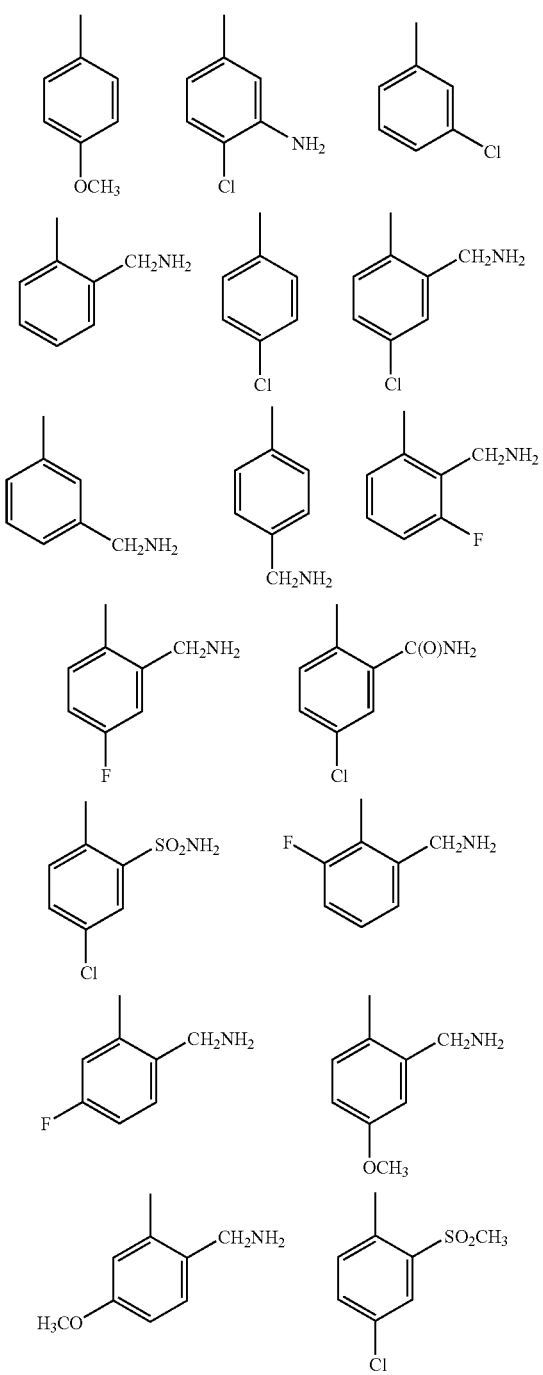

-continued

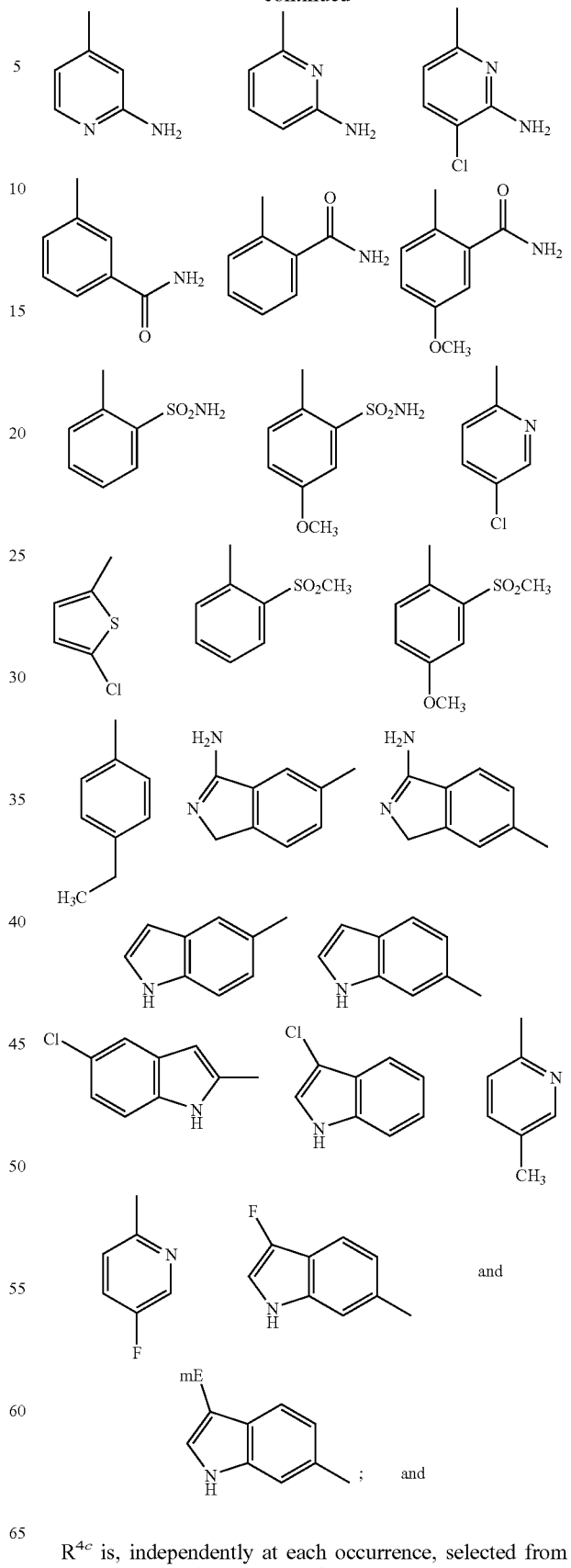

R⁴ᶜ is, independently at each occurrence, selected from =O, —OR², —CH₂OR², F, Br, Cl, CF₃, CH₃, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, C$_{2-3}$ allenyl, C$_{2-3}$ alkynyl, CN, NO$_2$, —NR$^2$R$^{2a}$, —CH$_2$NR$^2$R$^{2a}$, —N(→O)R$^2$R$^{2a}$, —CH$_2$N(→O)R$^2$R$^{2a}$, —C(O)R$^{2c}$, —CH$_2$C(O)R$^{2c}$, —NR$^2$C(O)R$^{2b}$, —CH$_2$NR$^2$C(O)R$^{2b}$, —C(O)NR$^2$R$^{2a}$, —CH$_2$C(O)NR$^2$R$^{2a}$, —SO$_2$NR$^2$R$^{2a}$, CF$_3$, —CF$_2$CF$_3$, C$_{3-6}$ carbocycle substituted with 0-2 R$^{4b}$, —(CH$_2$)C$_{3-6}$ carbocycle substituted with 0-2 R$^{4b}$, 5-6 membered heterocycle consisting of carbon atoms and 1-4 heteroatoms selected from N, O, and S(O)$_p$, and substituted with 0-2 R$^{4b}$, and —(CH2)-5-6 membered heterocycle consisting of carbon atoms and 1-4 heteroatoms selected from N, O, and S(O)$_p$, and substituted with 0-2 R$^{4b}$.

5. A compound according to claim 4, wherein:
P is selected from:

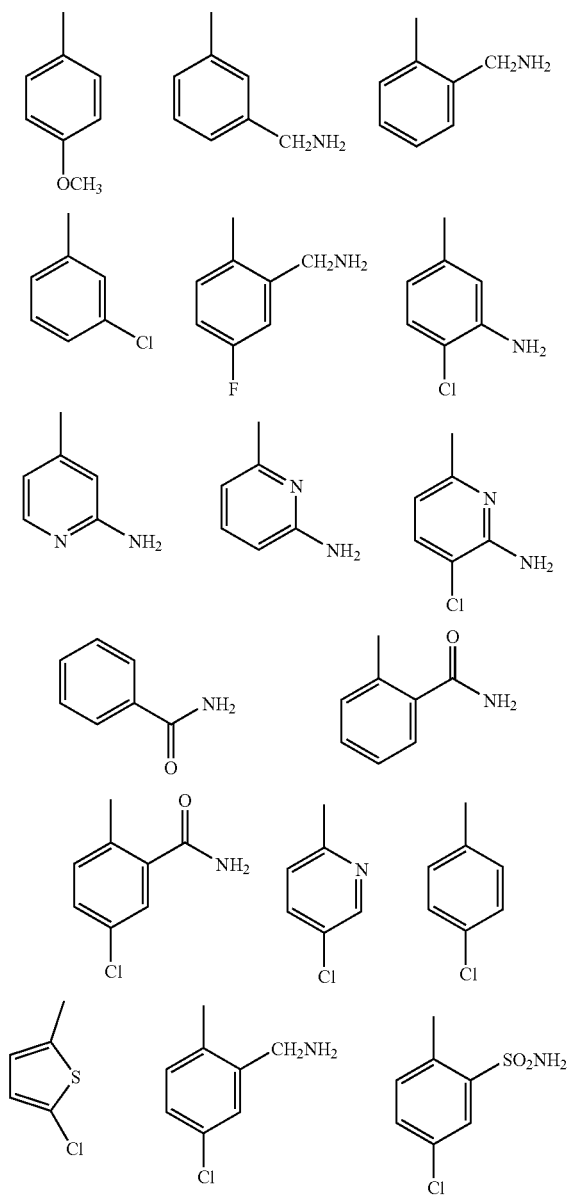

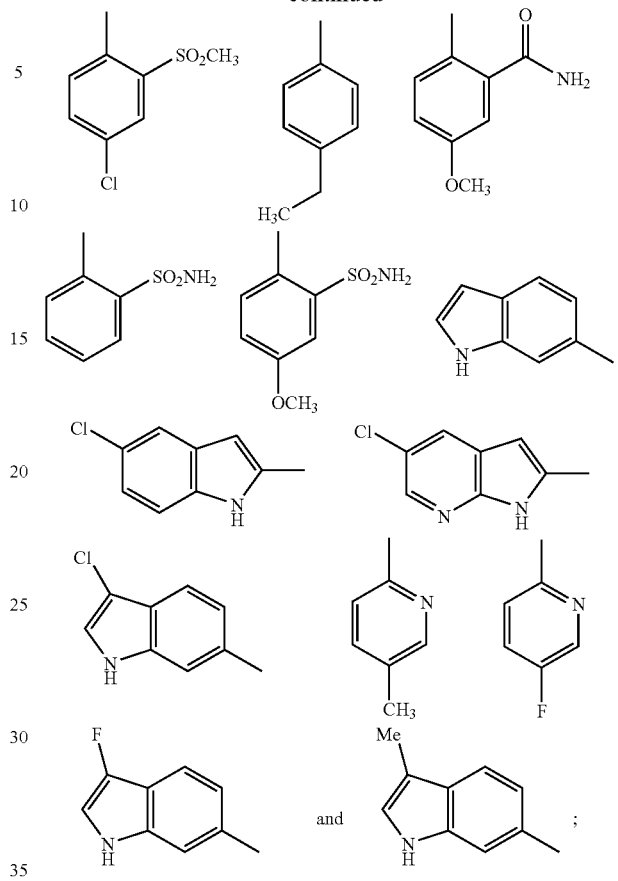

A is selected from the group: phenyl, 2-Cl-phenyl, 3-Cl-phenyl, 2-F-phenyl, 3-F-phenyl, 2-methylphenyl, 2-aminophenyl, and 2-methoxyphenyl;

ring Q$^3$ is selected from cyclopropyl, cyclobutyl, cyclopentyl, and cyclohexyl;

R$^{1a}$ is, independently at each occurrence, selected from H, CH$_3$, —CH$_2$CH$_3$, —CH$_2$CH$_2$CH$_3$, and —CH$_2$(CH$_3$)$_2$;

R$^2$ is, independently at each occurrence, selected from H, CH$_3$, —CH$_2$CH$_3$, —CH$_2$CH$_2$CH$_3$, —CH(CH$_3$)$_2$, phenyl substituted with 0-1 R$^{4b}$, benzyl substituted with 0-1 R$^{4b}$, and a 5 membered aromatic heterocycle consisting of: carbon atoms and 1-4 heteroatoms selected from N, O, and S(O)$_p$, and substituted with 0-1 R$^{4b}$;

R$^{2a}$ is, independently at each occurrence, selected from H, CH$_3$, and —CH$_2$CH$_3$;

R$^{2b}$ is, independently at each occurrence, selected from —OCH$_3$, —OCH$_2$CH$_3$, CH$_3$, and —CH$_2$CH$_3$;

R$^{2c}$ is, independently at each occurrence, selected from OH, —OCH$_3$, —OCH$_2$CH$_3$, CH$_3$, and —CH$_2$CH$_3$;

R$^{2d}$ is, independently at each occurrence, selected from H, R$^{4c}$, C$_{1-4}$ alkyl substituted with 0-2 R$^{4c}$, C$_{3-6}$ cycloalkyl substituted with 0-2 R$^{4c}$, phenyl substituted with 0-2 R$^{4c}$, and 5-6 membered aromatic heterocycle substituted with 0-2 R$^{4c}$ and consisting of: carbon atoms and 1-4 heteroatoms selected from N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

alternatively, NR$^{2d}$R$^{2d}$ forms a 5 or 6 membered saturated, partially saturated, or unsaturated ring consisting of: 0-1 additional heteroatoms selected from N, O, and S(O)$_p$;

R$^{2e}$ is, independently at each occurrence, selected from H, R$^{4c}$, C$_{1-4}$ alkyl substituted with 0-2 R$^{4c}$, C$_{3-6}$ cycloalkyl substituted with 0-2 R$^{4c}$, phenyl substituted with 0-2 R$^{4c}$, and 5-6 membered aromatic heterocycle substituted with 0-2 R$^{4c}$ and consisting of: carbon atoms and 1-4 heteroatoms selected from N, O, and S(O)$_p$, provided that R$^{2e}$ forms other than a C(O)-halo or C(O)—S(O)$_p$, moiety;

R$^{4}$ is, independently at each occurrence, selected from H, =O, CH$_3$, —CH$_2$CH$_3$, —CH$_2$CH$_2$CH$_3$, —CH(CH$_3$)$_2$, CH$_2$CH$_2$CH$_2$CH$_3$, CH$_2$CH(CH$_3$)$_2$, CH(CH$_3$)CH$_2$CH$_3$, and C(CH$_3$)$_3$;

R$^{4a}$ is selected from —(CH$_2$)$_r$—C$_{5-6}$ carbocycle substituted with 0-3 R$^{4c}$, and —(CH$_2$)$_r$-5-6 membered heterocycle substituted with 0-3 R$_{4c}$ and consisting of: carbon atoms and 1-4 heteroatoms selected from N, O, and S(O)$_p$;

alternatively, R$^{4a}$ is selected from —(CH$_2$)$_r$NR$^{2d}$R$^{2d}$, —(CH$_2$)$_r$N(→O)R$^{2d}$R$^{2d}$, —(CH$_2$)$_r$OR$^{2d}$, —(CH$_2$)$_r$—C(O)NR$^{2d}$R$^{2d}$, —(CH$_2$)$_r$—NR$^{2d}$C(O)R$^{2e}$, —(CH$_2$)$_r$—C(O)R$^{2e}$, —(CH$_2$)$_r$—NR$^{2d}$C(O)NR$^{2d}$R$^{2d}$, —(CH$_2$)$_r$—NR$^{2d}$C(O)OR$^{2d}$, —(CH$_2$)$_r$—NR$^{2d}$SO$_2$R$^{2d}$, and —(CH$_2$)$_r$—S(O)$_p$R$^{2d}$, provided that —S(O)$_p$R$^{2d}$ forms other than —S(O)$_2$H or —S(O)H;

R$^{4b}$ is, independently at each occurrence, selected from H, =O, —OR$^3$, —CH$_2$OR$^3$, F, Cl, CH$_3$, —CH$_2$CH$_3$, —NR$^3$R$^{3a}$, —CH$_2$NR$^3$R$^{3a}$, —C(O)R$^3$, —C(O)OR$^{3c}$, —NR$^3$C(O)R$^{3a}$, —C(O)NR$^3$R$^{3a}$, —SO$_2$NR$^3$R$^{3a}$, —NR$^3$SO$_2$-phenyl, —S(O)$_2$CH$_3$, —S(O)$_2$-phenyl, and CF$_3$; and R$^{4c}$ is, independently at each occurrence, selected from =O, OH, OH, —OCH$_3$, —OCH$_2$CH$_3$, —OCH$_2$CH$_2$CH$_3$, —OCH(CH$_3$)$_2$, CH$_3$, —CH$_2$CH$_3$, —CH$_2$CH$_2$CH$_3$, —CH(CH$_3$)$_2$, C$_{2-3}$alkenyl, C$_{2-3}$ alkynyl, —CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, F, Br, Cl, CF$_3$, —NR$^2$R$^{2a}$, —CH$_2$NR$^2$R$^{2a}$, —N(→O)R$^2$R$^{2a}$, —CH$_2$N(→O)R$^2$R$^{2a}$, —C(O)R$^{2c}$, —CH$_2$C(O)R$^{2c}$, —NR$^2$C(O)R$^{2b}$, —CH$_2$NR$^2$C(O)R$^{2b}$, —C(O)NR$^2$R$^{2a}$, —CH$_2$C(O)NR$^2$R$^{2a}$, —SO$_2$NR$^2$R$^{2a}$, —CH$_2$SO$_2$NR$^2$R$^{2a}$, —NR$^2$SO$_2$R$^{5a}$, —CH$_2$NR$^2$SO$_2$R$^{5a}$, —S(O)$_p$R$^{5a}$, —CH$_2$S(O)$_p$R$^{5a}$, CF$_3$, cyclopropyl substituted with 0-1 R$^{4b}$, cyclobutyl substituted with 0-1 R$^{4b}$, cyclopentyl substituted with 0-1 R$^{4b}$, phenyl substituted with 0-1 R$^{4b}$, —CH$_2$-cyclopropyl substituted with 0-1 R$^{4b}$, —CH$_2$-cyclobutyl substituted with 0-1 R$^{4b}$, —CH$_2$-cyclopentyl substituted with 0-1 R$^{4b}$, benzyl substituted with 0-2 R$^{4b}$, 5-6 membered aromatic heterocycle consisting of carbon atoms and 1-4 heteroatoms selected from N, O, and S(O)$_p$, and substituted with 0-2 R$^{4b}$, and —(CH$_2$)-5-6 membered aromatic heterocycle consisting of carbon atoms and 1-4 heteroatoms selected from N, O, and S(O)$_p$, and substituted with 0-2 R$^{4b}$.

6. A compound according to claim 5, wherein the compound is selected from:

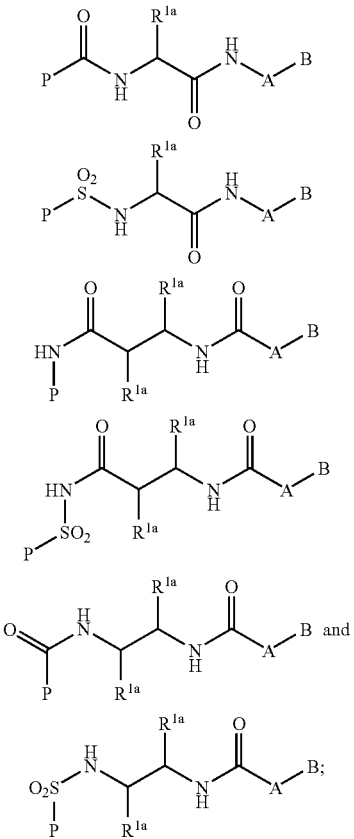

P is selected from:

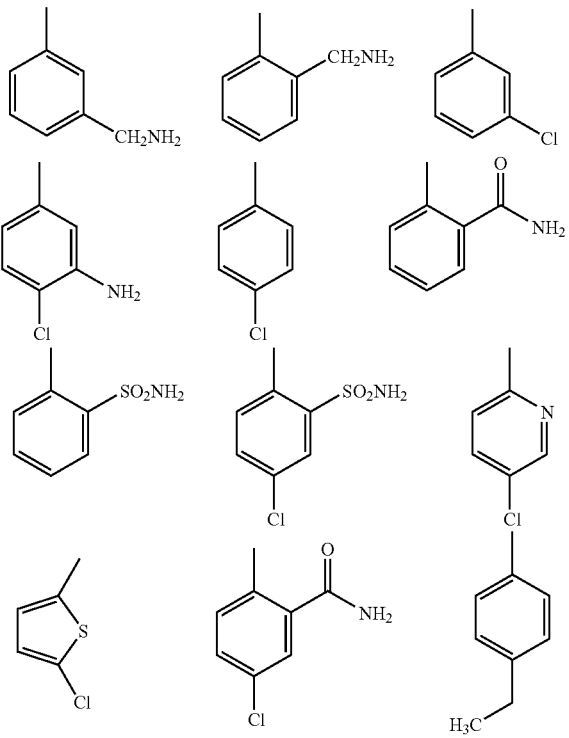

-continued

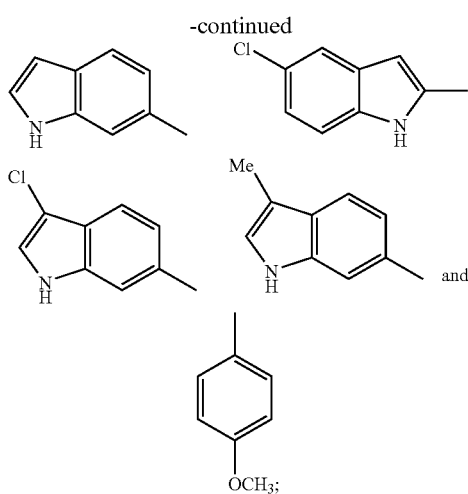

B is selected from:

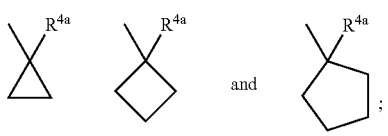

$R_{2d}$ is, independently at each occurrence, selected from H, $C_{1-4}$ alkyl substituted with 0-1 $R^{4c}$, $C_{3-6}$ cycloalkyl substituted with 0-2 $R^{4c}$, phenyl substituted with 0-2 $R^{4c}$, and a 5-6 membered aromatic heterocycle consisting of: carbon atoms and 1-4 heteroatoms selected from N, O, and $S(O)_p$, provided that $R^{2d}$ forms other than a N-halo, N—C-halo, $S(O)_p$-halo, O-halo, N—S, S—N, $S(O)_p$—$S(O)_p$, S-O, O—N, O—S, or O—O moiety;
alternatively, $NR^{2d}R^{2d}$ forms a 5 or 6 membered saturated or partially saturated ring consisting of: 0-1 additional heteroatoms selected from N, O, and $S(O)_p$;
$R^{2e}$ is, independently at each occurrence, selected from H, $C_{1-4}$ alkyl substituted with 0-1 $R^{4c}$, $C_{3-6}$ cycloalkyl substituted with 0-2 $R^{4c}$, phenyl, substituted with 0-2 $R^{4c}$, and 5-6 membered aromatic heterocycle consisting of: carbon atoms and 1-4 heteroatoms selected from N, O, and $S(O)_p$, provided that $R^{2e}$ forms other than a C(O)-halo or C(O)—$S(O)_p$ moiety;
$R^{4a}$ is selected from —$NR^{2d}R^{2d}$, —$CH_2NR^{2d}R^{2d}$, —N(→O)$R^{2d}R^{2d}$, —$CH_2N(\to O)R^{2d}R^{2d}$, —$CH_2OR^{2d}$, —C(O)$R^{2e}$, —C(O)$NR^{2d}R^{2d}$, —$CH_2C(O)NR^{2d}R^{2d}$, —$NR^{2d}(O)R^{2e}$, —$CH_2NR^{2d}C(O)R^{2e}$, —$NR^{2d}C(O)NR^{2d}R^{2d}$, —$CH_2NR^{2d}$, C(O)$NR^{2d}R^{2d}$, —$NR^{2d}C(O)OR^{2d}$, —$CH_2NR^{2d}C(O)OR^{2d}$, —$NR^{2d}SO_2R^{2d}$, —$CH_2NR^{2d}SO_2R^{2d}$, —$S(O)_pR^{2d}$, —$CH_2S(O)_pR^{2d}$, —$(CH_2)_{0-1}$—$C_{5-6}$ carbocycle substituted with 0-2 $R^{4c}$, and —$(CH_2)_{0-1}$-5-6 membered heterocycle substituted with 0-2 $R^{4c}$ and consisting of: carbon atoms and 1-4 heteroatoms selected from N, O, and $S(O)_p$, provided that —$S(O)_pR^{2d}$ forms other than —$S(O)_2H$ or —$S(O)H$; and
$R^{4c}$ is, independently at each occurrence, selected from =O, OH, —$OCH_3$, —$OCH_2CH_3$, —$OCH_2CH_2CH_3$, —$OCH(CH_3)_2$, $CH_3$, —$CH_2CH_3$, —$CH_2CH_2CH_3$, —$CH(CH_3)_2$, —$CH=CH_2$, —$CH\equiv CH$, —$CH_2OH$, —$CH_2OCH_3$, —$CH_2OCH_2CH_3$, —$CH_2OCH_2CH_2CH_3$, —$CH_2OCH(CH_3)_2$, F, Br, Cl, $CF_3$, —$NR^2R^{2a}$, —$CH_2NR^2R^{2a}$, —C(O)$R^{2c}$, —$CH_2C(O)R^{2c}$, —$NR^2C(O)R^{2b}$, —$CH_2NR^2C(O)R^{2b}$, C(O)$NR^2R^{2a}$, $CH_2C(O)NR^2R^{2a}$, $SO_2NR^2R^{2a}$, and $CH_2SO_2NR^2R^{2a}$.

7. A compound according to claim 6, wherein:
A—B is selected from:

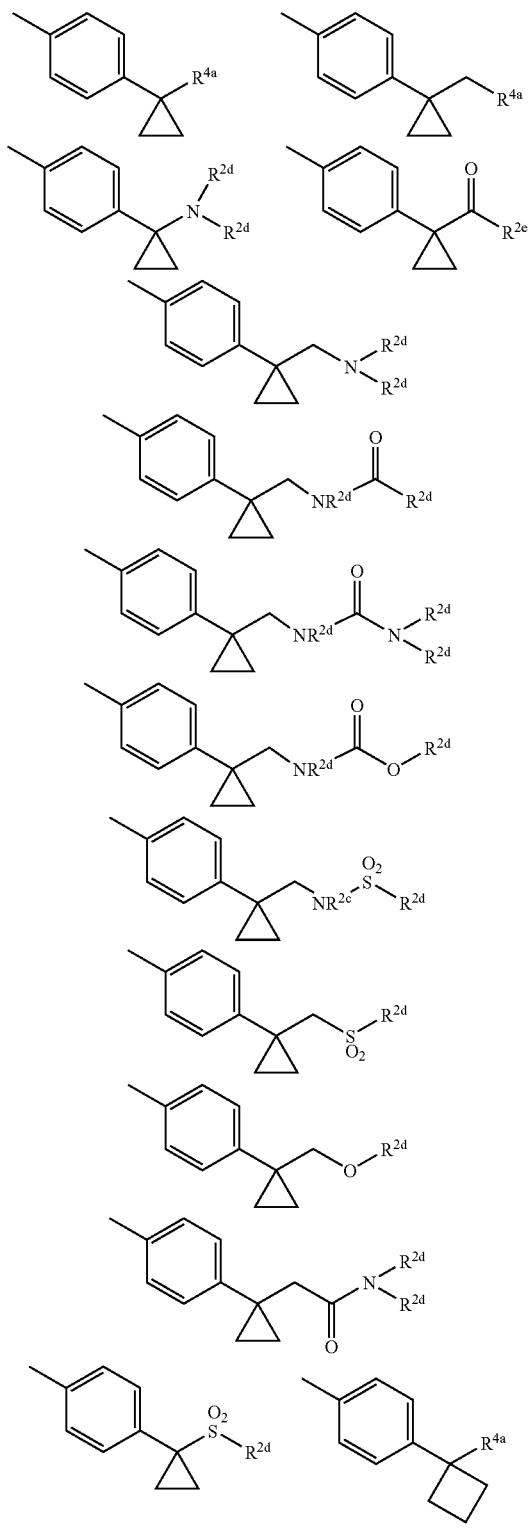

-continued
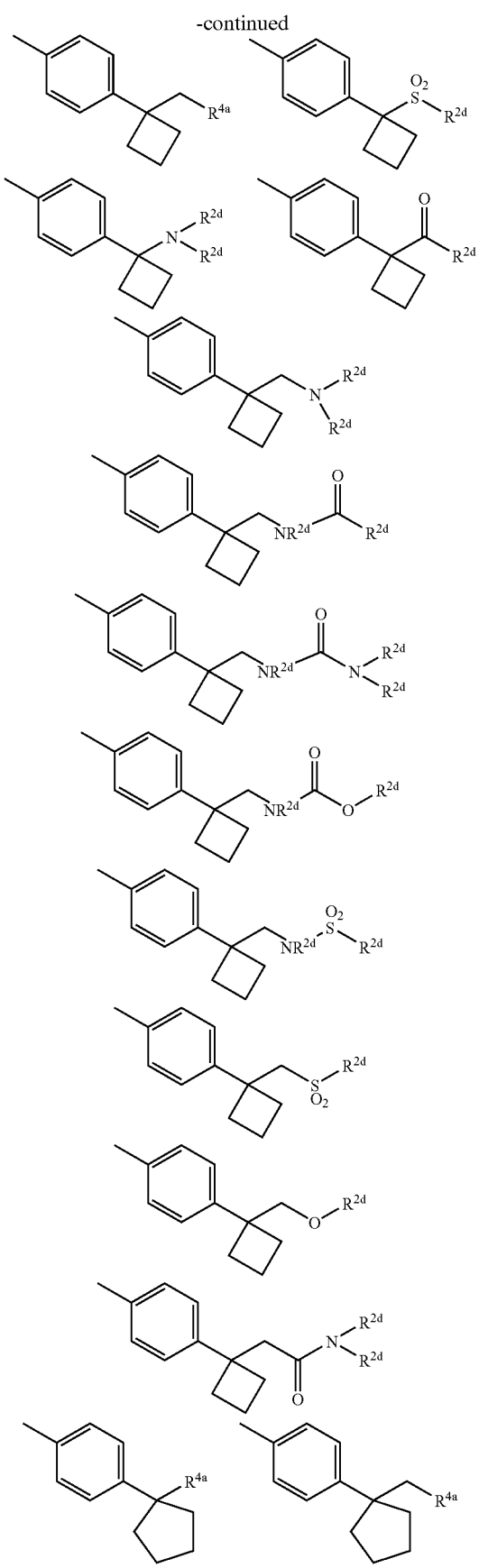
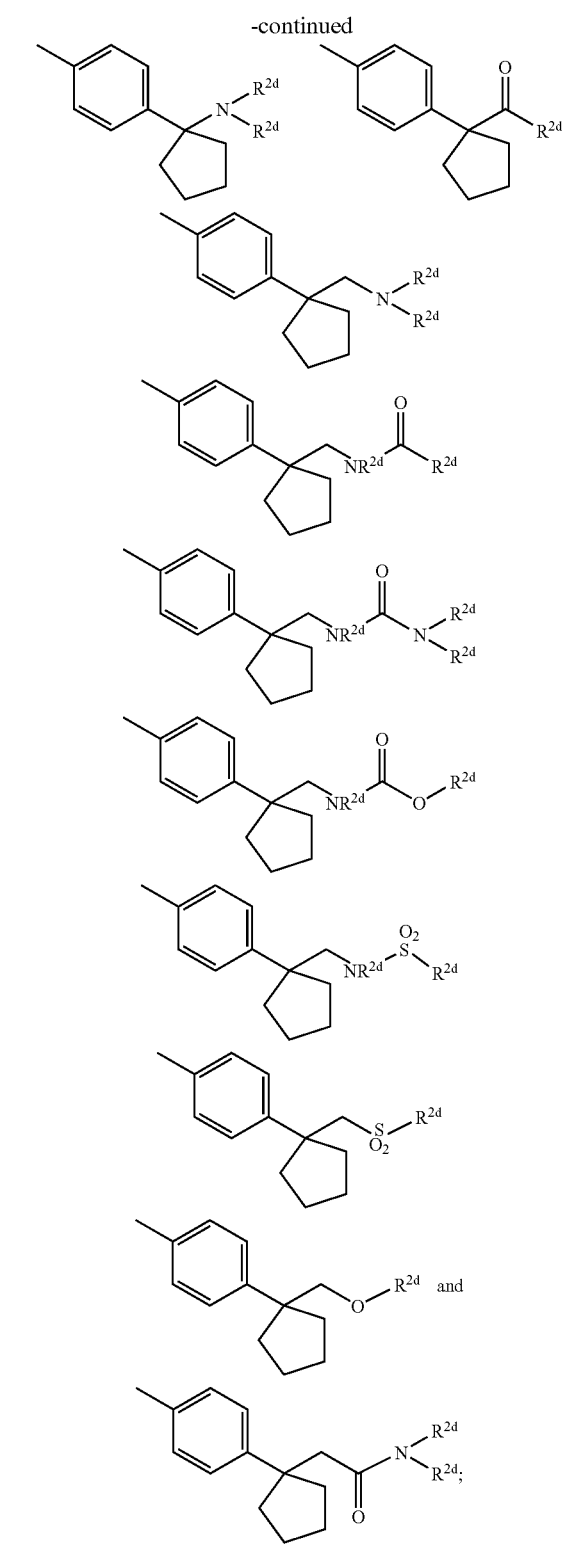
$R^{2d}$ is, independently at each occurrence, selected from H, $CH_3$, $-CH_2CH_3$, $-CH_2CH_2CH_3$, $-CH(CH_3)_2$, $-CH_2CH(CH_3)_2$, $-CH_2CH_2CH(CH_3)_2$, $-CH_2C(CH_3)_3$, $-CH_2CH_2OH$, $-CH_2C(O)NH_2$, cyclopropyl, $-CH_2$-cyclopropyl, cyclobutyl, cyclopentyl, and thiazolyl;

alternatively, $NR^{2d}R^{2d}$ forms a 5 or 6 membered saturated ring consisting of: 0-1 additional heteroatoms selected from N, O, and $S(O)_p$;

$R_{2e}$ is, independently at each occurrence, selected from $CH_3$, —$CH_2CH_3$, —$CH_2CH_2CH_3$, —$CH(CH_3)_2$, —$CH_2CH(CH_3)_2$, —$CH_2CH_2CH(CH_3)_2$, —$CH_2$-cyclopropyl, cyclopropyl, and cyclopentyl;

$R^{4a}$ is substituted with 0-2 $R^{4c}$ and selected from morpholine, 1,1-dioxo-thiomorpholine, dihydropyridine, piperidine, piperazine, pyrrolidine, imidazole, imidazoline, imidazolidine, oxazoline, and thiazoline; and $R^{4c}$ is selected from =O, OH, —$OCH_3$, and $CH_3$.

8. A compound according to claim 1, wherein the compound is selected from the group:

N-[2-(4-chloro-phenylcarbamoyl)-ethyl]-4-(1-pyrrolidin-1-ylmethyl-cyclopropyl)-benzamide;

5-chloro-thiophene-2-carboxylic acid {2-[4-(1-dimethyl-aminomethyl-cyclopropyl)-benzoylamino]-ethyl}-amide;

5-chloro-1H-indole-2-carboxylic acid {2-[4-(1-pyrrolidin-1-ylmethyl-cyclopropyl)-benzoylamino]-ethyl}-amide;

4-chloro-phenyl-carboxylic acid {2-[4-(1-pyrrolidin-1-ylmethyl-cyclopropyl)-benzoylamino]-ethyl}-amide;

4-chloro-phenyl-carboxylic acid {2-[4-(1-morpholin-4-ylmethyl-cyclopropyl)-benzoylamino]-ethyl}-amide;

4-chloro-phenyl-carboxylic acid {2-[4-(1-dimethyl-aminomethyl-cyclopropyl)-benzoylamino]-ethyl}-amide;

N-[2-(5-chloro-thiophene-2-sulfonylamino)-ethyl]-4-(1-pyrrolidin-1-ylmethyl-cyclopropyl)-benzamide; and 5-chloro-thiophene-2-carboxylic acid {phenyl-[4-(1-pyrrolidin-1-ylmethyl-cyclopropyl)-phenylcarbamoyl]-methyl}-amide;

a stereoisomer or pharmaceutically acceptable salt or solvate thereof.

9. A pharmaceutical composition, comprising: a pharmaceutically acceptable carrier and a therapeutically effective amount of a compound of claim 1 or a stereoisomer or pharmaceutically acceptable salt or solvate thereof.

10. A pharmaceutical composition, comprising: a pharmaceutically acceptable carrier and a therapeutically effective amount of a compound of claim 2 or a stereoisomer or pharmaceutically acceptable salt or solvate thereof.

11. A pharmaceutical composition, comprising: a pharmaceutically acceptable carrier and a therapeutically effective amount of a compound of claim 3 or a stereoisomer or pharmaceutically acceptable salt or solvate thereof.

12. A pharmaceutical composition, comprising: a pharmaceutically acceptable carrier and a therapeutically effective amount of a compound of claim 4 or a stereoisomer or pharmaceutically acceptable salt or solvate thereof.

13. A pharmaceutical composition, comprising: a pharmaceutically acceptable carrier and a therapeutically effective amount of a compound of claim 5 or a stereoisomer or pharmaceutically acceptable salt or solvate thereof.

14. A pharmaceutical composition, comprising: a pharmaceutically acceptable carrier and a therapeutically effective amount of a compound of claim 6 or a stereoisomer or pharmaceutically acceptable salt or solvate thereof.

15. A pharmaceutical composition, comprising: a pharmaceutically acceptable carrier and a therapeutically effective amount of a compound of claim 7 or a stereoisomer or pharmaceutically acceptable salt or solvate thereof.

16. A pharmaceutical composition, comprising: a pharmaceutically acceptable carrier and a therapeutically effective amount of a compound of claim 8 or a stereoisomer or pharmaceutically acceptable salt or solvate thereof.

* * * * *